United States Patent [19]

Brate et al.

[11] Patent Number: 5,843,634
[45] Date of Patent: Dec. 1, 1998

[54] GENETICALLY ENGINEERED ENZYMES AND THEIR CONJUGATES FOR DIAGNOSTIC ASSAYS

[75] Inventors: Elaine M Brate, Grayslake; Catherine A. Brennan, Libertyville; Dominique P. Bridon, Morton Grove, all of Ill.; Keeve D. Jaffe, Trevor, Wis.; Grant A. Krafft, Glenview, Ill.; Wlodzimierz Mandecki; Steven C. March, both of Libertyville, Ill.; John C. Russell, Greenfield, Wis.; Vincent T. Yue, Deerfield, Ill.

[73] Assignee: Abbott Laboratories, Abbott Park, Ill.

[21] Appl. No.: 657,392

[22] Filed: Jun. 4, 1996

Related U.S. Application Data

[63] Continuation of Ser. No. 100,708, Jul. 29, 1993, abandoned, which is a continuation-in-part of Ser. No. 31,165, Mar. 9, 1993, abandoned.

[51] Int. Cl.$^6$ ............................... C12N 9/16; C12N 15/55; C12Q 1/44; C07K 19/00
[52] U.S. Cl. ............................... 435/4; 435/195; 435/196; 435/7.1; 435/7.6; 435/7.9; 530/402; 536/23.2
[58] Field of Search .................................. 435/4, 7.1, 7.6, 435/7.9, 195, 196; 530/402; 536/23.2

[56] References Cited

U.S. PATENT DOCUMENTS

| | | | |
|---|---|---|---|
| 3,817,837 | 6/1974 | Rubenstein et al. | 195/103.5 |
| 3,852,157 | 12/1974 | Rubenstein et al. | 195/63 |
| 3,905,871 | 9/1975 | Rubenstein et al. | 195/63 |
| 4,550,075 | 10/1985 | Bacquet et al. | 435/7 |
| 4,708,929 | 11/1987 | Henderson | 435/7 |
| 5,053,520 | 10/1991 | Bieniarz et al. | 548/520 |
| 5,188,938 | 2/1993 | Khanna et al. | 435/7.7 |

FOREIGN PATENT DOCUMENTS

| | | |
|---|---|---|
| 2019665 | 12/1990 | Canada. |
| 0441252 | 8/1991 | European Pat. Off.. |
| 0502812 | 9/1992 | European Pat. Off.. |
| WO9207268 | 4/1992 | WIPO. |

OTHER PUBLICATIONS

C. Brennan et al., "Modulation of enzyme activity by antibody binding to an alkaline phosphatase–epitope hybrid protein", *Protein Engineering*, vol. 7, (1994) pp. 509–514.

F. Ducancel et al., "Anticorps colorimétriques recombinants: construction génétique et production chez *E. coli*", *Comptes Rendues de l'Académie des Science, Série III, Science de la Vie*, vol. 315 (1992), pp. 221–224.

D. Gillet et al, "Enzyme Immunoassay Using a Rat Prolactin–Alkaline Phosphatase Recombinant Tracer", *Analytical Chemistry*, vol. 65 (1993), pp. 1779–1784.

L. Chen et al., "3–D Structure of a mutant (Asp101→Ser) of *E. coli* alkaline phosphatase with higher catalytic activity", *Protein Engineering*, vol. 5 (1992) pp. 605–610.

(List continued on next page.)

*Primary Examiner*—Robert A. Wax
*Assistant Examiner*—William W. Moore
*Attorney, Agent, or Firm*—Andreas M. Danckers

[57] ABSTRACT

This invention relates to genetically engineered enzymes, their ligand conjugates, their manufacture, and their use in qualitative or quantitative assays. A hybrid enzyme, such as an AP-epitope, has a foreign amino acid moiety (an epitope) inserted near the active site of the starting AP enzyme. The foreign amino acid moiety binds with an analyte, and, as a consequence of this binding, the enzymatic activity of the hybrid enzyme, AP-epitope, is modified. The changes in the enzymatic activity are dependent upon the presence, or the amount, of the analyte. In another embodiment, the hybrid enzyme consists of a cysteine introduced near the active site of an AP to give a hybrid enzyme. The cysteine on the hybrid enzyme serves as a point of conjugation of a ligand, such as theophylline, ferritin, thyroxine, or digoxigenin, to form the hybrid enzyme-ligand conjugate. The ligand binds with an antibody, an analyte or a binding molecule to an analyte and as a result of this binding, the enzymatic activity of the hybrid enzyme-ligand conjugate is modified or modulated.

20 Claims, 34 Drawing Sheets

OTHER PUBLICATIONS

E.E. Kim et al., "Reaction Mechanism of Alkaline Phosphatase Based on Crystal Structures", *Journal of Molecular Biology*, 218, (1991) pp. 449–464.

J.M. Sowadski et al., "Refined Structure of Alkaline Phosphatase from *Escherichia coli* at 2·8 Å Resolution", *Journal of Molecular Biology*, 186, (1985) pp. 417–433.

H. Inouye et al., "Alkaline Phosphatase Synthesis in a Cell–free System Using DNA and RNA Templates", *Journal of Molecular Biology*, 110, (1977) pp. 75–87.

P.I. Freimuth et al., "Introduction of Guest Peptides into *Escherichia coli* Alkaline Phosphatase", *Journal of Biological Chemistry*, 265, (1990) pp. 896–901.

F.M. Hulett et al., "Bacillus subtilis Alkaline Phosphatases III and IV", *Journal of Biological Chemistry*, 266, (1991) pp. 1077–1084.

C.N. Chang et al. "Nucleotide sequenace of the alkaline phosphatase gene of *Escherichia coli*", *Gene*, 44 (1986) pp. 121–125.

C. Yanisch–Perron et al., "Improved M13 phage cloning vectors and host strains: Nucleotide sequences of the M13mkp18 and pUC19 vectors", *Gene*, 33, (1985) pp. 103–119.

W. Mandecki et al., "A totally synthetic plasmid for general cloning, gene expression and mutagenesis in *Escherichia coli*", *Gene*, 94 (1990) pp. 103–107.

G.J. LaRosa et al., "Conserved Sequence and Structural Elements in the HIV–1 Principal Neutralizing Determinant", *Science* 249 (1990) pp. 932–935.

J.E. Butler–Ransohoff et al., "Use of site–directed mutagenesis to elucidate the role of arginine–166 in the catalytic mechanism of alkaline phosphatase", *Proc. Natl. Acad. Science USA*, 85 (1988) pp. 4276–4278.

P. Freimuth et al., "Insertion of Myoglobin T–Cell Epitopes into the *Escherichia Coli* Alkaline Phosphatase", *Res. Microbiol.*, 141, (1990) pp. 995–1001.

H.T. Langen et al., "Alkaline Phosphatase–Somatostatin Hybrid Proteins as Probes for Somatostatin–14 Receptors", *PROTEINS: Structure, Function, and Genetics*, 14, (1992) pp. 1–9.

A. Chaidaroglou et al., "Alteration of aspartate 101 in the active site of *Escherichia coli* alkaline phosphatase enhances the catalytic activity", *Protein Engineering*, 3 (1989) pp. 127–132.

D. Gillet et al., "Insertion of a disulfide–containing neurotoxin into *E.coli* alkaline phosphatase: the hybrid retains both biological activities", *Protein Engineering*, 5 (1992) pp. 273–278.

W. Mandecki et al., "Mutagenesis of conserved residues within the active sites of *Escherichia coli* alkaline phosphatase yields enzymes with increased $K_{cat}$", *Protein Engineering*, 4 (1991) pp. 801–804.

H. Zhang et al.,"Double stranded DNA sequencing as a choice for DNA sequencing", *Nucleic Acids Research*, 16 (1988) p. 1220.

U.K. Laemmli, "Cleavage of Structural Proteins during the Assembly of the Head of Bacteriophage T4", *Nature*, 227, (1970) pp. 680–685.

T.A. Kunkel, "Rapid and efficient site–specific mutagenesis without phenotypic selection", *Proc. Natl. Acad. Sci. USA*, 82, (1985) pp. 488–492.

J–M Bidart et al., "Identification of Epitopes Associated with hCG and the βhCG Carboxyl Terminus by Monoclonal Antibodies Produced against a Synthetic Peptide," *The Journal of Immunology*, 134 (1985), p. 457.

J.M. Addison et al,. "The location of antigenic sites on ferritin molecules", *FEBS Letters*, 175 (1984) pp. 333–336.

A.I. MacLean et al., "Attaching Analytes in the Proximity of the Active Sites of Enzymes", *J. Chem. Soc.., Chem. Commun.*, 18 (1992), pp. 1283–1285.

G.L. Ellman, "A Colorimetric Method for Determining Low Concentrations of Mercaptans", *Archives of Biochemistry and Biophysics*, 74 (1958), pp. 443–450.

T. Maniatis, *Molecular Cloning a Laboratory Manual*, Cold Spring Harbor Laboratory, 1982.

J. Ellman et al., "Biosynthetic Method for Introducing Unnatural Amino Acids Site–Specifically into Proteins", *Methods in Enzymology*, vol. 202 (1991), pp. 301–337.

Ullman, E.F., et al., 1979, Biochimica et Biophysica Acta, *567(1)*:66–74.

```
         10         20         30         40         50
    GATCCTTGTA CATGGAGAAA ATAAAGTGAA ACAGTCGACT ATTGCACTGG 60         70         80         90        100
    CACTCTTACC GTTACTGTTT ACCCCTGTGA CAAAAGCCCG TACACCAGAA 110        120        130        140        150
    ATGCCTGTTC TCGAAAACCG GGCTGCTCAG GGCGATATTA CTGCACCCGG 160        170        180        190        200
    GGGTGCGCGC CGTTTAACGG GTGACCAGAC TGCAGCTCTG CGCGATTCTC 210        220        230        240        250
    TTAGCGATAA ACCGGCAAAA AATATTATTT TGCTGATTGG CGATGGTATG 260        270        280        290        300
    GGGGACTCGG AAATTACCGC GGCACGTAAC TATGCCGAAG GTGCGGGCGG 310        320        330        340        350
    CTTTTTTAAA GGTATAGATG CCTTACCGTT AACCGGGCAA TACACTCACT
                                        |
                                       HpaI 360        370        380        390        400
    ATGCGCTGAA TAAAAAAACC GGCAAACCGG ACTACGTAAC CGACTCGGCT
                                        |
                                       SnaBI
        410        420        430        440        450
    GCATCAGCAA CCGCCTGGTC AACCGGTGTC AAAACCTATA ACGGCGCGCT 460        470        480        490        500
    GGGCGTCGAT ATCCACGAAA AAGATCACCC AACGATCCTG GAAATGGCAA 510        520        530        540        550
    AAGCAGCTGG TCTGGCGACC GGTAACGTTT CTACCGCAGA GTTGCAGGAC 560        570        580        590        600
    GCCACACCCG CTGCGCTGGT GGCACATGTG ACTAGTCGCA AATGCTACGG
                                        |          |
                                       SpeI       RsrII
```

FIG.2A

```
          610        620        630        640        650
     TCCGAGCGCG ACCAGTGAAA AATGTCCGGG TAACGCGTTG GAAAAAGGCG 660        670        680        690        700
     GAAAAGGATC TATTACCGAA CAGTTGCTGA ATGCTCGTGC CGACGTTACG 710        720        730        740        750
     CTTGGCGGCC GCGCAAAAAC CTTTGCTGAA ACGGCAACCG CCGGCGAATG 760        770        780        790        800
     GCAGGGAAAA ACTCTTCGCG AACAGGCACA GGCGCGTGGT TATCAGTTGG 810        820        830        840        850
     TGAGCGATGC TGCTAGCCTG AACTCGGTGA CGGAAGCGAA TCAGCAAAAA 860        870        880        890        900
     CCCCTGCTAG GCCTGTTTGC TGACGGCAAT ATGCCAGTGC GCTGGCTGGG 910        920        930        940        950
     CCCCAAAGCA ACTTATCATG GCAATATCGA CAAGCCCGCA GTCACTTGCA 960        970        980        990       1000
     CGCCAAATCC GCAACGTAAC GACTCGGTTC CAACCCTGGC GCAGATGACC 1010       1020       1030       1040       1050
     GACAAAGCCA TTGAACTCTT AAGTAAAAAT GAGAAAGGCT TTTTCCTGCA 1060       1070       1080       1090       1100
     AGTTGAAGGT GCGTCAATCG ATAAACAGGA TCATGCTGCC AATCCTTGTG 1110       1120       1130       1140       1150
     GCCAAATTGG CGAGACGGTA GATCTCGATG AAGCCGTTCA ACGGGCGCTG 1160       1170       1180       1190       1200
     GAGTTCGCTA AAAAGGAGGG TAACACGTTG GTCATAGTCA CCGCTGATCA 1210       1220       1230       1240       1250
     CGCCCACGCC AGCCAGATTG TTGCTCCGGA TACCAAAGCT CCGGGTTTGA 1260       1270       1280       1290       1300
     CCCAGGCGCT AAATACCAAA GATGGCGCCG TGATGGTCAT GAGTTACGGG
                                   |
                                 KasI
```

FIG. 2B

```
     1310       1320       1330       1340       1350
AACTCCGAAG AGGATAGCCA AGAGCACACC GGCAGTCAGT TGCGTATTGC 1360       1370       1380       1390       1400
GGCGTATGGC CCGCATGCCG CCAATGTTGT AGGGCTGACC GACCAGACCG
                    |
                  SphI 1410       1420       1430       1440       1450
ATCTCTTCTA CACCATGAAA GCCGCCCTTG GGCTGAAATA ATAGCAGGTA

1460
AGCT
```

FIG.2C

10
Thr Pro Glu MET Pro Val Leu Glu Asn Arg Ala Ala Gln Gly
                    20
Asp Ile Thr Ala Pro Gly Gly Ala Arg Arg Leu Thr Gly Asp
        30                                      40
Gln Thr Ala Ala Leu Arg Asp Ser Leu Ser Asp Lys Pro Ala
                            50
Lys Asn Ile Ile Leu Leu Ile Gly Asp Gly MET Gly Asp Ser
                60                                      70
Glu Ile Thr Ala Ala Arg Asn Tyr Ala Glu Gly Ala Gly Gly
                                80
Phe Phe Lys Gly Ile Asp Ala Leu Pro Leu Thr Gly Gln Tyr
                        90
Thr His Tyr Ala Leu Asn Lys Lys Thr Gly Lys Pro Asp Tyr
        100                                     110
Val Thr Asp Ser Ala Ala Ser Ala Thr Ala Trp Ser Thr Gly
                            120
Val Lys Thr Tyr Asn Gly Ala Leu Gly Val Asp Ile His Glu
                130                                     140
Lys Asp His Pro Thr Ile Leu Glu MET Ala Lys Ala Ala Gly
                                150
Leu Ala Thr Gly Asn Val Ser Thr Ala Glu Leu Gln Asp Ala
                            160
Thr Pro Ala Ala Leu Val Ala His Val Thr Ser Arg Lys Cys
        170                                     180
Tyr Gly Pro Ser Ala Thr Ser Glu Lys Cys Pro Gly Asn Ala
                            190
Leu Glu Lys Gly Gly Lys Gly Ser Ile Thr Glu Gln Leu Leu
                200                                     210
Asn Ala Arg Ala Asp Val Thr Leu Gly Gly Gly Ala Lys Thr
                            220
Phe Ala Glu Thr Ala Thr Ala Gly Glu Trp Gln Gly Lys Thr
                        230
Leu Arg Glu Gln Ala Gln Ala Arg Gly Tyr Gln Leu Val Ser
        240                                     250
Asp Ala Ala Ser Leu Asn Ser Val Thr Glu Ala Asn Gln Gln
                            260
Lys Pro Leu Leu Gly Leu Phe Ala Asp Gly Asn MET Pro Val
                270                                     280
Arg Trp Leu Gly Pro Lys Ala Thr Tyr His Gly Asn Ile Asp

FIG.2D

```
                                          290
     Lys Pro Ala Val Thr Cys Thr Pro Asn Pro Gln Arg Asn Asp
                              300
     Ser Val Pro Thr Leu Ala Gln MET Thr Asp Lys Ala Ile Glu
         310                                      320
     Leu Leu Ser Lys Asn Glu Lys Gly Phe Phe Leu Gln Val Glu
                                      330
     Gly Ala Ser Ile Asp Lys Gln Asp His Ala Ala Asn Pro Cys
                 340                                      350
     Gly Gln Ile Gly Glu Thr Val Asp Leu Asp Glu Ala Val Gln
                                              360
     Arg Ala Leu Glu Phe Ala Lys Lys Glu Gly Asn Thr Leu Val
                                  370
     Ile Val Thr Ala Asp His Ala His Ala Ser Gln Ile Val Ala
         380
     Pro Asp Thr Lys Ala Pro Gly Leu Thr Gln Ala Leu Asn Thr
                                      400
     Lys Asp Gly Ala Val MET Val MET Ser Tyr Gly Asn Ser Glu
                 410                                      420
     Glu Asp Ser Gln Glu His Thr Gly Ser Gln Leu Arg Ile Ala
                                                  430
     Ala Tyr Gly Pro His Ala Ala Asn Val Val Gly Leu Thr Asp
                                  440
     Gln Thr Asp Leu Phe Tyr Thr MET Lys Ala Ala Leu Gly Leu
     449
     Lys
```

FIG.2E api1a

```
         10         20         30         40         50
   GCGCCGTGAT GGTCATGAGT TACGGGAACT CCGAAGAGAT CCGTATCCAG 60         70         80         90        100
   CGTGGTCCGG GTCGTGCTTT CGTTACTGAT AGCCAAGAGC ACACCGGCAG 110        120        130        140
   TCAGTTGCGT ATTGCGGCGT ATGGCCCGCA TG
``` api1b

```
         10         20         30         40         50
   CGGGCCATAC GCCGCAATAC GCAACTGACT GCCGGTGTGC TCTTGGCTAT 60         70         80         90        100
   CAGTAACGAA AGCACGACCC GGACCACGCT GGATACGGAT CTCTTCGGAG 110        120        130
   TTCCCGTAAC TCATGACCAT CACG
``` api2a

```
         10         20         30         40         50
   CTAGTCGCAA AATCCGTATC CAGCGTGGTC CGGGTCGTGC TTTCGTTACT

60
   TGCTACG
``` api2b

```
         10         20         30         40         50
   GACCGTAGCA AGTAACGAAA GCACGACCCG GACCACGCTG GATACGGATT

60
   TTGCGA
```

FIG.3A api3a

```
        10         20         30         40         50
CTAGTCGCAA ATGCATCCGT ATCCAGCGTG GTCCGGGTCG TGCTTTCGTT

60
ACTTACG
``` api3b

```
        10         20         30         40         50
GACCGTAAGT AACGAAAGCA CGACCCGGAC CACGCTGGAT ACGGATGCAT

60
TTGCGA
``` api5a

```
        10         20         30         40         50
CTAGTCGCAA ATGCACTCGT CCGAACAACA ACACCCGTAA ATCTATCCGT 60         70         80         90        100
ATCCAGCGTG GTCCGGGTCG TGCTTTCGTT ACTATCGGTA AAATCGGTAA 110        120        130
CATGCGTCAG GCTCACTGTC CGGGTAA
``` api5b

```
        10         20         30         40         50
CGCGTTACCC GGACAGTGAG CCTGACGCAT GTTACCGATT TTACCGATAG 60         70         80         90        100
TAACGAAAGC ACGACCCGGA CCACGCTGGA TACGGATAGA TTTACGGGTG 110        120        130
TTGTTGTTCG GACGAGTGCA TTTGCGA
```

FIG. 3B api6a

```
              10         20         30         40         50
      AACCGGGCAA TACACTCACT ATGCGCTGAA TATCCGTATC CAGCGTGGTC 60         70         80         90
      CGGGTCGTGC TTTCGTTACT GGCAAACCGG ACTAC
``` api6b

```
              10         20         30         40         50
      GTAGTCCGGT TTGCCAGTAA CGAAAGCACG ACCCGGACCA CGCTGGATAC 60         70         80         90
      GGATATTCAG CGCATAGTGA GTGTATTGCC CGGTT
``` api7a

```
              10         20         30         40         50
      AACCGGGCAA TACACTCACT ATGCGCTGAA TTGCATCCGT ATCCAGCGTG 60         70         80         90
      GTCCGGGTCG TGCTTTCGTT ACTTGCGGCA AACCGGACTA C
``` api7b

```
              10         20         30         40         50
      GTAGTCCGGT TTGCCGCAAG TAACGAAAGC ACGACCCGGA CCACGCTGGA 60         70         80         90
      TACGGATGCA ATTCAGCGCA TAGTGAGTGT ATTGCCCGGT T
``` api8a

```
              10         20         30         40         50
      GCGCCGTGAT GGTCATGAGT TACGGGAACT CCGAAGAGTG CACTCGTCCG 60         70         80         90        100
      AACAACAACA CCCGTAAATC TATCCGTATC CAGCGTGGTC CGGGTCGT
```

FIG. 3C opi8b

```
            10         20         30         40         50
    GCTTTCGTTA CTATCGGTAA AATCGGTAAC ATGCGTCAGG CTCACTGTGA 60         70         80         90        100
    TAGCCAAGAG CACACCGGCA GTCAGTTGCG TATTGCGGCG TATGGCCCGC

110
    ATG
``` opi8c

```
            10         20         30         40         50
    CGGACCACGC TGGATACGGA TAGATTTACG GGTGTTGTTG TTCGGACGAG 60         70         80         90
    TGCACTCTTC GGAGTTCCCG TAACTCATGA CCATCACG
``` opi8d

```
            10         20         30         40         50
    CGGGCCATAC GCCGCAATAC GCAACTGACT GCCGGTGTGC TCTTGGCTAT 60         70         80         90        100
    CACAGTGAGC CTGACGCATG TTACCGATTT TACCGATAGT AACGAAAGCA

110
    CGACC
```

FIG. 3D

API1
-407————————insert 13 amino acids————————408-
-Glu   Ile Arg Ile Gln Arg Gly Pro Gly Arg Ala Phe Val Thr   Asp- API2
-167————————insert 13 amino acids————————168-
-Lys   Ile Arg Ile Gln Arg Gly Pro Gly Arg Ala Phe Val Thr   Cys API3
-168————————insert 13 amino acids————————169-
-Cys   Ile Arg Ile Gln Arg Gly Pro Gly Arg Ala Phe Val Thr   Tyr API5
-168————————replacement 34 amino acids————————
-Cys   Thr Arg Pro Asn Asn Asn Thr Arg Lys Ser Ile Arg Ile Gln Arg Gly Pro Gly Arg Ala Phe Val Thr Ile Gly Lys Ile Gly Asn Met Arg ————————178-
Gln Ala His Cys API6
-90————————replacement 13 amino acids————————94-
-Asn   Ile Arg Ile Gln Arg Gly Pro Gly Arg Ala Phe Val Thr   Gly API7
-90————————replacement 15 amino acids————————
-Asn   Cys Ile Arg Ile Gln Arg Gly Pro Gly Arg Ala Phe Val Thr Cys 94-
Gly API8
-407————————insert 36 amino acids————————
-Glu   Cys Thr Arg Pro Asn Asn Asn Thr Arg Lys Ser Ile Arg Ile Gln Arg Gly Pro Gly Arg Ala Phe Val Thr Ile Gly Lys Ile Gly Asn Met ————————408-
Arg Gln Ala His Cys   Asp

FIG.4

```
         BamHI                                         SalI
         GG ATC CTT GTA CAT GGA GAA AAT AAA GTG AAA CAG TCG ACT ATT CCA CTG GCA    54
                                             Val Lys Gln Ser Thr Ile Ala Leu Ala

CTC TTA CCG TTA CTG TTT ACC CCT GTG ACA AAA GCC CGT ACA CCA GAA ATG CCT  108
         Leu Leu Pro Leu Leu Phe Thr Pro Val Thr Lys Ala Arg Thr Pro Glu Met Pro    5

GTT CTC GAA AAG CGG GCT GCT CAG GGC GAT ATT ACT GCA CCC GGG GGT GCG CGC  162
         Val Leu Glu Asn Arg Ala Ala Gln Gly Asp Ile Thr Ala Pro Gly Gly Ala Arg   23

PstI
         CGT TTA ACG GGT GAC CAG ACT GCA GCT CTG CGC GAT TCT CTT AGC GAT AAA CCG  218
         Arg Leu Thr Gly Asp Gln Thr Ala Ala Leu Arg Asp Ser Leu Ser Asp Lys Pro   41

GCA AAA AAT ATT ATT TTG CTG ATT GGC GAT GGT ATG GGG GAC TCG GAA ATT ACC  270
         Ala Lys Asn Ile Ile Leu Leu Ile Gly Asp Gly Met Gly Asp Ser Glu Ile Thr   59

SacII
         GCC GCA CGT AAC TAT GCC GAA GGT GCG GGC GGC TTT TTT AAA GGT ATA GAT GCC  324
         Ala Ala Arg Asn Tyr Ala Glu Gly Ala Gly Gly Phe Phe Lys Gly Ile Asp Ala   77

HpaI
         TTA CCG TTA ACC GGG CAA TAC ACT CAC TAT GCG CTG AAT AAA AAA ACC GGC AAA  378
         Leu Pro Leu Thr Gly Gln Tyr Thr His Tyr Ala Leu Asn Lys Lys Thr Gly Lys   95

SnaBI
         CCG GAC TAC GTA ACC GAC TCG GCT GCA TCA GCA ACC GCC TGG TCA ACC GGT GTC  432
         Pro Asp Tyr Val Thr Asp Ser Ala Ala Ser Ala Thr Ala Trp Ser Thr Gly Val  113

EcoRV
         AAA ACC TAT AAC GGC GCG CTG GGC GTC GAT ATC CAC GAA AAA GAT CAC CCA ACG  486
         Lys Thr Tyr Asn Gly Ala Leu Gly Val Asp Ile His Glu Lys Asp His Pro Thr  131

ATC CTG GAA ATG GCA AAA GCA GCT GGT CTG GCG ACC GGT AAC GTT TCT ACC GCA  540
         Ile Leu Glu MET Ala Lys Ala Ala Gly Leu Ala Thr Gly Asn Val Ser Thr Ala  149

SpeI
         GAG TTG CAG GAC GCC ACA CCC GCT GCG CTG GTG GCA CAT GTG ACT AGT CGC AAA  594
         Glu Leu Gln Asp Ala Thr Pro Ala Ala Leu Val Ala His Val Thr Ser Arg Lys  167
```

FIG.15A

```
                 RarII                                    HluI
TGC TAC GGT CCG AGC GCG ACC AGT GAA AAA TGT CCG GGT AAC GCG TTG GAA AAA    648
Cys Tyr Gly Pro Ser Ala Thr Ser Glu Lys Cys Pro Gly Asn Ala Leu Glu Lys    185

BamI
GGC GGA AAA GGA TCT ATT ACC GAA CAG TTG CTG AAT GCT CGT GCC GAC GTT ACG    702
Gly Gly Lys Gly Ser Ile Thr Glu Gln Leu Leu Asn Ala Arg Ala Asp Val Thr    203

NaeI
CTT CGC GGC GGC GCA AAA ACC TTT GCT GAA ACG GCA ACC GCC GGC GAA TGG CAG    756
Leu Gly Gly Gly Ala Lys Thr Phe Ala Glu Thr Ala Thr Ala Gly Glu Trp Gln    221

NruI
GGA AAA ACT CTT CGC GAA CAG GCA CAG GCG CGT GGT TAT CAG TTG GTG AGC GAT    810
Gly Lys Thr Leu Arg Glu Gln Ala Gln Ala Arg Gly Tyr Gln Leu Val Ser Asp    239

NheI                                                         StuI
GCT GCT AGC CTG AAC TCG GTG ACG GAA GCG AAT CAG CAA AAA CCC CTG CTA GGC    864
Ala Ala Ser Leu Asn Ser Val Thr Glu Ala Asn Gln Gln Lys Pro Leu Leu Gly    257

BstXI      ApaI
CTG TTT GCT GAC GGC AAT ATG CCA GTG CGC TGG CTG GGC CCC AAA GCA ACT TAT    918
Leu Phe Ala Asp Gly Asn Met Pro Val Arg Trp Leu Gly Pro Lys Ala Thr Tyr    275

CAT GGC AAT ATC GAC AAG CCG GCA GTC ACT TGC ACG CCA AAT CCG CAA CGT AAC    972
His Gly Asn Ile Asp Lys Pro Ala Val Thr Cys Thr Pro Asn Pro Gln Arg Asn    293

AflII
GAC TCG GTT CCA ACC CTG GCG CAG ATG ACC GAC AAA GCC ATT GAA CTC TTA AGT   1026
Asp Ser Val Pro Thr Leu Ala Gln Met Thr Asp Lys Ala Ile Glu Leu Leu Ser    331

ClaI
AAA AAT GAG AAA GGC TTT TTC CTG CAA GTT GAA GGT GCG TCA ATC GAT AAA CAG   1080
Lys Asn Glu Lys Gly Phe Phe Leu Gln Val Glu Gly Ala Ser Ile Asp Lys Gln    329

BalI              BglII
GAT CAT GCT GCG AAT CCT TGT GGC CAA ATT GGC GAG ACG GTA GAT CTC GAT GAA   1134
Asp His Ala Ala Asn Pro Cys Gly Gln Ile Gly Glu Thr Val Asp Leu Asp Glu    347

GCC GTT CAA CGG GCG CTG GAG TTC GCT AAA AAG GAG GGT AAC ACG TTG GTC ATA   1188
```

FIG. 15B

```
        Ala Val Gln Arg Ala Leu Glu Phe Ala Lys Lys Glu Gly Asn Thr Leu Val Ile    365

BclI                                BspEI
        GTC ACC GCT GAT CAC GCC CAC GCC AGC CAG ATT GTT GCT CCG GAT ACC AAA GCT   1242
        Val Thr Ala Asp His Ala His Ala Ser Gln Ile Val Ala Pro Asn Thr Lys Ala    383

CCG GGT TTG ACC CAG GCG CTA AAT ACC AAA GAT GGC GCC GTG ATG GTC ATG AGT   1296
        Pro Gly Leu Thr Gln Ala Leu Asn Thr Lys Asp Gly Ala Val Met Val Met Ser    401

TAC GGG AAC TCC GAA GAG GAT AGC CAA GAG CAC ACC GGC AGT CAG TTG CGT ATT   1350
        Tyr Gly Asn Ser Glu Glu Asp Ser Gln Glu His Thr Gly Ser Gln Leu Arg Ile    419

SphI
        GCG GCG TAT GGC CCG CAT GCC GCC AAT GTT GTA GGG CTG ACC GAC CAG ACC GAT   1404
        Ala Ala Tyr Gly Pro His Ala Ala Asn Val Val Gly Leu Thr Asp Gln Thr Asp    437

StyI      BspMI                HindIII
        CTC TTC TAC ACC ATG AAA GCC GCC CTT GGG CTG AAA TAA TAG CAG GTA AGC T     1456
        Leu Phe Tyr Thr Met Lys Ala Ala Leu Gly Leu Lys                            449
```

FIG.15C

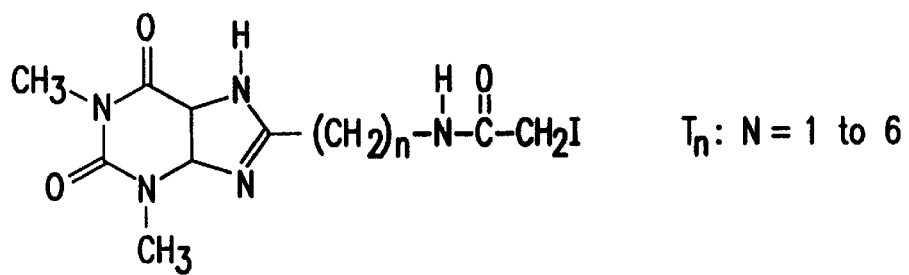
$T_n$: N = 1 to 6
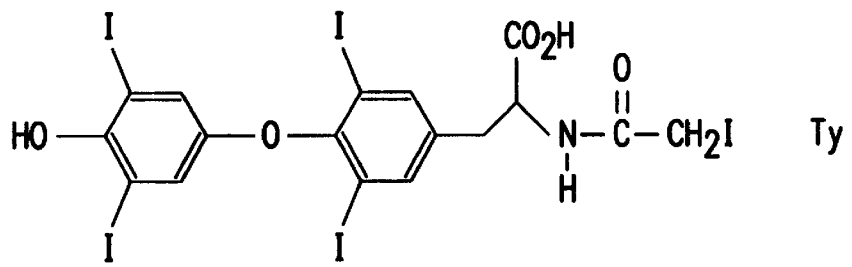
Ty
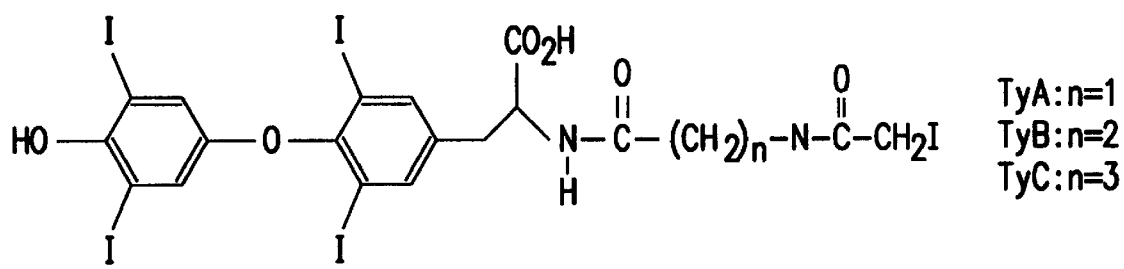
TyA: n=1
TyB: n=2
TyC: n=3
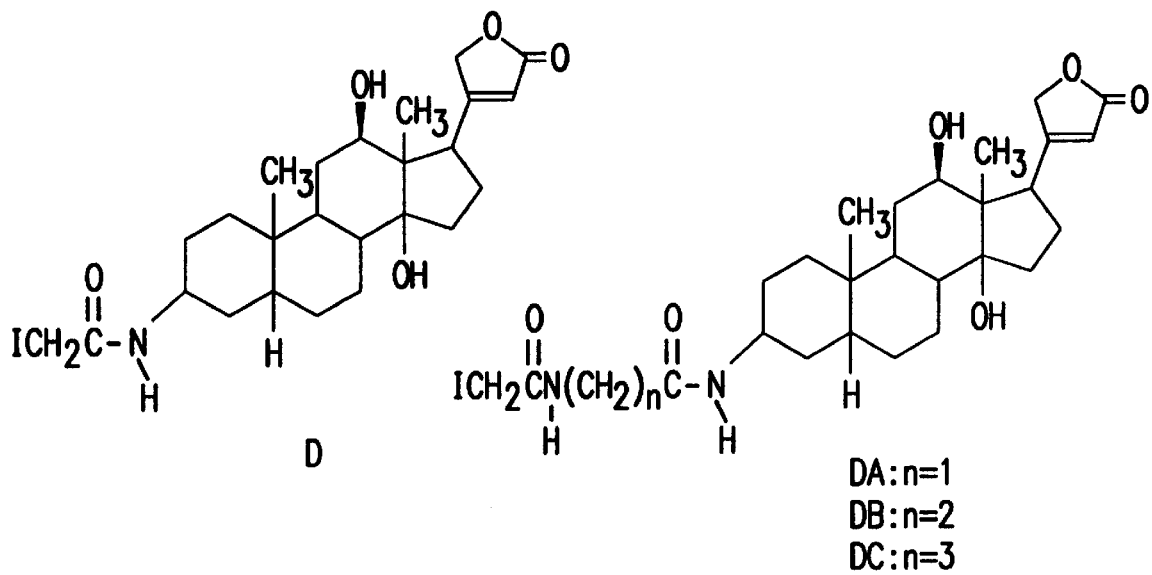
D
DA: n=1
DB: n=2
DC: n=3
FIG. 16A

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
( A ) LENGTH: 1454 nucleotides
( B ) TYPE: nucleic acid
( C ) STRANDEDNESS: double
( D ) TOPOLOGY: linear ( i i ) MOLECULE TYPE:

( v i ) ORIGINAL SOURCE:
( A ) ORGANISM: Escherichia coli ( x i ) SEQUENCE DESCRIPTION: SEQ ID NO: 1:

| | | | | | |
|---|---|---|---|---|---|
| GATCCTTGTA | CATGGAGAAA | ATAAAGTGAA | ACAGTCGACT | ATTGCACTGG | 50 |
| CACTCTTACC | GTTACTGTTT | ACCCCTGTGA | CAAAAGCCCG | TACACCAGAA | 100 |
| ATGCCTGTTC | TCGAAAACCG | GGCTGCTCAG | GGCGATATTA | CTGCACCCGG | 150 |
| GGGTGCGCGC | CGTTTAACGG | GTGACCAGAC | TGCAGCTCTG | CGCGATTCTC | 200 |
| TTAGCGATAA | ACCGGCAAAA | AATATTATTT | TGCTGATTGG | CGATGGTATG | 250 |
| GGGGACTCGG | AAATTACCGC | GGCACGTAAC | TATGCCGAAG | GTGCGGGCGG | 300 |
| CTTTTTTAAA | GGTATAGATG | CCTTACCGTT | AACCGGGCAA | TACACTCACT | 350 |
| ATGCGCTGAA | TAAAAAAACC | GGCAAACCGG | ACTACGTAAC | CGACTCGGCT | 400 |
| GCATCAGCAA | CCGCCTGGTC | AACCGGTGTC | AAAACCTATA | ACGGCGCGCT | 450 |
| GGGCGTCGAT | ATCCACGAAA | AAGATCACCC | AACGATCCTG | GAAATGGCAA | 500 |
| AAGCAGCTGG | TCTGGCGACC | GGTAACGTTT | CTACCGCAGA | GTTGCAGGAC | 550 |
| GCCACACCCG | CTGCGCTGGT | GGCACATGTG | ACTAGTCGCA | AATGCTACGG | 600 |
| TCCGAGCGCG | ACCAGTGAAA | AATGTCCGGG | TAACGCGTTG | GAAAAGGCG | 650 |
| GAAAGGATC | TATTACCGAA | CAGTTGCTGA | ATGCTCGTGC | CGACGTTACG | 700 |
| CTTGGCGGCG | GCGCAAAAAC | CTTTGCTGAA | ACGGCAACCG | CCGGCGAATG | 750 |
| GCAGGGAAAA | ACTCTTCGCG | AACAGGCACA | GGCGCGTGGT | TATCAGTTGG | 800 |
| TGAGCGATGC | TGCTAGCCTG | AACTCGGTGA | CGGAAGCGAA | TCAGCAAAAA | 850 |
| CCCCTGCTAG | GCCTGTTTGC | TGACGGCAAT | ATGCCAGTGC | GCTGGCTGGG | 900 |
| CCCCAAAGCA | ACTTATCATG | GCAATATCGA | CAAGCCCGCA | GTCACTTGCA | 950 |
| CGCCAAATCC | GCAACGTAAC | GACTCGGTTC | CAACCCTGGC | GCAGATGACC | 1000 |
| GACAAAGCCA | TTGAACTCTT | AAGTAAAAAT | GAGAAAGGCT | TTTTCCTGCA | 1050 |
| AGTTGAAGGT | GCGTCAATCG | ATAAACAGGA | TCATGCTGCG | AATCCTTGTG | 1100 |
| GCCAAATTGG | CGAGACGGTA | GATCTCGATG | AAGCCGTTCA | ACGGGCGCTG | 1150 |
| GAGTTCGCTA | AAAAGGAGGG | TAACACGTTG | GTCATAGTCA | CCGCTGATCA | 1200 |
| CGCCCACGCC | AGCCAGATTG | TTGCTCCGGA | TACCAAAGCT | CCGGGTTTGA | 1250 |
| CCCAGGCGCT | AAATACCAAA | GATGGCGCCG | TGATGGTCAT | GAGTTACGGG | 1300 |
| AACTCCGAAG | AGGATAGCCA | AGAGCACACC | GGCAGTCAGT | GCGTATTGC | 1350 |
| GGCGTATGGC | CCGCATGCCG | CCAATGTTGT | AGGGCTGACC | GACCAGACCG | 1400 |
| ATCTCTTCTA | CACCATGAAA | GCCGCCCTTG | GGCTGAAATA | ATAGCAGGTA | 1450 |

AGCT                                                                                                                    1454

(2) INFORMATION FOR SEQ ID NO:2:

(i) SEQUENCE CHARACTERISTICS:
        (A) LENGTH: 449 amino acid residues
        (B) TYPE: amino acid
        (C) STRANDEDNESS:
        (D) TOPOLOGY: unknown (ii) MOLECULE TYPE: protein (vi) ORIGINAL SOURCE:
        (A) ORGANISM:

(xi) SEQUENCE DESCRIPTION: SEQ ID NO: 2:

```
Thr  Pro  Glu  Met  Pro  Val  Leu  Glu  Asn  Arg  Ala  Ala  Gln  Gly
 1              5                         10

Asp  Ile  Thr  Ala  Pro  Gly  Gly  Ala  Arg  Arg  Leu  Thr  Gly  Asp
 15                  20                         25

Gln  Thr  Ala  Ala  Leu  Arg  Asp  Ser  Leu  Ser  Asp  Lys  Pro  Ala
     30                       35                       40

Lys  Asn  Ile  Ile  Leu  Leu  Ile  Gly  Asp  Gly  Met  Gly  Asp  Ser
               45                       50                       55

Glu  Ile  Thr  Ala  Ala  Arg  Asn  Tyr  Ala  Glu  Gly  Ala  Gly  Gly
                    60                       65                       70

Phe  Phe  Lys  Gly  Ile  Asp  Ala  Leu  Pro  Leu  Thr  Gly  Gln  Tyr
                    75                       80

Thr  His  Tyr  Ala  Leu  Asn  Lys  Lys  Thr  Gly  Lys  Pro  Asp  Tyr
 85                           90                       95

Val  Thr  Asp  Ser  Ala  Ala  Ser  Ala  Thr  Ala  Trp  Ser  Thr  Gly
     100                      105                     110

Val  Lys  Thr  Tyr  Asn  Gly  Ala  Leu  Gly  Val  Asp  Ile  His  Glu
          115                     120                          125

Lys  Asp  His  Pro  Thr  Ile  Leu  Glu  Met  Ala  Lys  Ala  Ala  Gly
               130                     135                          140

Leu  Ala  Thr  Gly  Asn  Val  Ser  Thr  Ala  Glu  Leu  Gln  Asp  Ala
                    145                     150

Thr  Pro  Ala  Ala  Leu  Val  Ala  His  Val  Thr  Ser  Arg  Lys  Cys
 155                      160                     165

Tyr  Gly  Pro  Ser  Ala  Thr  Ser  Glu  Lys  Cys  Pro  Gly  Asn  Ala
     170                      175                     180

Leu  Glu  Lys  Gly  Gly  Lys  Gly  Ser  Ile  Thr  Glu  Gln  Leu  Leu
          185                     190                          195

Asn  Ala  Arg  Ala  Asp  Val  Thr  Leu  Gly  Gly  Gly  Ala  Lys  Thr
               200                     205                          210

Phe  Ala  Glu  Thr  Ala  Thr  Ala  Gly  Glu  Trp  Gln  Gly  Lys  Thr
                    215                     220

Leu  Arg  Glu  Gln  Ala  Gln  Ala  Arg  Gly  Tyr  Gln  Leu  Val  Ser
 225                      230                     235

Asp  Ala  Ala  Ser  Leu  Asn  Ser  Val  Thr  Glu  Ala  Asn  Gln  Gln
     240                      245                     250

Lys  Pro  Leu  Leu  Gly  Leu  Phe  Ala  Asp  Gly  Asn  Met  Pro  Val
          255                     260                          265

Arg  Trp  Leu  Gly  Pro  Lys  Ala  Thr  Tyr  His  Gly  Asn  Ile  Asp
               270                     275                          280

Lys  Pro  Ala  Val  Thr  Cys  Thr  Pro  Asn  Pro  Gln  Arg  Asn  Asp
```

|   |   |   |   |   | 285 |   |   |   |   | 290 |   |   |
|---|---|---|---|---|---|---|---|---|---|---|---|---|
| Ser 295 | Val | Pro | Thr | Leu | Ala 300 | Gln | Met | Thr | Asp | Lys 305 | Ala | Ile | Glu |
| Leu | Leu | Ser 310 | Lys | Asn | Glu | Lys 315 | Gly | Phe | Phe | Leu | Gln 320 | Val | Glu |
| Gly | Ala | Ser 325 | Ile | Asp | Lys | Gln 330 | Asp | His | Ala | Ala | Asn 335 | Pro | Cys |
| Gly | Gln | Ile 340 | Gly | Glu | Thr | Val 345 | Asp | Leu | Asp | Glu | Ala 350 | Val | Gln |
| Arg | Ala | Leu | Glu 355 | Phe | Ala | Lys | Lys 360 | Glu | Gly | Asn | Thr | Leu | Val |
| Ile 365 | Val | Thr | Ala | Asp 370 | His | Ala | His | Ala | Ser 375 | Gln | Ile | Val | Ala |
| Pro 380 | Asp | Thr | Lys | Ala | Pro 385 | Gly | Leu | Thr | Gln | Ala 390 | Leu | Asn | Thr |
| Lys | Asp | Gly 395 | Ala | Val | Met | Val 400 | Met | Ser | Tyr | Gly | Asn 405 | Ser | Glu |
| Glu | Asp | Ser | Gln 410 | Glu | His | Thr | Gly 415 | Ser | Gln | Leu | Arg | Ile 420 | Ala |
| Ala | Tyr | Gly | Pro | His 425 | Ala | Ala | Asn | Val | Val 430 | Gly | Leu | Thr | Asp |
| Gln 435 | Thr | Asp | Leu | Phe | Tyr 440 | Thr | Met | Lys | Ala | Ala 445 | Leu | Gly | Leu |
| Lys 449 |   |   |   |   |   |   |   |   |   |   |   |   |   |

( 2 ) INFORMATION FOR SEQ ID NO:3:

( i ) SEQUENCE CHARACTERISTICS:
        ( A ) LENGTH: 132 nucleotides
        ( B ) TYPE: nucleic acid
        ( C ) STRANDEDNESS: single
        ( D ) TOPOLOGY: linear ( i i ) MOLECULE TYPE:

( v i ) ORIGINAL SOURCE:
        ( A ) ORGANISM:

( x i ) SEQUENCE DESCRIPTION: SEQ ID NO: 3:

| GCGCCGTGAT | GGTCATGAGT | TACGGGAACT | CCGAAGAGAT | CCGTATCCAG | 50 |
| CGTGGTCCGG | GTCGTGCTTT | CGTTACTGAT | AGCCAAGAGC | ACACCGGCAG | 100 |
| TCAGTTGCGT | ATTGCGGCGT | ATGGCCCGCA | TG |  | 132 |

( 2 ) INFORMATION FOR SEQ ID NO:4:

( i ) SEQUENCE CHARACTERISTICS:
        ( A ) LENGTH: 124 nucleotides
        ( B ) TYPE: nucleic acid
        ( C ) STRANDEDNESS: double
        ( D ) TOPOLOGY: linear ( i i ) MOLECULE TYPE:

( v i ) ORIGINAL SOURCE:
        ( A ) ORGANISM:

( x i ) SEQUENCE DESCRIPTION: SEQ ID NO: 4:

| CGGGCCATAC | GCCGCAATAC | GCAACTGACT | GCCGGTGTGC | TCTTGGCTAT | 50 |
| CAGTAACGAA | AGCACGACCC | GGACCACGCT | GGATACGGAT | CTCTTCGGAG | 100 |

TTCCCGTAAC TCATGACCAT CACG 124

( 2 ) INFORMATION FOR SEQ ID NO:5:

( i ) SEQUENCE CHARACTERISTICS:
        ( A ) LENGTH: 57 nucleotides
        ( B ) TYPE: nucleic acid
        ( C ) STRANDEDNESS: double
        ( D ) TOPOLOGY: linear ( i i ) MOLECULE TYPE:

( v i ) ORIGINAL SOURCE:
        ( A ) ORGANISM:

( x i ) SEQUENCE DESCRIPTION: SEQ ID NO: 5:

CTAGTCGCAA AATCCGTATC CAGCGTGGTC CGGGTCGTGC TTTCGTTACT 50

TGCTACG 57

( 2 ) INFORMATION FOR SEQ ID NO:6:

( i ) SEQUENCE CHARACTERISTICS:
        ( A ) LENGTH: 56 nucleotides
        ( B ) TYPE: nucleic acid
        ( C ) STRANDEDNESS: double
        ( D ) TOPOLOGY: linear ( i i ) MOLECULE TYPE:

( v i ) ORIGINAL SOURCE:
        ( A ) ORGANISM:

( x i ) SEQUENCE DESCRIPTION: SEQ ID NO: 6:

GACCGTAGCA AGTAACGAAA GCACGACCCG GACCACGCTG GATACGGATT 50

TTGCGA 56

( 2 ) INFORMATION FOR SEQ ID NO:7:

( i ) SEQUENCE CHARACTERISTICS:
        ( A ) LENGTH: 57 nucleotides
        ( B ) TYPE: nucleic acid
        ( C ) STRANDEDNESS: double
        ( D ) TOPOLOGY: linear ( i i ) MOLECULE TYPE:

( v i ) ORIGINAL SOURCE:
        ( A ) ORGANISM:

( x i ) SEQUENCE DESCRIPTION: SEQ ID NO: 7:

CTAGTCGCAA ATGCATCCGT ATCCAGCGTG GTCCGGGTCG TGCTTTCGTT 50

ACTTACG 57

( 2 ) INFORMATION FOR SEQ ID NO:8:

( i ) SEQUENCE CHARACTERISTICS:
        ( A ) LENGTH: 56 nucleotides
        ( B ) TYPE: nucleic acid
        ( C ) STRANDEDNESS: double
        ( D ) TOPOLOGY: linear ( i i ) MOLECULE TYPE:

( v i ) ORIGINAL SOURCE:
        ( A ) ORGANISM:

( x i ) SEQUENCE DESCRIPTION: SEQ ID NO: 8:

GACCGTAAGT AACGAAAGCA CGACCCGGAC CACGCTGGAT ACGGATGCAT 50

TTGCGA                                                                                                              56

(2) INFORMATION FOR SEQ ID NO:9:

(i) SEQUENCE CHARACTERISTICS:
        (A) LENGTH: 127 nucleotides
        (B) TYPE: nucleic acid
        (C) STRANDEDNESS: double
        (D) TOPOLOGY: linear (ii) MOLECULE TYPE:

(vi) ORIGINAL SOURCE:
        (A) ORGANISM:

(xi) SEQUENCE DESCRIPTION: SEQ ID NO: 9:

CTAGTCGCAA ATGCACTCGT CCGAACAACA ACACCCGTAA ATCTATCCGT           50

ATCCAGCGTG GTCCGGGTCG TGCTTTCGTT ACTATCGGTA AAATCGGTAA          100

CATGCGTCAG GCTCACTGTC CGGGTAA                                   127

(2) INFORMATION FOR SEQ ID NO:10:

(i) SEQUENCE CHARACTERISTICS:
        (A) LENGTH: 127 nucleotides
        (B) TYPE: nucleic acid
        (C) STRANDEDNESS: double
        (D) TOPOLOGY: linear (ii) MOLECULE TYPE:

(vi) ORIGINAL SOURCE:
        (A) ORGANISM:

(xi) SEQUENCE DESCRIPTION: SEQ ID NO: 10:

CGCGTTACCC GGACAGTGAG CCTGACGCAT GTTACCGATT TTACCGATAG           50

TAACGAAAGC ACGACCCGGA CCACGCTGGA TACGGATAGA TTTACGGGTG          100

TTGTTGTTCG GACGAGTGCA TTTGCGA                                   127

(2) INFORMATION FOR SEQ ID NO:11:

(i) SEQUENCE CHARACTERISTICS:
        (A) LENGTH: 85 nucleotides
        (B) TYPE: nucleic acid
        (C) STRANDEDNESS: double
        (D) TOPOLOGY: linear (ii) MOLECULE TYPE:

(vi) ORIGINAL SOURCE:
        (A) ORGANISM:

(xi) SEQUENCE DESCRIPTION: SEQ ID NO: 11:

AACCGGGCAA TACACTCACT ATGCGCTGAA TATCCGTATC CAGCGTGGTC           50

CGGGTCGTGC TTTCGTTACT GGCAAACCGG ACTAC                           85

(2) INFORMATION FOR SEQ ID NO:12:

(i) SEQUENCE CHARACTERISTICS:
        (A) LENGTH: 85 nucleotides
        (B) TYPE: nucleic acid
        (C) STRANDEDNESS: double
        (D) TOPOLOGY: linear (ii) MOLECULE TYPE:

(vi) ORIGINAL SOURCE:
        (A) ORGANISM:

( x i ) SEQUENCE DESCRIPTION: SEQ ID NO: 12:

GTAGTCCGGT TTGCCAGTAA CGAAAGCACG ACCCGGACCA CGCTGGATAC 50

GGATATTCAG CGCATAGTGA GTGTATTGCC CGGTT 85

( 2 ) INFORMATION FOR SEQ ID NO:13:

( i ) SEQUENCE CHARACTERISTICS:
        ( A ) LENGTH: 91 nucleotides
        ( B ) TYPE: nucleic acid
        ( C ) STRANDEDNESS: double
        ( D ) TOPOLOGY: linear ( i i ) MOLECULE TYPE:

( v i ) ORIGINAL SOURCE:
        ( A ) ORGANISM:

( x i ) SEQUENCE DESCRIPTION: SEQ ID NO: 13:

AACCGGGCAA TACACTCACT ATGCGCTGAA TTGCATCCGT ATCCAGCGTG 50

GTCCGGGTCG TGCTTTCGTT ACTTGCGGCA AACCGGACTA C 91

( 2 ) INFORMATION FOR SEQ ID NO:14:

( i ) SEQUENCE CHARACTERISTICS:
        ( A ) LENGTH: 91 nucleotides
        ( B ) TYPE: nucleic acid
        ( C ) STRANDEDNESS: double
        ( D ) TOPOLOGY: linear ( i i ) MOLECULE TYPE:

( v i ) ORIGINAL SOURCE:
        ( A ) ORGANISM:

( x i ) SEQUENCE DESCRIPTION: SEQ ID NO: 14:

GTAGTCCGGT TTGCCGCAAG TAACGAAAGC ACGACCCGGA CCACGCTGGA 50

TACGGATGCA ATTCAGCGCA TAGTGAGTGT ATTGCCCGGT T 91

( 2 ) INFORMATION FOR SEQ ID NO:15:

( i ) SEQUENCE CHARACTERISTICS:
        ( A ) LENGTH: 98 nucleotides
        ( B ) TYPE: nucleic acid
        ( C ) STRANDEDNESS: double
        ( D ) TOPOLOGY: linear ( i i ) MOLECULE TYPE:

( v i ) ORIGINAL SOURCE:
        ( A ) ORGANISM:

( x i ) SEQUENCE DESCRIPTION: SEQ ID NO: 15:

GCGCCGTGAT GGTCATGAGT TACGGGAACT CCGAAGAGTG CACTCGTCCG 50

AACAACAACA CCCGTAAATC TATCCGTATC CAGCGTGGTC CGGGTCGT 98

( 2 ) INFORMATION FOR SEQ ID NO:16:

( i ) SEQUENCE CHARACTERISTICS:
        ( A ) LENGTH: 103 nucleotides
        ( B ) TYPE: nucleic acid
        ( C ) STRANDEDNESS: double
        ( D ) TOPOLOGY: linear ( i i ) MOLECULE TYPE:

( v i ) ORIGINAL SOURCE:
        ( A ) ORGANISM:

( x i ) SEQUENCE DESCRIPTION: SEQ ID NO: 16:

GCTTTCGTTA CTATCGGTAA AATCGGTAAC ATGCGTCAGG CTCACTGTGA    50

TAGCCAAGAG CACACCGGCA GTCAGTTGCG TATTGCGGCG TATGGCCCGC    100

ATG    103

( 2 ) INFORMATION FOR SEQ ID NO:17:

( i ) SEQUENCE CHARACTERISTICS:
        ( A ) LENGTH: 88 nucleotides
        ( B ) TYPE: nucleic acid
        ( C ) STRANDEDNESS: double
        ( D ) TOPOLOGY: linear ( i i ) MOLECULE TYPE:

( v i ) ORIGINAL SOURCE:
        ( A ) ORGANISM:

( x i ) SEQUENCE DESCRIPTION: SEQ ID NO: 17:

CGGACCACGC TGGATACGGA TAGATTTACG GGTGTTGTTG TTCGGACGAG    50

TGCACTCTTC GGAGTTCCCG TAACTCATGA CCATCACG    88

( 2 ) INFORMATION FOR SEQ ID NO:18:

( i ) SEQUENCE CHARACTERISTICS:
        ( A ) LENGTH: 105 nucleotides
        ( B ) TYPE: nucleic acid
        ( C ) STRANDEDNESS: double
        ( D ) TOPOLOGY: linear ( i i ) MOLECULE TYPE:

( v i ) ORIGINAL SOURCE:
        ( A ) ORGANISM:

( x i ) SEQUENCE DESCRIPTION: SEQ ID NO: 18:

CGGGCCATAC GCCGCAATAC GCAACTGACT GCCGGTGTGC TCTTGGCTAT    50

CACAGTGAGC CTGACGCATG TTACCGATTT TACCGATAGT AACGAAAGCA    100

CGACC    105

( 2 ) INFORMATION FOR SEQ ID NO:19:

( i ) SEQUENCE CHARACTERISTICS:
        ( A ) LENGTH: 13 amino acid residues
        ( B ) TYPE: amino acid
        ( C ) STRANDEDNESS:
        ( D ) TOPOLOGY: unknown ( i i ) MOLECULE TYPE: peptide ( v i ) ORIGINAL SOURCE:
        ( A ) ORGANISM:

( x i ) SEQUENCE DESCRIPTION: SEQ ID NO: 19:

Ile Arg Ile Gln Arg Gly Pro Gly Arg Ala Phe Val Thr
1               5                   10              13

( 2 ) INFORMATION FOR SEQ ID NO:20:

( i ) SEQUENCE CHARACTERISTICS:
        ( A ) LENGTH: 13 amino acid residues
        ( B ) TYPE: amino acid
        ( C ) STRANDEDNESS:
        ( D ) TOPOLOGY: unknown ( i i ) MOLECULE TYPE: peptide (v i) ORIGINAL SOURCE:
(A) ORGANISM:

(x i) SEQUENCE DESCRIPTION: SEQ ID NO: 20:

```
Ile  Arg  Ile  Gln  Arg  Gly  Pro  Gly  Arg  Ala  Phe  Val  Thr
1                   5                        10             13
```

(2) INFORMATION FOR SEQ ID NO:21:

(i) SEQUENCE CHARACTERISTICS:
(A) LENGTH: 13 amino acid residues
(B) TYPE: amino acid
(C) STRANDEDNESS:
(D) TOPOLOGY: unknown (i i) MOLECULE TYPE: peptide (v i) ORIGINAL SOURCE:
(A) ORGANISM:

(x i) SEQUENCE DESCRIPTION: SEQ ID NO: 21:

```
Ile  Arg  Ile  Gln  Arg  Gly  Pro  Gly  Arg  Ala  Phe  Val  Thr
1                   5                        10             13
```

(2) INFORMATION FOR SEQ ID NO:22:

(i) SEQUENCE CHARACTERISTICS:
(A) LENGTH: 34 amino acid residues
(B) TYPE: amino acid
(C) STRANDEDNESS:
(D) TOPOLOGY: unknown (i i) MOLECULE TYPE: peptide (v i) ORIGINAL SOURCE:
(A) ORGANISM:

(x i) SEQUENCE DESCRIPTION: SEQ ID NO: 22:

```
Thr  Arg  Pro  Asn  Asn  Asn  Thr  Arg  Lys  Ser  Ile  Arg  Ile  Gln  Arg
1                   5                        10                       15

Gly  Pro  Gly  Arg  Ala  Phe  Val  Thr  Ile  Gly  Lys  Ile  Gly  Asn  Met
               20                   25                       30

Arg  Gln  Ala  His
               34
```

(2) INFORMATION FOR SEQ ID NO:23:

(i) SEQUENCE CHARACTERISTICS:
(A) LENGTH: 13 amino acid residues
(B) TYPE: amino acid
(C) STRANDEDNESS:
(D) TOPOLOGY: unknown (i i) MOLECULE TYPE: peptide (v i) ORIGINAL SOURCE:
(A) ORGANISM:

(x i) SEQUENCE DESCRIPTION: SEQ ID NO: 23:

```
Ile  Arg  Ile  Gln  Arg  Gly  Pro  Gly  Arg  Ala  Phe  Val  Thr
1                   5                        10             13
```

(2) INFORMATION FOR SEQ ID NO:24:

(i) SEQUENCE CHARACTERISTICS:
(A) LENGTH: 15 amino acid residues
(B) TYPE: amino acid
(C) STRANDEDNESS:
(D) TOPOLOGY: unknown ( i i ) MOLECULE TYPE: peptide ( v i ) ORIGINAL SOURCE:
    ( A ) ORGANISM:

( x i ) SEQUENCE DESCRIPTION: SEQ ID NO: 24:

| Cys | Ile | Arg | Ile | Gln | Arg | Gly | Pro | Gly | Arg | Ala | Phe | Val | Thr | Cys |
|---|---|---|---|---|---|---|---|---|---|---|---|---|---|---|
| 1 | | | | 5 | | | | | 10 | | | | | 15 |

( 2 ) INFORMATION FOR SEQ ID NO:25:

( i ) SEQUENCE CHARACTERISTICS:
        ( A ) LENGTH: 36 amino acid residues
        ( B ) TYPE: amino acid
        ( C ) STRANDEDNESS:
        ( D ) TOPOLOGY: unknown ( i i ) MOLECULE TYPE: peptide ( v i ) ORIGINAL SOURCE:
    ( A ) ORGANISM:

( x i ) SEQUENCE DESCRIPTION: SEQ ID NO: 25:

| Cys | Thr | Arg | Pro | Asn | Asn | Asn | Thr | Arg | Lys | Ser | Ile | Arg | Ile | Gln |
|---|---|---|---|---|---|---|---|---|---|---|---|---|---|---|
| 1 | | | | 5 | | | | | 10 | | | | | 15 |
| Arg | Gly | Pro | Gly | Arg | Ala | Phe | Val | Thr | Ile | Gly | Lys | Ile | Gly | Asn |
| | | | 20 | | | | | 25 | | | | | 30 | |
| Met | Arg | Gln | Ala | His | Cys | | | | | | | | | |
| | | | 35 | | 36 | | | | | | | | | |

( 2 ) INFORMATION FOR SEQ ID NO:26:

( i ) SEQUENCE CHARACTERISTICS:
        ( A ) LENGTH: 1455 nucleotides
        ( B ) TYPE: nucleic acid
        ( C ) STRANDEDNESS: double
        ( D ) TOPOLOGY: linear ( i i ) MOLECULE TYPE:

( v i ) ORIGINAL SOURCE:
    ( A ) ORGANISM:

( x i ) SEQUENCE DESCRIPTION: SEQ ID NO: 26:

```
GG  ATC CTT GTA CAT GGA GAA AAT AAA GTG AAA CAG TCG ACT ATT         44
GCA CTG GCA CTC TTA CCG TTA CTG TTT ACC CCT GTG ACA AAA GCC         89
CGT ACA CCA GAA ATG CCT GTT CTC GAA AAC CGG GCT GCT CAG GGC        134
GAT ATT ACT GCA CCC GGG GGT GCG CGC CGT TTA ACG GGT GAC CAG        179
ACT GCA GCT CTG CGC GAT TCT CTT AGC GAT AAA CCG GCA AAA AAT        224
ATT ATT TTG CTG ATT GGC GAT GGT ATG GGG GAC TCG GAA ATT ACC        269
GCG GCA CGT AAC TAT GCC GAA GGT GCG GGC GGC TTT TTT AAA GGT        314
ATA GAT GCC TTA CCG TTA ACC GGG CAA TAC ACT CAC TAT GCG CTG        359
AAT AAA AAA ACC GGC AAA CCG GAC TAC GTA ACC GAC TCG GCT GCA        404
TCA GCA ACC GCC TGG TCA ACC GGT GTC AAA ACC TAT AAC GGC GCG        449
CTG GGC GTC GAT ATC CAC GAA AAA GAT CAC CCA ACG ATC CTG GAA        494
ATG GCA AAA GCA GCT GGT CTG GCG ACC GGT AAC GTT TCT ACC GCA        539
GAG TTG CAG GAC GCC ACA CCC GCT GCG CTG GTG GCA CAT GTG ACT        584
AGT CGC AAA TGC TAC GGT CCG AGC GCG ACC AGT GAA AAA TGT CCG        629
```

| | | | | | | | | | | | | | | |
|---|---|---|---|---|---|---|---|---|---|---|---|---|---|---|
| GGT | AAC | GCG | TTG | GAA | AAA | GGC | GGA | AAA | GGA | TCT | ATT | ACC | GAA | CAG | 674 |
| TTG | CTG | AAT | GCT | CGT | GCC | GAC | GTT | ACG | CTT | GGC | GGC | GGC | GCA | AAA | 719 |
| ACC | TTT | GCT | GAA | ACG | GCA | ACC | GCC | GGC | GAA | TGG | CAG | GGA | AAA | ACT | 764 |
| CTT | CGC | GAA | CAG | GCA | CAG | GCG | CGT | GGT | TAT | CAG | TTG | GTG | AGC | GAT | 809 |
| GCT | GCT | AGC | CTG | AAC | TCG | GTG | ACG | GAA | GCG | AAT | CAG | CAA | AAA | CCC | 854 |
| CTG | CTA | GGC | CTG | TTT | GCT | GAC | GGC | AAT | ATG | CCA | GTG | CGC | TGG | CTG | 899 |
| GGC | CCC | AAA | GCA | ACT | TAT | CAT | GGC | AAT | ATC | GAC | AAG | CCC | GCA | GTC | 944 |
| ACT | TGC | ACG | CCA | AAT | CCG | CAA | CGT | AAC | GAC | TCG | GTT | CCA | ACC | CTG | 989 |
| GCG | CAG | ATG | ACC | GAC | AAA | GCC | ATT | GAA | CTC | TTA | AGT | AAA | AAT | GAG | 1034 |
| AAA | GGC | TTT | TTC | CTG | CAA | GTT | GAA | GGT | GCG | TCA | ATC | GAT | AAA | CAG | 1079 |
| GAT | CAT | GCT | GCG | AAT | CCT | TGT | GGC | CAA | ATT | GGC | GAG | ACG | GTA | GAT | 1124 |
| CTC | GAT | GAA | GCC | GTT | CAA | CGG | GCG | CTG | GAG | TTC | GCT | AAA | AAG | GAG | 1169 |
| GGT | AAC | ACG | TTG | GTC | ATA | GTC | ACC | GCT | GAT | CAC | GCC | CAC | GCC | AGC | 1214 |
| CAG | ATT | GTT | GCT | CCG | GAT | ACC | AAA | GCT | CCG | GGT | TTG | ACC | CAG | GCG | 1259 |
| CTA | AAT | ACC | AAA | GAT | GGC | GCC | GTG | ATG | GTC | ATG | AGT | TAC | GGG | AAC | 1304 |
| TCC | GAA | GAG | GAT | AGC | CAA | GAG | CAC | ACC | GGC | AGT | CAG | TTG | CGT | ATT | 1349 |
| GCG | GCG | TAT | GGC | CCG | CAT | GCC | GCC | AAT | GTT | GTA | GGG | CTG | ACC | GAC | 1394 |
| CAG | ACC | GAT | CTC | TTC | TAC | ACC | ATG | AAA | GCC | GCC | CTT | GGG | CTG | AAA | 1439 |
| TAA | TAG | CAG | GTA | AGC | T | | | | | | | | | | 1455 |

( 2 ) INFORMATION FOR SEQ ID NO:27:

( i ) SEQUENCE CHARACTERISTICS:
        ( A ) LENGTH: 23 amino acid residues
        ( B ) TYPE: amino acid
        ( C ) STRANDEDNESS:
        ( D ) TOPOLOGY: unknown ( i i ) MOLECULE TYPE: peptide ( v i ) ORIGINAL SOURCE:
        ( A ) ORGANISM:

( x i ) SEQUENCE DESCRIPTION: SEQ ID NO: 27:

Thr Arg Pro Asn Asn Asn Thr Arg Lys Ser Ile Arg Ile Gln Arg
1               5                   10                  15
Gly Pro Gly Arg Ala Phe Val Thr
            20              23

( 2 ) INFORMATION FOR SEQ ID NO:28:

( i ) SEQUENCE CHARACTERISTICS:
        ( A ) LENGTH: 16 amino acid residues
        ( B ) TYPE: amino acid
        ( C ) STRANDEDNESS:
        ( D ) TOPOLOGY: unknown ( i i ) MOLECULE TYPE: peptide ( v i ) ORIGINAL SOURCE:
        ( A ) ORGANISM:

( x i ) SEQUENCE DESCRIPTION: SEQ ID NO: 28:

Ile Arg Ile Gln Arg Gly Pro Gly Arg Ala Phe Val Thr Ile Gly
1               5                   10                  15
Lys

16

( 2 ) INFORMATION FOR SEQ ID NO:29:

( i ) SEQUENCE CHARACTERISTICS:
        ( A ) LENGTH: 39 amino acid residues
        ( B ) TYPE: amino acid
        ( C ) STRANDEDNESS:
        ( D ) TOPOLOGY: unknown ( i i ) MOLECULE TYPE: peptide ( v i ) ORIGINAL SOURCE:
        ( A ) ORGANISM:

( x i ) SEQUENCE DESCRIPTION: SEQ ID NO: 29:

```
Asp Pro Arg Phe Gln Asp Ser Ser Ser Lys Ala Pro Pro Pro
1               5                   10                 15

Ser Leu Pro Ser Pro Ser Arg Leu Pro Gly Pro Ser Asp Thr Pro
            20              25                  30

Ile Leu Pro Gln Lys Lys Lys Lys Lys
            35              39
```

( 2 ) INFORMATION FOR SEQ ID NO:30:

( i ) SEQUENCE CHARACTERISTICS:
        ( A ) LENGTH: 9 amino acid residues
        ( B ) TYPE: amino acid
        ( C ) STRANDEDNESS:
        ( D ) TOPOLOGY: unknown ( i i ) MOLECULE TYPE: peptide ( v i ) ORIGINAL SOURCE:
        ( A ) ORGANISM:

( x i ) SEQUENCE DESCRIPTION: SEQ ID NO: 30:

```
Lys Pro Asp Glu Asp Asp Trp Glu Ser
1               5               9
```

( 2 ) INFORMATION FOR SEQ ID NO:31:

( i ) SEQUENCE CHARACTERISTICS:
        ( A ) LENGTH: 471 amino acid residues
        ( B ) TYPE: amino acid
        ( C ) STRANDEDNESS:
        ( D ) TOPOLOGY: unknown ( i i ) MOLECULE TYPE: protein ( v i ) ORIGINAL SOURCE:
        ( A ) ORGANISM:

( x i ) SEQUENCE DESCRIPTION: SEQ ID NO: 31:

```
            Val Lys Gln Ser Thr Ile Ala Leu Ala Leu Leu Pro Leu
                -20             -15                 -10

Leu Phe Thr Pro Val Thr Lys Ala Arg Thr Pro Glu Met Pro Val
            -5                   1                   5

Leu Glu Asn Arg Ala Ala Gln Gly Asp Ile Thr Ala Pro Gly Gly
            10                  15                  20

Ala Arg Arg Leu Thr Gly Asp Gln Thr Ala Ala Leu Arg Asp Ser
            25                  30                  35

Leu Ser Asp Lys Pro Ala Lys Asn Ile Ile Leu Leu Ile Gly Asp
            40                  45                  50

Gly Met Gly Asp Ser Glu Ile Thr Ala Ala Arg Asn Tyr Ala Glu
            55                  60                  65
```

```
Gly Ala Gly Gly Phe Phe Lys Gly Ile Asp Ala Leu Pro Leu Thr
         70                  75                  80
Gly Gln Tyr Thr His Tyr Ala Leu Asn Lys Lys Thr Gly Lys Pro
         85                  90                  95
Asp Tyr Val Thr Asp Ser Ala Ala Ser Ala Thr Ala Trp Ser Thr
        100                 105                 110
Gly Val Lys Thr Tyr Asn Gly Ala Leu Gly Val Asp Ile His Glu
        115                 120                 125
Lys Asp His Pro Thr Ile Leu Glu Met Ala Lys Ala Ala Gly Leu
        130                 135                 140
Ala Thr Gly Asn Val Ser Thr Ala Glu Leu Gln Asp Ala Thr Pro
        145                 150                 155
Ala Ala Leu Val Ala His Val Thr Ser Arg Lys Cys Tyr Gly Pro
        160                 165                 170
Ser Ala Thr Ser Glu Lys Cys Pro Gly Asn Ala Leu Glu Lys Gly
        175                 180                 185
Gly Lys Gly Ser Ile Thr Glu Gln Leu Leu Asn Ala Arg Ala Asp
        190                 195                 200
Val Thr Leu Gly Gly Gly Ala Lys Thr Phe Ala Glu Thr Ala Thr
        205                 210                 215
Ala Gly Glu Trp Gln Gly Lys Thr Leu Arg Glu Gln Ala Gln Ala
        220                 225                 230
Arg Gly Tyr Gln Leu Val Ser Asp Ala Ala Ser Leu Asn Ser Val
        235                 240                 245
Thr Glu Ala Asn Gln Gln Lys Pro Leu Leu Gly Leu Phe Ala Asp
        250                 255                 260
Gly Asn Met Pro Val Arg Trp Leu Gly Pro Lys Ala Thr Tyr His
        265                 270                 275
Gly Asn Ile Asp Lys Pro Ala Val Thr Cys Thr Pro Asn Pro Gln
        280                 285                 290
Arg Asn Asp Ser Val Pro Thr Leu Ala Gln Met Thr Asp Lys Ala
        295                 300                 305
Ile Glu Leu Leu Ser Lys Asn Glu Lys Gly Phe Phe Leu Gln Val
        310                 315                 320
Glu Gly Ala Ser Ile Asp Lys Gln Asp His Ala Ala Asn Pro Cys
        325                 330                 335
Gly Gln Ile Gly Glu Thr Val Asp Leu Asp Glu Ala Val Gln Arg
        340                 345                 350
Ala Leu Glu Phe Ala Lys Lys Glu Gly Asn Thr Leu Val Ile Val
        355                 360                 365
Thr Ala Asp His Ala His Ala Ser Gln Ile Val Ala Pro Asp Thr
        370                 375                 380
Lys Ala Pro Gly Leu Thr Gln Ala Leu Asn Thr Lys Asp Gly Ala
        385                 390                 395
Val Met Val Met Ser Tyr Gly Asn Ser Glu Glu Asp Ser Gln Glu
        400                 405                 410
His Thr Gly Ser Gln Leu Arg Ile Ala Ala Tyr Gly Pro His Ala
        415                 420                 425
Ala Asn Val Val Gly Leu Thr Asp Gln Thr Asp Leu Phe Tyr Thr
        430                 435                 440
Met Lys Ala Ala Leu Gly Leu Lys
        445                 449
```

(2) INFORMATION FOR SEQ ID NO:32:

(i) SEQUENCE CHARACTERISTICS:
 (A) LENGTH: 53 nucleotides
 (B) TYPE: nucleic acid
 (C) STRANDEDNESS: single
 (D) TOPOLOGY: linear (ii) MOLECULE TYPE:

(vi) ORIGINAL SOURCE:
 (A) ORGANISM:

(xi) SEQUENCE DESCRIPTION: SEQ ID NO: 32:

CTAGTCGCTG CTGCTAGCGT CCGAGACGCG ACCAGTGAAA AATGTCCGGG    50

TAA    53

(2) INFORMATION FOR SEQ ID NO:33:

(i) SEQUENCE CHARACTERISTICS:
 (A) LENGTH: 53 nucleotides
 (B) TYPE: nucleic acid
 (C) STRANDEDNESS: single
 (D) TOPOLOGY: linear (ii) MOLECULE TYPE:

(vi) ORIGINAL SOURCE:
 (A) ORGANISM:

(xi) SEQUENCE DESCRIPTION: SEQ ID NO: 33:

CGCGTTACCC GGACATTTTT CACATGGTCG CGCTCGGACC GTAGCAGCAG    50

CGA    53

(2) INFORMATION FOR SEQ ID NO:34:

(i) SEQUENCE CHARACTERISTICS:
 (A) LENGTH: 31 nucleotides
 (B) TYPE: nucleic acid
 (C) STRANDEDNESS: single
 (D) TOPOLOGY: linear (ii) MOLECULE TYPE:

(vi) ORIGINAL SOURCE:
 (A) ORGANISM:

(xi) SEQUENCE DESCRIPTION: SEQ ID NO: 34:

GTGCTCTTGG CTATCGCATT CGGAGTTCCC G    31

GENETICALLY ENGINEERED ENZYMES AND THEIR CONJUGATES FOR DIAGNOSTIC ASSAYS

This application is a continuation of prior application Ser. No. 08/100,708, filed Jul. 29, 1993, now abandoned, which is a continuation-in-part application of U.S. patent application Ser. No. 08/031,165, now abandoned, of E. M. Brate et al., filed Mar. 9, 1993, entitled "Genetically Engineered Enzymes And Their Conjugates For Diagnostic Assays."

BACKGROUND OF THE INVENTION

Alkaline phosphatase (AP) is an enzyme having several advantages that make it suitable for protein engineering. For example, a synthetic AP gene known as "phoA" was constructed which maintains the wildtype protein sequence (Chang, C. N., Kuang. W. J., and Chen, E. Y. (1986) Gene 44, 121–125) yet has unique restriction sites designed into the DNA sequence (Mandecki, W., Shallcross, M. A., Sowadski, J., and Tomazic-Allen, S. (1991) Protein Engineering 4, 801–804). A high level of AP is expressed from the synthetic phoA gene. Expression was done in *Escherichia coli* (*E. coli*) with high copy plasmids under the control of the lac promoter (Mandecki, W., Shallcross, M. A., Sowadski, J., and Tomazic-Allen, S. (1991) Protein Engineering 4, 801–804). The crystal structure of the homodimeric protein has been determined by X-ray diffraction (Sowadski, J. M., Handschumacher, M. D., Murthy, H. M. K., Foster, B. A., and Wyckoff, H. W. (1985) J. Mol. Biol. 186, 417–433; Kim, E. E. and Wyckoff, H. W. (1991) J. Mol. Biol. 218, 449–464). The structure provides information on the location of surface loops, the structural flexibility and solvent accessibility of regions of the protein, and distance of amino acid (a.a) residues from the catalytic active site. Generally, point mutations in close proximity to the active site do not destroy AP activity and in some cases increase the catalytic rate (Butler-Ransohoff, J. E., Kendall, D. A., and Kaiser, E. T. (1988) Proc. Natl. Acad. Sci. USA 85, 4276–4278; Chaidaroglou, A. and Kantrowitz, E. R. (1989) Protein Engineering 3, 127–132; Mandecki, W., Shallcross, M. A., Sowadski, J., and Tomazic-Allen, S. (1991) Protein Engineering 4, 801–804). Finally, AP has high catalytic activity and low substrate specificity. The region around the active site accommodates a wide variety of different molecules and the enzyme recognizes and binds only the phosphate portion of the substrate (Sowadski, J. M., Handschumacher, M. D., Murthy, H. M. K., Foster, B. A., and Wyckoff, H. W. (1985) J. Mol. Biol. 186, 417–433).

Insertion of peptides into internal regions of AP have been described to demonstrate surface flexibility and mutability of AP (Freimuth, P. I., Taylor, J. W., and Kaiser, E. T. (1990) J. Biol. Chem. 265, 896–901) for use as a vehicle to express high levels of peptide hormones (Freimuth, P. I., Taylor, J. W., and Kaiser, E. T. (1990) J. Biol. Chem. 265, 896–901; Langen, H. T. and Taylor, J. W. (1992) Proteins: Structure, Function, and Genetics 14, 1–9), to examine the effect of protein context on antigen presentation (Freimuth, P. and Steinman, R. M. (1990) Res. Microbiol. 141, 995–1001), and to express a snake neurotoxin that binds its receptor for use in enzymo-immuno and enzymo-receptor assays (Gillet, D., Ducancel, F., Pradel, E., Lonetti, M., Mnez, A., and Boulain, J.-C. (1992) Protein Engineering 5, 273–278).

Insertion of a 15 a.a. hormone peptide, dynorphin, was tolerated between a.a. 166–167 and 190–191 (Freimuth, P. I., Taylor, J. W., and Kaiser, E. T. (1990) J. Biol. Chem. 265, 896–901) and 11 and 19 a.a. peptides containing somatostatin-14 replaced a.a. 92–94 in AP without significantly affecting enzymatic activity (Langen, H. T. and Taylor, J. W. (1992) Proteins: Structure, Function, and Genetics 14, 1–9). AP-somatostatin recombinant proteins are bound by anti-somatostatin polyclonal antibodies as well as somatostatin receptor showing that the peptides are surface exposed in the native conformation of the recombinant protein. A 62 a.a. snake neurotoxin, erabutoxin, was inserted between a.a. 6 and 7 in AP. In the fusion protein, the AP activity is retained and the neurotoxin retains its biological function of binding to the nicotine acetylcholine receptor (Gillet, D., Ducancel, F., Pradel, E., Lonetti, M., Mnez, A., and Boulain, J.-C. (1992) Protein Engineering 5, 273–278).

AP is commonly used as an enzymatic detection reagent in diagnostic assays, particularly specific binding assay formats. Generally, such specific binding assay formats depend upon the ability of a first binding molecule of a binding molecule pair to specifically bind to a second binding molecule of a binding molecule pair wherein a conjugate, comprising one of such binding molecules labeled with an enzyme, is employed to determine the extent of such binding. For example, where such binding molecule pairs are an analyte and an antibody to such analyte, the extent of binding is determined by the amount of the enzyme present in the conjugate, which either has or has not participated in a binding reaction with the analyte, wherein the amount of the enzyme detected and measured can be correlated to the amount of analyte present in the test sample.

Conjugation of a ligand to a molecule is traditionally achieved according to methods known in the art, however, such methods are non-specific in that the location, orientation, and number of attachments of the desired molecule to the ligand cannot be precisely controlled. If the molecule is an enzyme, such non-specific conjugation of a ligand can impair the desirable intrinsic enzymatic activity and in the case of specific binding assays, if the conjugation occurs at a site too far away from the active site of the enzyme, binding of the binding molecule will lead to inefficient or minimal modulation of the conjugate formed, thus resulting in assays with poor dynamic range and high background signal.

SUMMARY OF THE INVENTION

The present invention is directed to genetically engineered proteins, such as hybrid enzymes and the preparation and use thereof in qualitative and quantitative assays. Examples of such hybrid enzymes are AP-epitope and hybrid enzyme-ligand conjugates. The present invention also provides DNA sequences encoding hybrid enzymes. These hybrid enzymes have novel properties and enable a novel approach for both the qualitative and quantitative assays for an analyte.

A hybrid enzyme according to one embodiment of the present invention is provided comprising a starting enzyme, a foreign a.a. moiety which either replaces or is inserted into an a.a. sequence in a starting enzyme. The foreign a.a. moiety which replaces or is inserted into an a.a. sequence of the starting enzyme occurs at a region close to an active site of the starting enzyme to give the hybrid enzyme, wherein the enzymatic activity of the starting enzyme can be modified. The foreign a.a. moiety can still be bound by a binding molecule and such binding can modify or modulate the activity of the hybrid enzyme.

According to another embodiment of the present invention, the hybrid enzyme comprises a starting enzyme in which a foreign a.a. moiety has been introduced by replacement of or insertion into an a.a. sequence of the starting enzyme near the active site. The foreign a.a. moiety on the hybrid enzyme serves as a point of attachment for coupling or conjugation of a ligand. When conjugated to the enzyme, the conjugated ligand can be bound by a binding molecule and the enzymatic activity of the hybrid enzyme can be modified.

According to another embodiment of the present invention, a method of using such hybrid enzymes in qualitative or quantitative assays is provided. In particular, the method of the present invention comprises the steps of: (1) contacting a test sample containing the analyte, the hybrid enzyme of the present invention and a binding molecule of the analyte to form a reaction mixture therewith; (2) contacting the reaction mixture with a substrate for the starting enzyme; and (3) monitoring the change, dependent upon the type or amount of analyte present in the reaction mixture, in enzymatic activity of the hybrid enzyme. The reaction mixture can be allowed to reach a steady state or equilibrium before conducting step (2); and step (1) can be performed sequentially or simultaneously.

According to the present invention, the changes in the enzymatic activity are dependent upon the presence or the amount of the analyte in the test sample. Thus, the hybrid enzyme provides a basis for assays to detect, (1) the presence or the amount of an antibody directly or (2) the presence or the amount of an antigen indirectly by competition for binding to the binding molecule.

BRIEF DESCRIPTION OF FIGURES

FIGS. 2A–2C shows DNA sequence of synthetic phoA gene with unique restriction sites that were used in the constructions.

FIGS. 2D and 2E show the a.a. sequence of the mature AP.

FIG. 3 shows nucleotide sequences of oligodeoxyribonucleotides used for construction of pAPI (plasmids which code for the AP-epitopes).

FIG. 4 shows a.a. sequences of AP-epitopes in the region of epitope insertion or replacement.

FIG. 15 shows a.a. sequence of AP and the hybrid enzyme (cysteine mutants) in which the native residue (underlined) is replaced by cysteine.

FIG. 18A shows the effect of sheep polyclonal antibodies.

DETAILED DESCRIPTION OF THE INVENTION

Figure 1:
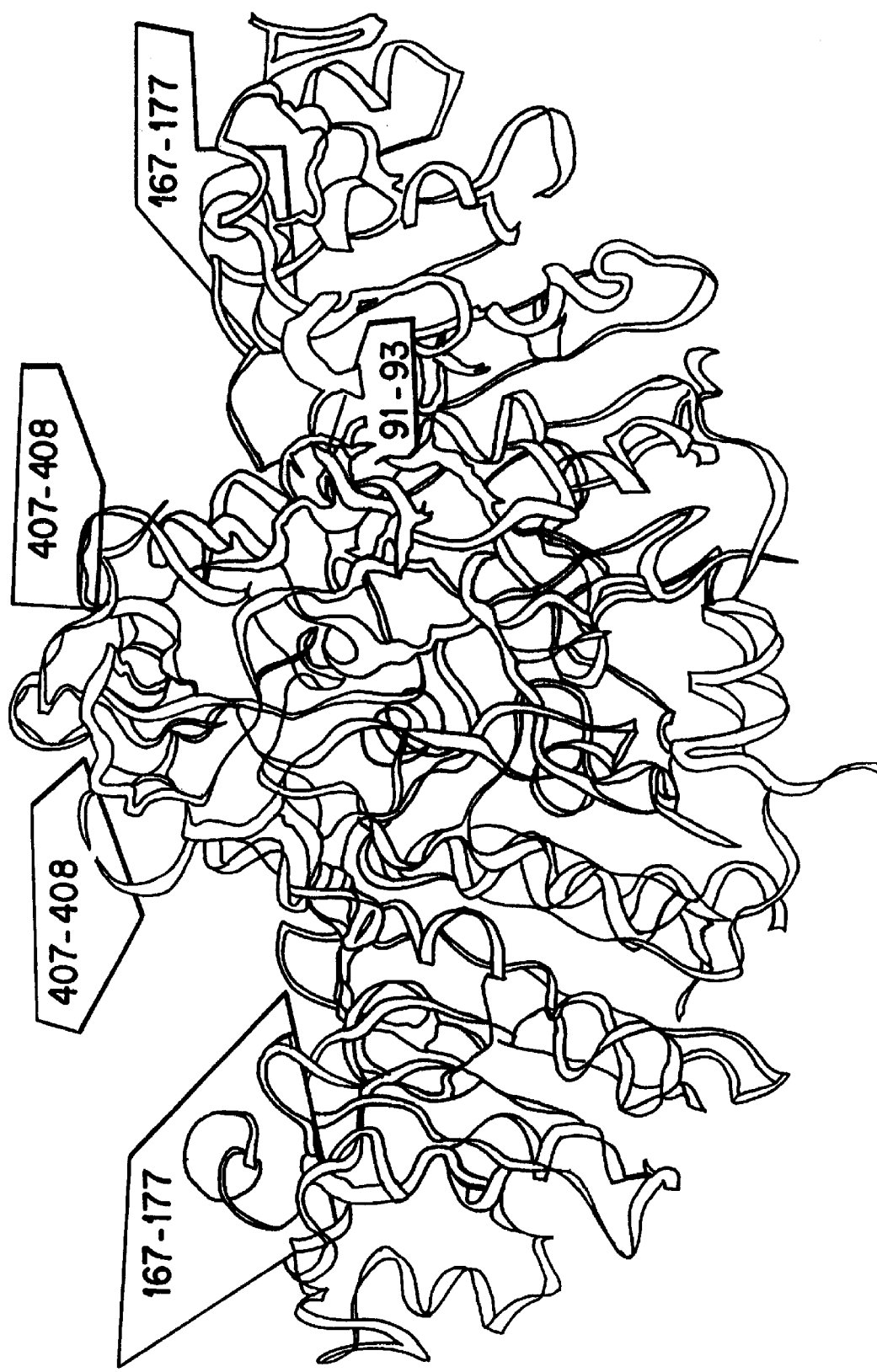
FIG. 1 is a drawing of the 3-dimensional structure of AP with the regions chosen for modifications labeled.
Figure 5A:
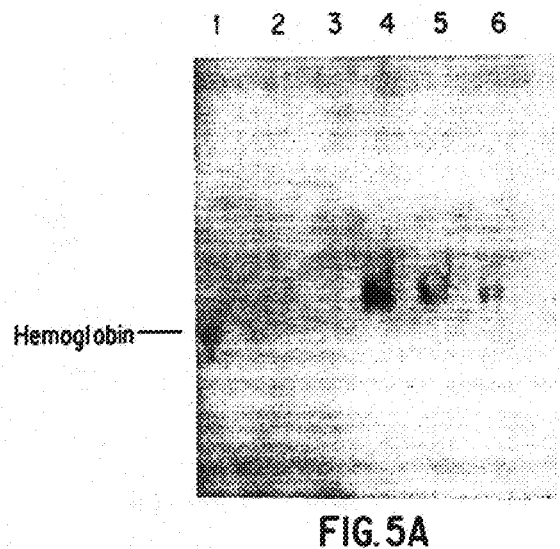
FIG. 5 shows Western blots of purified AP-epitopes. Primary antibody was anti-gp120 MAb and secondary antibody was horseradish peroxidase-labelled goat anti-mouse IgG: a.) Native gel: lane 1, hemoglobin protein marker; lane 2, blank; lane 3, AP (1 mg); lane 4, API1 (1 mg); lane 5, API6 (1 mg); lane 6, API7 (1 mg). b.) SDS gel: lane 1, molecular weight markers; lane 2, AP (0.2 mg); lane 3, API1 (0.2 mg); lane 4, API6 (0.2 mg); lane 5, API7 (0.2 mg); lane 6, blank.
Figure 5B:
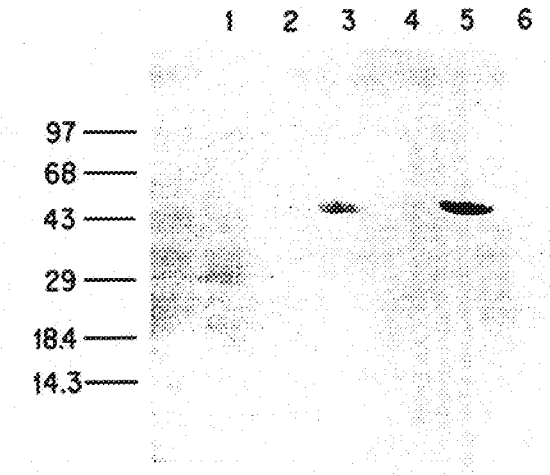

Abbreviations used are given below:

Nucleotides:

| | |
|---|---|
| A | adenosine |
| C | cytosine |
| G | guanine |
| T | thymine |

Amino acids:

| | |
|---|---|
| Ala A | alanine |
| Arg R | arginine |
| Asn N | asparagine |
| Asp D | aspartic acid |
| Cys C | cysteine |
| Gln Q | glutamine |
| Glu E | glutamic acid |
| Gly G | glycine |
| His H | histidine |
| Ile I | isoleucine |
| Leu L | leucine |
| Lys K | lysine |
| Met M | methionine |
| Phe F | phenylalanine |
| Pro P | proline |
| Ser S | serine |
| Thr T | threonine |
| Trp W | trytophan |
| Tyr Y | tyrosine |
| Val V | valine |
| a.a. | amino acid(s) |
| AP | alkaline phosphatase |
| ATP | adenosine triphosphate |
| BSA | bovine serum albumin |
| BCIP | 5-bromo-4-chloro-3-indolyl phosphate |
| DMFDP | dimethyl-fluorescein diphosphate |
| DMSO | dimethyl sulfoxide |
| DTT | dithiothreitol |
| EDTA | ethylenediaminetetraacetic acid |
| FDP | fluorescein diphosphate |
| HPLC | high performance liquid chromatography |
| IPTG | isopropyl D-thiogalactopyranoside |
| MAb | monoclonal antibody |
| MUP | 4-methylumbelliferyl phosphate |
| PNPP | p-nitrophenyl phosphate |
| SDS | sodium dodecyl sulfate |
| X-gal | 5-bromo-4-chloro-3-indolyl beta-D-galactopyranoside |

The present invention is generally applicable to proteins, and more specifically directed to genetically engineered proteins, e.g., enzymes, and their use thereof in qualitative and quantitative assays. Examples of proteins other than enzymes are heme proteins, carrier and receptor proteins. Any protein that can be genetically engineered to accept an inserted or replacement foreign amino acid moiety and the subsequent binding of a binding molecule to affect changes of the genetically engineered protein can be utilized.

According to the present invention, enzymes of preferably high protein stability and high catalytic activity can be used as the "starting" enzymes for their modification into hybrid enzymes. Starting enzymes can be natural enzymes, enzymatically-active fragments of the natural enzymes, or genetically engineered enzymes. Starting enzymes can be in the form of polypeptides, ribozymes, or catalytic antibodies. Starting enzymes include, but are not intended to be limited to: adenosine deaminase; alkaline phosphatase, alpha-amylase; bacterial luciferase; beta-galactosidase; beta-galactosidase fragment; beta-lactamase; carbonic anhydrase; catalase; firefly luciferase; glucose oxidase; glucose-6-phosphate dehydrogenase; glucosidase; hexokinase; horseradish peroxidase; invertase; isocitrate dehydrogenase; lysozyme; malate dehydrogenase; microperoxidase; 6-phosphofructase; phosphoglucomutase; phospholipase C; pyruvate kinase; urease; and xanthine oxidase, and the like.

The term "active site" as used herein means that part of an enzyme which binds a specific substrate and converts it to product catalytically or otherwise. The active site of an enzyme consists of the catalytic center and the substrate-binding site. The active site may lie on the surface as in chymotrypsin or in a cleft as in lysozyme, papain, carbonic anhydrase or ribonuclease, in the enzyme molecule. The active site usually involves only a limited number of a.a. residues. Preferably, the foreign a.a. moiety does not replace an a.a. sequence or insert into an a.a. sequence of the starting enzyme at a location that is involved in the catalytic mechanism of the active site. The foreign a.a. moiety generally replaces or inserts into an a.a. sequence at a location that is from about 1 to about 50 angstroms, preferably from about 2 to about 25 angstroms, and most preferably from about 3 to 15 angstroms away from the center of the active site. Locations and residues which are in loops and located on the surface of the protein are good locations for a.a. sequences of the starting protein to be replaced by, or insertion of, a foreign a.a. moiety. Additionally, if the active site is in a cavity of the starting enzyme, the area surrounding the cavity is a good location for a.a. sequences of the starting protein to be replaced by, or insertion of, a foreign a.a. moiety. For an enzyme, it is also possible to select the "allosteric site" for such an insertion or replacement foreign a.a. moiety. The allosteric site can bind a molecule such that the binding event at that site modulates the enzymatic activity of the enzyme.

"Analyte," as used herein, is the substance to be detected in the test sample using the present invention. An analyte can be any substance for which there exists a naturally occurring binding molecule (e.g., an antibody) or for which a binding molecule can be prepared, and the analyte can bind to one or more binding molecules in an assay. Analyte thus includes antigenic substances, haptens, antibodies, and combinations thereof. Thus an analyte can be a protein, a peptide, an a.a., a carbohydrate, a hormone, a steroid, a vitamin, a lipid, a nucleic acid, a peptide, a trace element, a drug including those administered for therapeutic purposes as well as those administered for illicit purposes, a bacterium, a virus, and a metabolite of or an antibody to any of the above substances.

"Binding molecule" as used herein, is a member of a binding molecule pair, i.e., two different molecules where one of the molecules, through chemical or physical means, specifically binds to the second molecule. In addition to antigen and antibody binding molecules, other binding molecules include biotin and avidin, carbohydrates and lectins, complementary nucleotide sequences (including probe and captured nucleic acid sequences used in DNA hybridization assays to detect a nucleic acid sequence), effector and receptor molecules, enzyme cofactors and enzymes, enzyme inhibitors and enzymes, and the like. Furthermore, binding molecules can include members that are analogs of the original binding molecule. For example, a derivative or fragment of the analyte, e.g., an analyte-analog can be used which has at least one epitope or binding site in common with the analyte. Immunoreactive binding molecules include antigens, haptens, antibodies, and complexes thereof including those formed by recombinant DNA methods or peptide synthesis.

"Conjugation," as used herein, is the chemical coupling of one moiety to another to form a conjugate. Coupling agents covalent conjugation to protein have been described in U.S. Pat. No. 5,053,520, the entirety of which is hereby incorporated by reference. Homobifunctional agents for coupling enzymes to antibodies are also known in the art as described in P.C.T. Publication Number WO 92/07268, published on Apr. 30, 1992.

"Foreign a.a. moiety" as used herein means one or more amino acids or a peptide comprising an a.a. sequence. The peptide can also be a polypeptide, an epitope, or a structure that can mimic an epitope. When the foreign a.a. moiety replaces or is inserted into an a.a. sequence of a starting protein to give the resultant genetically engineered protein, the foreign a.a. moiety can form either a binding surface for an analyte or a site for the conjugation of a ligand. Enzymes are one example of genetically engineered proteins. The foreign a.a. moiety replaces or is inserted into an a.a. sequence of a starting enzyme to give the resultant hybrid enzyme. The foreign a.a. moiety can affect the enzymatic activity of the hybrid enzyme in three ways. First, the foreign a.a. moiety replaces or is inserted into an a.a. sequence of the starting enzyme and may not appreciably affect the enzymatic activity of the hybrid enzyme. Binding of the analyte to the hybrid enzyme reduces the enzymatic activity of the hybrid enzyme. Second, the foreign a.a. moiety replaces or is inserted into an a.a. sequence of the starting enzyme and may not appreciably affect the enzymatic activity of the hybrid enzyme. Binding of the analyte to the hybrid enzyme enhances the enzymatic activity of the hybrid enzyme. Third, the foreign a.a. moiety replaces or is inserted into an a.a. sequence of the starting enzyme and may appreciably affect the enzymatic activity of the hybrid enzyme. Binding of the analyte to the hybrid enzyme enhances the enzymatic activity of the hybrid enzyme.

"Hybrid enzyme," as used herein, is the product of a foreign a.a. moiety replacing or inserted into an a.a. sequence of a starting enzyme. The foreign a.a. moiety can be one or more amino acids or a peptide comprising an a.a. sequence. The foreign a.a. moiety can mimic an epitope or be a site for conjugation of a ligand.

"Ligand" is defined as a chemical group or molecule capable of being bound or conjugated to another chemical group or molecule. Ligands are molecular species that are capable of competing against or inhibiting the binding of the analyte. Such a ligand can be a small molecule or a macromolecule. Examples of ligands include theophylline, antibiotics, peptides, proteins, carbohydrates, lipids and nucleic acids. Preferably, smaller molecular weight oligopeptides which represent or mimic the epitopes of the analytes are used. The ligands are covalently attached to the foreign a.a. moiety which has been inserted into or has replaced an a.a. sequence in the starting enzyme via chemical linkers. Hetero- or homo- bifunctional, or photoreactive linkers can be used. Examples of linkers include carbodiimide, glutaraldehyde, haloformate, iodoacetamide, maleimide, N-hydroxysuccinimide, 1,5-difluoro-2,4-dinitrobenzene, imidate, aryl azide, arylacid hydrazide, and p-nitrophenyl-2-diazo-3,3,3-trifluoropropionate.

"Reaction mixture," as used herein, means a mixture of the test sample and other substances used to apply the present invention for the detection of analyte in the test sample. The reaction mixture can include diluents and buffers.

"Test sample," as used herein, means the sample containing analyte to be detected and assayed using the present invention. A test sample can contain other components besides the analyte, can have the physical attributes of a liquid, or a solid, and can be of any size or volume, including for example, a moving stream of liquid. The test sample can contain any substances other than the analyte as long as the other substances do not interfere with the specific binding of the binding molecule with the analyte or the analyte-analog. Examples of test samples include, but are not limited to: Serum, plasma, spinal fluid, sputum, seminal fluid, amniotic fluid, urine, saliva, other body fluids, and environmental samples such as ground water or waste water, soil extracts and pesticide residues.

In one embodiment of the present invention, the foreign a.a. moiety can be an epitope. The foreign a.a. moiety either can be directly inserted into the surface of the starting enzyme or can be used to replace part of a.a. sequence on the surface of the starting enzyme. The term "insert" as used herein, means internal fusion, as opposed to N-terminal or C-terminal fusion. Thus, when the foreign a.a. moiety is a linear peptide, the two terminals, or ends, of the peptide are connected, joined, or fused with two adjacent amino acids on the surface of the starting enzyme. Thus, the foreign a.a. moiety is situated between two neighboring amino acids on the surface of the starting enzyme. The binding surface created from this foreign a.a. moiety can still bind to a binding molecule, such as an analyte or an antibody. The enzymatic activity of the hybrid enzyme is modified or modulated if: (1) The foreign a.a. moiety replaces or is inserted into an a.a. sequence of the starting enzyme at a region in close proximity to the catalytic active site of the starting enzyme and (2) the foreign a.a. moiety binds to its binding molecule. Thus, when the binding molecule binds to the binding surface formed from the foreign a.a. moiety, as long as the foreign a.a. moiety is in proximity of the active site of the starting enzyme, the enzymatic activity of the hybrid enzyme is modulated. Additionally, the foreign a.a. moiety can be at a site remote from the active site and still modulate the enzymatic activity. The analyte can be a small molecule, such as a theophylline, or a macromolecule, such as an antibody.

For the hybrid enzyme in one embodiment of this invention to be suitable for the qualitative or quantitative assay, the hybrid enzyme must meet the following criteria: (1) The foreign a.a. moiety replaces or is inserted into an a.a. sequence of the starting enzyme and does not appreciably destroy the enzymatic activity of the resultant hybrid enzyme; (2) the foreign a.a. moiety in the resultant hybrid enzyme can still bind its binding molecules; and (3) when bound to the binding site of the hybrid enzyme, the binding molecule modulates the enzymatic activity of the hybrid enzyme.

A Hybrid Enzyme Containing a Foreign Amino Acid Moiety Which Serves As An Epitope (Hybrid Enzyme-Epitope)

The present invention is generally applicable to proteins, and more specifically directed to genetically engineered proteins, and their use thereof in qualitative and quantitative assays. A foreign a.a. moiety replaces or is inserted into an a.a. sequence of a starting protein. The foreign a.a. moiety serves as a binding site for a binding molecule and upon being bound by the binding molecule, a change in the genetically engineered protein is measured.

One example of a genetically engineered protein can be an enzyme. Peptide sequences can replace or be inserted into an a.a. sequence of a starting enzyme. For construction of a genetically engineered enzyme to detect antibodies directly, the epitope of the antigen replaces or is inserted into an a.a. sequence of the starting enzyme to yield a hybrid enzyme-epitope. For example, an assay with hybrid enzyme-epitopes for HIV-1 and HIV-2 would include the V3 loop of HIV-1 gp120 protein coded for by a.a. 584–614 from HIV-1 and HIV-2 gp41 peptide inserted into or replacing a.a. sequences of the starting enzymes.

For construction of hybrid enzyme-epitopes to detect an antigen by competition, an antibody with affinity for a defined epitope on the antigen is required and the defined epitope replaces or is inserted into an a.a. sequence of the starting enzyme.

Generally, a foreign a.a. moiety, such as an epitope, can replace or be inserted into an a.a. sequence of a starting protein as follows. The gene for the protein is cloned into an expression plasmid. This can be accomplished by using a polymerase chain reaction ("PCR") to amplify the DNA sequence of the gene from the native source of the enzyme, either a procaryotic or eucaryotic organism. The PCR amplification procedure utilizes knowledge of either partial a.a. sequence of the protein or partial nucleotide sequence of the gene or flanking sequences. The gene can also be obtained by direct chemical synthesis of the DNA encoding the protein. This requires knowledge of either the complete protein sequence or the complete nucleotide sequence of the gene. Once the gene is cloned into a plasmid, the entire nucleotide sequence can be obtained by DNA sequencing and the protein is expressed by introducing the plasmid into a compatible host, e.g., bacterial, yeast or mammalian cells.

If the 3-dimensional structure of the enzyme is known, sites of the epitope being inserted into or replacing an a.a. sequence of the starting enzyme are preferably chosen to be regions that are surface loops near the active site of the starting enzyme. From the nucleotide sequence of the gene, restriction fragment replacements are designed to construct a gene encoding the desired hybrid enzyme-epitope. If the structure of the hybrid enzyme-epitope is not known, the epitope can replace or be inserted into a.a. sequences of the starting enzyme randomly throughout the protein and the resultant hybrid enzyme-epitopes are screened for retention of enzymatic activity. The random epitopes that replace or are inserted into a.a. sequences of the starting enzyme can be done with the appropriate DNA fragment at restriction sites in the gene. For a more thorough scan of the protein, a series of hybrid enzyme-epitope genes can be constructed in which the epitope replaces or is inserted into, one per construct, each a.a. in the enzyme. Finally, the hybrid enzyme-epitopes that maintain enzymatic activity are tested for antibody binding and modulation.

In one embodiment of this invention, AP is modified into a hybrid enzyme-epitope (hereinafter referred to as AP-epitope), that both binds the binding molecule and generates the signal indicating the presence and the amount of the binding molecule. The binding molecule can be an analyte, such as a protein or an antibody. Diagnostic assays based on this technology are homogeneous, simple to perform, and are one-step assays requiring no separation step. The AP-epitopes are preferably produced in *E. coli* and purified to a homogeneous reagent that requires no subsequent chemical modifications.

The AP-epitopes are generated by replacing or inserting into a.a. sequences in the starting AP with DNA sequences encoding epitopes. The resultant protein, AP-epitope, presents the epitope on its surface and acts as a binding molecule. An example of the binding molecule is antibody to the epitope. The complex between AP-epitope and the binding molecule is detected by measuring the amount of enzymatic activity in the complex relative to the activity in the unbound AP-epitope.

In this embodiment, AP was engineered into a binding protein for an antibody by replacing or inserting into a.a. sequences of the starting AP, with DNA sequences encoding epitopes, into the AP gene. The epitopes which replaced or was inserted into a.a. sequences of AP were done at sites known to be near the catalytic site and on the surface of AP. An example of such an epitope is the V3 loop of the HIV-1 gp120 protein. The AP-epitopes were expressed and purified in *E. coli*.

One embodiment of this invention shows that: (1) gp120 peptides can replace or be inserted into a.a. sequences of the starting AP at two regions, inserted between a.a. 407–408 or replacing a.a. 91–93 in AP, without significantly altering enzymatic activity or protein stability; (2) the epitopes, when presented on the surface of AP-epitopes, are still bound by an antibody to gp120 protein; and (3) the binding of anti-gp120 monoclonal antibody (Mab) to the AP-epitope, API1, inhibits the enzymatic activity of API1. Together, these demonstrate the use of AP-epitopes to create AP-based binding proteins that both bind the macromolecule and generate the signal to detect the complex.

Since detection of complex formed between the AP-epitope and antibody requires modulation of AP-epitope's enzymatic activity upon complex formation, regions of AP that were close to the catalytic site were chosen as sites for insertion of the binding surface.

A Hybrid Enzyme Containing A Foreign Amino Acid Moiety Which Serves As A Conjugation Site for A Ligand (Hybid Enzyme-Ligand Conjugate)

In another embodiment of the present invention, the hybrid enzyme is formed whereby a single foreign a.a. is introduced by replacement of or insertion into an a.a. sequence of the starting enzyme, at a selected location close to the active site of the starting enzyme. A ligand can then be conjugated or attached to the foreign a.a. moiety in the hybrid enzyme by means of a suitable linker to form a "hybrid enzyme-ligand conjugate". For simplicity, the following discussion is directed to the situation where the protein is an enzyme, though the discussion is applicable to other proteins and hybrid proteins. The ligand is conjugated or attached to the hybrid enzyme via site-specific conjugation directed by mutation near the active site. The use of site-directed mutagenesis enables a functional group, e.g., a ligand to be attached or introduced at the exact a.a. residues along the polypeptide chain of the starting enzyme. Preferably, the attached ligand should not adversely affect the catalytic function of the hybrid enzyme-ligand conjugate. On the other hand, the attached ligand may increase the catalytic function of the hybrid enzyme-ligand conjugate. Since the attachment site is designed to be close to the active site or the catalytic center of the starting enzyme, when a binding molecule binds to the attached ligand, the rate of catalysis of a substrate by the hybrid enzyme-ligand conjugate is modulated, either increased, decreased or abolished. Generally, the rate of catalysis is decreased.

Careful derivatization of an enzyme with a single ligand can be accomplished via several methods: (1) Point mutations of the corresponding gene coding for that enzyme thus introducing a foreign a.a. moiety via in vivo translation; (2) point mutations of the corresponding gene coding for that enzyme, introducing a foreign a.a. moiety and in vitro translation (Ellman, J., Mendel, D., Anthony-Cahill, S., Noren, C. J., and Schultz, P. G., (1991) Methods In Enzymology, 202, 301–337); and (3) linking the starting enzyme with a cofactor or a derivative of its cofactor by means of a foreign amino acid moiety which replaces or is inserted into an amino acid sequence of the starting enzyme. The cofactor, inhibitor or substrate can carry an analyte, a reactive linker, or a photolabel (MacLean, A. I., Cynkowski, T., and Bachas, L. G., (1992) J. Chem. Soc., Chem. Commun., 18, 1283–85). The reactive linker provides a site of attachment of a ligand to the enzyme.

The foreign a.a. moiety which can be used with the in vivo translation method could be cysteine, histidine or arginine, but preferably cysteine. The in vitro translation method allows for more diversity by using foreign a.a. moieties, such as carbohydrate derivatives of a.a., azide, vicinal diol, ketone, aldehyde, acetal, ketal, ortho ester, and others.

The binding event which causes changes in enzymatic activity can be envisioned by several scenarios. In one scenario, the uniquely reactive foreign a.a. moiety is introduced near the active site wherein the conjugation of or derivatization with a ligand does not drastically affect the enzymatic activity. The binding of the ligand by a binding molecule causes a reduction in enzymatic activity by altering substrate turnover. In another scenario, the uniquely reactive a.a. moiety is introduced near the binding site of a cofactor wherein the conjugation of or derivatization with a ligand does not drastically affect the enzymatic activity. The binding of the conjugated ligand by the binding molecule causes a reduction in enzymatic activity by reducing cofactor association with the hybrid enzyme-ligand conjugate. In yet another scenario, the foreign a.a. moiety is introduced near the interface of a dimeric or multimeric enzyme wherein the conjugation of or derivatization with a ligand does not drastically affect the quaternary structure and the binding of the conjugated ligand by the binding molecule causes a reduction in enzymatic activity by dissociating the dimeric or multimeric structure or by inhibiting the reformation of the quaternary structure. In this latter case the enzyme may be a homo-, a hetero-dimer, or a multimer.

Scenarios besides the above are also possible. For example, conjugation of the uniquely reactive foreign a.a. moiety near the active site or cofactor binding site can cause an inhibition of the activity of the hybrid enzyme-ligand conjugate. Binding of the conjugated ligand by the binding molecule can result in an increase in the enzymatic activity by withdrawing the ligand away from the active site or cofactor binding site. Negative signal response or less enzymatic activity in the presence of analyte is the result.

Determination of the point of derivatization of the starting enzyme can be made several ways. If the starting enzyme's crystalline structure is known, visual and mathematical inspection of the model may show residues near the active site or cofactor binding sites which are accessible to solvent or those involved with interfacial binding of the multimeric form. If the structure is not known but the a.a. sequence is known, mutations directed by structure prediction programs or random mutations and subsequent testing of the mutants may lead to a desirable hybrid enzyme-ligand conjugate.

The above hybrid enzyme-ligand conjugates, are useful for qualitative or quantitative assays. An example of such would be a hybrid enzyme-ligand conjugate wherein: (1) The foreign a.a. moiety replaces or is inserted into an a.a. sequence on the surface of the starting enzyme and does not destroy the enzymatic activity of the resultant hybrid enzyme; (2) the foreign a.a. moiety in the resultant hybrid enzyme can still be conjugated to a ligand forming a hybrid enzyme-ligand conjugate; (3) the conjugated ligand can still bind a binding molecule, such as a receptor, antibody or other protein molecule; (4) an analyte can compete with the conjugated ligand or for the binding molecule; and (5) the binding of the binding molecule to the conjugated ligand modulates the enzymatic activity of the hybrid enzyme-ligand conjugate.

EXAMPLES

Example 1

Design of AP-epitopes

Using the crystal structure of AP, regions of the enzyme were chosen as potential sites to replace or insert with peptides based on proximity to the active site serine 102 (typically within 20 Angstroms), mean temperature factor which reflects the flexibility of the a.a. residue in the structure, surface accessibility of a.a. residues, and location in the cavity that surrounds the active site. Visualization of the 3-dimensional structure of AP and modeling was done using Insight II software (Biosym, San Diego, Calif.) on a Silicon Graphics computer. In addition, the a.a. homology of E. coli AP with other APs, from mammalian sources, Bacillus subtilis, and yeast (Hulett, F. M., Kim, E. E., Bookstein, C., Kapp, N. V., Edwards, C. W., and Wyckoff, H. W. (1991) J. Biol. Chem. 266, 1077–1084), was used to identify regions that were poorly conserved among the different proteins. Assuming that all the AP proteins have the same general 3-dimensional structure, this comparison identified regions in the E. coli AP that might be deleted or changed by an epitope being replaced into or inserted into an a.a. sequence of the starting AP.

The three regions chosen for peptide replacement into or insertion into a starting AP were a.a. 91–93, 167–177, and 407–408 (FIG. 1). Amino acids 167 and 407–408 are parts of small loops that protrude into the cavity surrounding the active site and are within 15 Angstroms of Serine 102. A hormone peptide was accomodated at a.a. 91–93 which form a small loop close to the dimer interface, that points away from the active site (Langen, H. T. and Taylor, J. W. (1992) Proteins: Structure, Function, and Genetics 14, 1–9). Amino acids 169–177 in E. coli AP are in an alpha helix linked by a disulfide bridge between Cysteine 168 and Cysteine 177; this structure is absent in the other AP proteins. The region in AP from a.a. 373–410 (38 a.a.) is larger in the other AP proteins by 32–68 a.a.

To demonstrate the feasibility of the AP-epitopes as binding molecules for HIV-1 antibodies, epitopes from the V3 loop of HIV-1 IIIB gp120 protein were replaced into or inserted into AP. The V3 loop (a.a. 303–338) is the immunodominant region of gp120 and consists of 34 a.a. flanked by cysteine residues which form a disulfide bridge (LaRosa, J. J., et al (1990) Science 249, 932–935). Since the epitope is located in a loop on the surface of gp120 just as it will be located in the AP-epitope, it is likely that antibodies to this epitope will still recognize the epitope in the AP-epitope. In the AP-epitopes, the central 13 a.a., 13 a.a. flanked by two cysteine residues, 34 a.a. or the entire 36 a.a. of the V3 loop were replaced into or inserted into AP. The a.a. sequence of the V3 loop is as follows (central 13 a.a. underlined):

Cys-Thr-Arg-Pro-Asn-Asn-Asn-Thr-Agr-Lys-Ser-Ile-Arg-Ile-Gln-
Arg-Gly-Pro-Gly-Arg-Ala-Phe-Val-Thr-Ile-Gly-Lys-Ile-Gly-
Asn-Met-Arg-Gln-Ala-His-Cys, (SEQ. I.D. NO. 25).

Since AP is a dimeric protein, there are two epitopes replaced into or inserted into each functional AP-epitope.

Example 2

Construction and Expression AP-epitopes

The genes encoding the AP-epitopes were constructed by restriction fragment replacement using a phoA gene that was synthesized to have unique restriction sites (Mandecki, W., Shallcross, M. A., Sowadski, J., and Tomazic-Allen, S. (1991) Protein Engineering 4, 801–804; FIGS. 2A and 2B presents the DNA sequence of the synthetic phoA gene and its resultant a.a. sequence respectively (Sequence I.D. Nos: 1 and 2).

a. Synthetic DNA Fragments

FIG. 3 shows the synthetic DNA fragments that were used as restriction fragment replacements and the resultant foreign a.a. moieties of the AP-epitopes are shown in FIG. 4. FIG. 3 shows api1a, (also listed as SEQ. I.D. NO. 3); api1b (SEQ. I.D. NO. 4); api2a (SEQ. I.D. NO. 5); api2b (SEQ. I.D. NO. 6); api3a (SEQ. I.D. NO. 7); api3b (SEQ. I.D. NO. 8); api5a (SEQ. I.D. NO. 9); api5b (SEQ. I.D. NO. 10); api6a (SEQ. I.D. NO. 11); api6b (SEQ. I.D. NO. 12); api7a (SEQ. I.D. NO. 13); api7b (SEQ. I.D. NO. 14); api8a (SEQ. I.D. NO. 15); api8b (SEQ. I.D. NO. 16); api8c (SEQ. I.D. NO. 17); and api8d (SEQ. I.D. NO. 18). FIG. 4 shows the foreign a.a. moieties in AP-epitopes API1 (SEQ. I.D. NO. 19); API2 (SEQ. I.D. NO. 20); API3 (SEQ. I.D. NO. 21); API5 (SEQ. I.D. NO. 22); API6 (SEQ. I.D. NO. 23); API7 (SEQ. I.D. NO. 24); API8 (SEQ. ID. NO. 25).

The synthetic oligodeoxyribonucleotides were synthesized using Applied Biosystem 394 and 380B synthesizers (Applied Biosystems, Foster City, Calif.). The oligonucleotides were purified by gel electrophoresis in 10% acrylamide, 7M urea, TBE (89 mM Tris borate, 89 mM boric acid, 2 mM EDTA) and quantitated by ultraviolet light absorbence at 260 nm in a Beckman DU7500 spectrophotometer (Beckman Dickinson, San Jose, Calif.) using extinction coefficient values calculated by summing $9400M^{-1}$ $cm^{-1}$ per adenosine, $5000M^{-1}$ $cm^{-1}$ per cytidine, $8000M^{-1}$ $cm^{-1}$ per thymidine, and $10000M^{-1}$ $cm^{-1}$ per guanosine.

The oligonucleotides were 5' phosphorylated by incubating 5 pmoles DNA in 50 mM Tris-HCl pH 8.0, 10 mM $MgCl_2$, 5 mM dithiothreitol (DTT), 1 mM adenosine triphosphate (ATP), and 10 units of T4 polynucleotide kinase (GIBCO BRL, Gaithersburg, Md.) at 37° C. for one hour. Following phosphorylation, 1.25 pmoles (5 μl) of each oligonucleotide was annealed with an equimolar amount of its complementary sequence by heating the mixture to 95° C. and then allowing it to slowly cool to room temperature. These annealed fragments were used directly in ligation reactions.

For the construction of pAPI8, the plasmid coding for API8, the restriction fragment replacement was synthesized from four oligonucleotides (FIG. 3; Sequence I.D. Nos: 15–18). Only oligonucleotides api8b and api8c were 5' phosphorylated. Api8b was then annealed to api8d and api8c was annealed to api8a as described above. The annealed fragments, api8a:api8c (4 pmoles) and api8b:api8d (4 pmoles), were mixed and ligated by adding 1 unit of T4 DNA ligase (GIBCO BRL) and incubated at room temperature overnight. Following ligation of the two fragments, the ligase was heat inactivated at 65° C. for 5 minutes (min.) and 10 units of T4 polynucleotide kinase was added to phosphorylate the 5' ends of api8a and api8d. The kinase was heat inactivated (65° C., 5 min.) and then the fragment ligated to linearized pCB100 as described below.

b. Restriction Enzyme Digestion of Vectors

Two plasmids containing the synthetic phoA gene were used; pUCphoA is pUC18 (Yanisch-Perron, C., Viera, J., and Messing, J. (1988) Gene 33, 103) containing phoA cloned into the BamH1 and HindIII sites of the multiple cloning site (MCS); and pCB100 is the pWM528 vector (Mandecki, M., Hayden, M. A., Shallcross, M. A., and Stotland, E. (1990) Gene 94, 103–107) in which the Spe1 site has been removed and contains phoA as a BamH1/HindIII fragment in its multiple cloning site (MCS). For the construction of pAPI1 and pAPI8, pCB100 (15 μg) was cleaved with Kas1 (9 units, New England Biolabs) and Sph1 (10 units, GIBCO BRL) in 50 μl NE Buffer 2 (New England Biolabs) and 0.1 mg/ml acetylated BSA (New England Biolabs). For the construction of pAPI2, pAPI3, and pAPI5, pUCphoA (6 μg) was cleaved with RsrII (100 units, GIBCO BRL) in 100 μl REact 5 buffer (GIBCO BRL), 1 mM DTT, and followed by ethanol precipitation of the DNA. The Rsrll cleaved DNA was redissolved in 100 μl REact 4 buffer (GIBCO BRL) and digested with Spe1 (20 units, GIBCO BRL). For construction of pAPI6 and pAPI7, pUCphoA (10 μg) was digested with SnaB1 (8 units, New England Biolabs) and Hpa1 (5 units, GIBCO BRL) in 50 μl NE Buffer 4 and 0.1 mg/ml acetylated BSA (New England Biolabs). The linearized vectors were treated with 1 unit of calf intestinal phosphatase at 37° C. for 15 min., followed by phenol/$CHCl_3$ extraction, and ethanol precipitated. The linearized vectors were then redissolved in $dH_2O$.

c. Ligation Reactions

The combination of vectors and fragments ligated together to construct AP-epitope genes (genes which code for AP-epitopes) are shown in Table 1. The linearized, dephosphorylated vectors were ligated to 5' phosphorylated, double-stranded, synthetic DNA fragments as follows: 0.2 μg vector was incubated with 0.25 pmoles synthetic DNA fragment in 10 μl T4 ligase buffer (GIBCO BRL), 1 mM DTT, and 1 unit of T4 DNA ligase (GIBCO BRL) at 16° C. overnight. The ligation mixtures were ethanol precipitated and the DNA redissolved in 10 μl of $dH_2O$. The ligated vectors (5 μl) were transformed into 50 μl of competent *E. coli* HB101 cells (GIBCO BRL) (Maniatis, T., Fritsch, E. F., and Sambrook, *J. Molecular Cloning A Laboratory Manual* (1982) Cold Spring Harbor Laboratory, New York). The transformed cells were plated on LB (Luria broth) (Maniatis, T., Fritsch, E. F., and Sambrook, *J. Molecular Cloning A Laboratory Manual* (1982) Cold Spring Harbor Laboratory, New York) plates containing 150 μg/ml ampicillin and 200 μg of 5-bromo-4-chloro-3-indolyl phosphate (BCIP) (Sigma Chemical Co., St. Louis, Mo.). The presence of ampicillin allowed only cells that contained the plasmid to grow and BCIP is a color indicator for the presence of active AP.

TABLE 1

Plasmid Constructions

| CONSTRUCTED PLASMID | STARTING PLASMID | RESTRICTION FRAGMENT REMOVED | DNA FRAGMENT RELACEMENT |
|---|---|---|---|
| pAP11 | pCB100 | Kas1-Sph1 | api1a:api1b |
| pAP12 | pUCphoA | Spe1-Rsr11 | api2a:api2b |
| pAP13 | pUCphoA | Spe1-Rsr11 | api3a:api3b |
| pAP15 | pUCphoA | Spe1-Rsr11 | api5a:api5b |
| pAP16 | pUCphoA | Hpa1-SnaB1 | api6a:api6b |
| pAP17 | pUCphoA | Hpa1-SnaB1 | api7a:api7b |
| pAP18 | pCB100 | Kas1-Sph1 | api8a-api8b api8c-api8d | d. Characterization of the AP-epitope Constructs

Colonies from the transformation reactions that were blue, indicating AP activity, were selected for characterization. To isolate the plasmid DNA, the colonies were grown in 5 ml LB media containing 100 μg/ml of ampicillin to saturation. The cells were pelleted by centrifugation and then resuspended in 100 μl of 25 mM Tris-HCl pH 8.0, 10 mM EDTA, and 50 mM glucose. Two volumes (200 μl) of 0.2M NaOH, 1% SDS (sodium dodecyl sulfate) was added to the mixture, incubated for 10 min. on ice, and then 150 μl of 3M potassium acetate, pH 4.8, was added and the mixture incubated on ice for 5 min. The mixture was spun for 15 min. in a microcentrifuge and the supernatant removed. To the supernatant, 300 μl of 2-propanol was added and the mixture was incubated at room temperature for 30–60 min. followed by centrifugation as in the previous step. The pellet was redissolved in TE solution (100 μl of 10 mM Tris-HCl, 0.1 mM EDTA, pH 7.5). An equal volume of 5M ammonium acetate was added and the mixture was incubated on ice for 20 min. followed by centrifugation. The supernatant was removed and to it 400 μl of 100% ethanol was added, incubated on ice for 20 min., and then centrifuged. The pellet was redissolved in TE solution containing 20 μg/ml of RNase A and incubated at 37° C. for 15 min. Following the RNase A treatment, NaCl (sodium chloride) was added to a final concentration of 0.1M and the mixture was extracted twice with phenol, once with CHCl$_3$:isoamyl alcohol (24:1), and then the DNA precipitated with two volumes of ethanol. The DNA was redissolved in 0.3M sodium acetate and precipitated again with ethanol. The DNA pellet was washed with 70% ethanol, dried, and redissolved in 50 μl of dH$_2$O. Alternatively, the plasmid DNA was isolated by the alkaline lysis method (Maniatis, T., Fritsch, E. F., and Sambrook, *J. Molecular cloning: A Laboratory Manual* (1982) Cold Spring Harbor Laboratory, New York).

To verify that the phoA restriction fragment had been replaced by the synthetic DNA fragment, the isolated plasmid was digested with the same restriction enzymes used to linearize the vectors for cloning, as described previously (Example 2b). The DNA products were separated by electrophoresis on a 1.5% agarose or 10% acrylamide gel in tris-borate buffer (TBE). The fragments were visualized by staining with ethidium bromide and sized based on the distance migrated relative to DNA molecular weight standards (ΦX174 DNA/HaeIII fragments, GIBCO BRL).

For each construct, the DNA from several colonies that contained the correct size restriction fragment replacement, was sequenced by the double stranded dideoxy method (Zhang, H., Scholl, R., Browse, J., and Somerville, C. NAR (1988) 16, 1220) using a Sequenase Version 2.0 T7 DNA polymerase sequencing kit and 7-deaza-dGTP reagents (United States Biochemical, Cleveland, Ohio). Each vector was sequenced on only one strand and only in the region including and flanking the replacement or insertion DNA fragment.

e. Construction and Expression of AP-epitopes

Table 2 lists the resultant AP-epitopes showing the site modified in AP, type of modification (replacement or insertion), the size of epitope inserted or replaced into AP, color of colonies (*E. Coli* HB101 or MZ13b) containing the plasmid encoding the protein, and whether or not the protein is present in periplasmic protein extracts. The AP-epitope, API1, contains the central 13 a.a. of the V3 loop inserted between a.a. 407–408 in AP (SEQ. I.D. NO. 19). API2 contains the 13 a.a. from the V3 loop inserted between a.a. 167–168 in AP (SEQ. I.D. NO. 20) and API3 contains the 13 a.a. inserted between a.a. 168–169 (SEQ. I.D. NO. 21). In API5, the a.a. 169–177 between the disulfide bridge formed by Cys 168 and Cys 178 have been replaced with the 34 a.a. between the cysteine residues in the V3 loop (SEQ. I.D. NO. 22). In API6, a.a. 91–93 in AP were replaced with the 13 a.a. from the V3 loop (SEQ. I.D. NO. 23). API7 is the same as API6 except that the 13 a.a. replacement is flanked by cysteine residues for a total replacement by 15 a.a. (SEQ. I.D. NO. 24). API8 contains the entire V3 loop (36 a.a.) inserted between a.a. 407–408 in AP (SEQ. I.D. NO. 25).

TABLE 2

| AP-Epitope Hybrid Proteins | | | | |
|---|---|---|---|---|
| CONSTRUCT | SITE MODIFIED[a] | EPITOPE INSERT[b] | COLONY COLOR | PROTEIN EXPRESSION[c] |
| AP11 | 407–408 | 13 a.a. | blue | + |
| AP12 | 167–168 | 13 a.a. | pale blue | – |
| AP13 | 168–169 | 13 a.a. | pale blue | – |
| AP15 | 169–177 | V3 loop | pale blue | – |
| AP16 | 91–93 | 13 a.a. | blue | + |
| AP17 | 91–93 | C-13-C | blue | + |
| AP18 | 407–408 | V3 loop | blue | + |

[a]i indicates an insertion between the a.a. in AP shown; r indicates a replacement of the given a.a. with the epitope Protein expression in Table 2 was determined using BCIP. The blue colony color of cells containing the plasmids coding for API1, API6, API7, and API8 indicated the AP-epitopes were expressed and had enzymatic activity. A periplasmic extract, from MZ13b (plasmid transformation into MZ13b is discussed in Example 3) containing each of the plasmids, contained a protein that migrated on SDS acrylamide gels with the expected molecular weight of each AP-epitope.

The strain MZ13b containing the constructs encoding API2, API3, and API5 formed light blue colonies (colonies without plasmid are white) and the periplasmic extracts did not show the presence of protein of the expected molecular weight. SDS gel-Western blots probed with anti-AP antibody did not detect any API2, API3, nor API5 in the periplasmic extracts. Blots of the cellular material, pelleted after polymyxin B sulfate treatment to release periplasmic proteins, for constructs encoding API2 and API3 were probed with anti-AP antibody and AP-epitope of the expected molecular weight was detected. However, the majority of the AP reactive material was low molecular weight suggesting that these proteins were not transported normally and were degraded.

The crude extracts of API1, API6, API7, and API8 were checked for AP-epitope enzymatic activity by electrophoresis of the AP-epitopes on native gels followed by staining of the gels for AP activity with 5-bromo-4-chloro-3-indolyl phosphate (BCIP). All the AP-epitopes had detectable enzymatic activity and migrate differently than AP, consistent with changes in a.a. sequence in the AP-epitopes. The ability of these AP-epitopes to bind anti-gp120 Mab was also determined using crude extracts electrophoresed in native gels. The gels were Western blotted using anti-gp120 MAb as the primary antibody. API1, API6, API7, and API8 were detected by the anti-gp120 MAb, whereas MZ13b periplasmic proteins and AP were not. This indicated that in the native conformation of the AP-epitopes, the epitope is surface exposed and in a conformation that the anti-gpl20 MAb recognized and bound.

Example 3

Expression and Characterization of the AP-epitopes a. Expression of AP-epitopes

For expression and isolation of the AP-epitopes, the pAPI plasmids were transformed into *E. coli* MZ13b cells which is a strain deleted for phoA (Inouye, H., Pratt, C., Beckwith, J., and Toriani, A. J. (1977) J. Mol. Biol. 110, 75–87). The MZ13b cells were made transformation competent by the following procedure. A culture of MZ13b was grown in LB media overnight, the cells pelleted by centrifugation and resuspended in ¼ the original volume in cold transformation buffer (40 mM potassium acetate pH 6.2, 40 mM $MnCl_2$, 60 mM $CaCl_2$, 100 mM rubidium chloride, 15% sucrose). The cells were incubated on ice for 20 min. and then pelleted by centrifugation. The cells were resuspended in 1/40 the original culture volume in transformation buffer containing 0.04% dimethyl sulfoxide (DMSO) and stored at −70° C. Transformations and colony selection were done as in Example 2c.

For protein isolation, MZ13b containing the pAPI plasmid was grown in SOB media (20 g/l bacto-tryptone, 5 g/l yeast extract, 0.5 g/l) NaCl, pH to 7.5 with KOH, after autoclaving $MgSO_4$ added to 5 mM) containing 100 µg/ml of ampicillin. The cells were pelleted by centrifugation and resuspended in 1/40 the original volume in 0.15M Tris-HCl, 154 mM NaCl, pH 6.6, containing 6 mg/ml of polymyxin B sulfate (Sigma). The cell suspension was incubated at 37° C. for 10 min. and then centrifuged at 13000×g for 30 min. The supernatant contained proteins released from the periplasmic space by the polymyxin treatment and was the crude extract of AP-epitope.

Expression of AP-epitopes was determined by separation of the proteins in the periplasmic extracts by gel electrophoresis. Aliquots of the periplasmic extracts were denatured by boiling in an equal volume of 125 mM Tris-HCl pH 6.8, 2% SDS, 10% glycerol, 1% b-mercaptoethanol, and 0.01% bromophenol blue. The samples were electrophoresed on a PhastSystem using PhastGel Homogeneous 12.5 gels and PhastGel SDS buffer strips (Pharmacia LKB Biotechnology, Piscataway, N.J.) or on standard Laemmli SDS 10% or 12% acrylamide gels (Laemmli, U. K. (1970) Nature 227, 680–685). To visualize the protein bands, the gels were stained in 50% methanol, 7% acetic acid, 0.2% Coomassie R0250 and then destained in 25% methanol, and 7% acetic acid. The apparent size of the protein bands was determined by comparison of their migration distance relative to the migration of protein molecular weight standards (GIBCO BRL).

b. Western Blot Procedure

For Western blots, the proteins were transferred from a PhastGel gel to Problot membrane (Applied Biosystems) using a PhastTransfer apparatus (Pharmacia LKB Biotechnology) (transfer buffer: 25 mM Tris base, 192 mM glycine, pH 8.3, 20% methanol). After transfer, the membrane was blocked in blotto [5% nonfat dry milk in TBS (50 mM Tris-HCl, 150 mM NaCl, pH 7.5)] for 30 min. The membrane was incubated with the primary antibody, rabbit anti-bacterial AP (BAP) (5 Prime to 3 Prime Inc.) diluted 1/1000 in blotto, for 1–2 hours at room temperature and then washed for 5 min. with blotto 4 times. The secondary antibody, goat anti-rabbit IgG-horseradish peroxidase conjugate (Sigma), diluted 1/1000 in blotto, was then added to the membrane, incubated and washed as above. The developing solution was made by mixing 30 mg of 4-chloro-1-naphthol (Sigma) dissolved in 15 ml of cold methanol with 60 ml of TBS containing 0.04% hydrogen peroxide. The membrane was incubated in developer 5–30 min. at room temperature and the reaction stopped by transferring the membrane into water.

c. Activity Stain of AP in Native Gels.

The enzymatic activity of the AP-epitopes was demonstrated by electrophoresis of the proteins in the periplasmic extracts in native gels and then staining the gels for AP activity. Aliquots of the periplasmic extracts were loaded directly onto PhastGel homogeneous 12.5 gels using PhastGel Native buffer strips (Pharmacia LKB Biotechnology). After electrophoresis, the gel was soaked in 100 mM Tris-HCl, 1 mM $MgCl_2$, 1 mg/ml BCIP, pH 8.5 until color developed (2–60 min.). The reaction was stopped by transferring the gel into destain solution (25% methanol, 7% acetic acid). Active AP-epitopes cleaved the BCIP substrate to BCI which formed a blue precipitate in the gel where it was generated thus staining the position of active AP-epitopes. Western blots of identical gels using anti-BAP independently verified the position of the AP-epitopes.

d. Western Blots of AP-epitopes in Native Gels Using Anti-gp120 Monoclonal Antibody The HIV1 gp120 epitope in AP-epitope was still recognized by an antibody to the gp120 epitope. This was demonstrated by seperation of periplasmic extracts or purified AP-epitopes on PhastGel native gels (as described above). The proteins were transferred to Problot membrane and Western blotted as described above. The primary antibody was anti-gp120 (HIV-1) monoclonal antibody (American Bio-Technologies, Inc., Cambridge, Mass.) diluted 1/1000 in blotto and the secondary antibody was horseradish peroxidase-labelled goat anti-mouse IgG (Sigma) diluted 1/1000 in blotto. Identical membranes were probed with anti-BAP antibody as previously described.

Example 4

Purification and Characterization of AP-epitopes a. Protein Purification

*E. coli* MZ13b containing the API plasmids were grown in SOB media containing 100 µg/ml ampicillin and periplasmic extracts were made as previously described (Example 3a). The extract was diluted 10-fold in 25 mM Tris-HCl, 1 mM $MgCl_2$, pH 8.5 or dialyzed into this buffer and then chromatographed on a Q-Sepharose FF column (Pharmacia LKB Biotechnology) using a FPLC system (Pharmacia LKB Biotechnology). AP-epitope was eluted using a linear gradient from 0 to 1M NaCl in 25 mM Tris-HCl, 1 mM $MgCl_2$, pH 8.5. The fractions containing AP activity were pooled and concentrated using an Amicon Ultrafiltration cell with a YN-30 membrane (Amicon, Danvers, Mass.) and dialyzed into 10 mM $Na_3PO_4$, 1 mM $MgCl_2$, 0.025% sodium azide, pH 6.8. The pool was chromatographed on a Hydroxyapatite Ultrogel column (IBF Biotechnics Inc., Columbia, Md.) and AP-epitope was eluted using a linear gradient from 10 mM $Na_3PO_4$, 1 mM $MgCl_2$, pH 6.8 to 500 mM $Na_3PO_4$, 10 mM $MgCl_2$, pH 6.6. The fractions containing AP activity were pooled, concentrated, and dialyzed into 25 mM Tris-HCl, 1 mM MgCl$_2$, pH 8.5. If after the Q-Sepharose and HA Ultrogel columns, the AP-epitope was not pure (as judged by SDS gel electrophoresis), the preparation was further purified by chromatography on Poros R/H column (Perceptive Biosystems) using a Beckman high performance liquid chromatography (HPLC) system (Beckman) with a linear gradient from 2–80% acetonitrile in 50 mM Tris acetate, 2 mM MgCl$_2$, pH 8.0. The final protein preparation were stored in 25 mM Tris-HCl, 1 mM MgCl$_2$, pH 8.5 containing 0.02% sodium azide at 4° C.

The assay for AP activity was performed in 1 ml of 1M Tris-HCl, 1 mM MgCl$_2$, 0.1 mg/ml BSA, pH 8.0 containing 2.5 mM PNPP (p-nitrophenyl phosphate) (Sigma). The conversion of PNPP to p-nitrophenol (PNP) was monitored by following the change in absorbance at 410 nm in a Beckman DU7500 spectrophotometer (Epsilon =1.62×10$^4$ M$^{-1}$ cm$^{-1}$)(Beckman). The initial velocity was calculated using the initial linear portion of a plot of A$_{410}$ versus time.

The purity of the AP-epitopes was judged by Coomassie staining of SDS polyacrylamide gels. All protein preparations contained a single band representing greater than 95% of the total stained protein. AP migrated with an apparent molecular weight of 46000 daltons consistent with the expected monomer size. The AP-epitopes migrated as slightly larger proteins consistent with the expected increase in size due to the addition of the epitope.

The protein concentrations were determined using a Bio-Rad Protein Assay kit (Bio-Rad Chemical Div., Richmond, Calif.) with BSA used as the protein standard. The enzymatically active form of AP is a dimer with each subunit containing an active site. In the AP-epitopes, two epitope inserts are present in the active form. The concentrations of AP and AP-epitope present in assays are expressed in terms of the number of active sites and epitopes present, i.e. the concentration of monomer subunits present.

b. Kinetic Constants of AP-epitopes

The Michaelis-Menton kinetic constants, K$_m$ and V$_{max}$, of the AP-epitopes were determined using PNPP as the substrate in 50 mM Tris-HCl, 1 mM MgCl$_2$, 0.1 mg/ml BSA, pH 8.0. The enzyme concentration was 5 nanomolar (nM) (monomer) and the PNPP concentration varied from 5 to 90 $\mu$M. The assays were performed in 96 well microtiter plates using a total assay volume of 200 $\mu$l. Conversion of PNPP to PNP was measured in a Bio-Rad Model 3550 Microplate Reader (Bio-Rad) at 405 nm and the data analyzed using Kinetic Collector 2.0 software (Bio-Rad). The pathlength was determined empirically to be 0.6 cm by measuring the absorbance of known concentrations of PNP and using an extinction coefficient for PNP of 1.62×10$^4$ M$^{-1}$ cm$^{-1}$. The initial velocity was determined from the initial linear portion of A$_{405}$ versus time. The K$_m$ and V$_{max}$ values were determined from Eadie Hofstee plots. The values in Table 3 are the mean ± one standard deviation from at least three independent determinations.

The values for the protein preparations are summarized in Table 3. Though API8 is stable in crude extracts, it is partially degraded during purification. Comparison of the K$_m$ and V$_{max}$ values for the AP-epitopes to the values for AP showed that neither value had been significantly changed. These results indicated that replacement with, or insertion of, epitopes into AP had little effect on the interaction of substrate and the rate of substrate turnover with the AP-epitopes.

c. Thermal Stabilities of AP-epitopes

The thermal stability of AP-epitopes was determined by incubating 0.5 $\mu$M (monomer) of each AP-epitope in 1M Tris-HCl, 1 mM MgCl$_2$, pH 8.0 at temperatures ranging from 24 to 92° C. for 15 min., followed by quick cooling on ice. The residual activity in each AP-epitope was assayed at 5 nM protein in 1M Tris-HCl, 1 mM MgCl$_2$, pH 8.0, 2.5 mM PNPP as described previously.

TABLE 3

Properties of Ap-epitopes

| Specific Enzyme | K$_m$ ($\mu$m PNPP)[1] | T$_{1/2}$ (°C.) | V$_{max}$ ($\mu$M/min.)[1] | ACTIVITY[2] |
|---|---|---|---|---|
| AP | 21.4 ± 5.2 | 2.8 ± 0.6 | 46.7 ± 6.0 | 78 |
| AP11 | 18.0 ± 1.3 | 2.8 ± 0.2 | 53.1 ± 3.7 | 67 |
| AP16 | 25.3 ± 4.7 | 3.8 ± 0.5 | 61.1 ± 4.9 | 79 |
| AP17 | 30.9 ± 4.7 | 4.4 ± 0.6 | 67.0 ± 2.4 | 77 |

[1]Buffer: 50 mM Tris-HCl, 1 mM MgCl$_2$, 0.1 mg/ml BSA, pH8
[2]Buffer: 1M Tris-HCl, 1 mM MgCl$_2$, 0.1 mg/ml BSA, pH 8; $\mu$moles/min./mg The thermal stabilities of the AP-epitopes indicated that the replacement with, or insertion of, epitopes had little effect on the overall structure of AP. Table 3 gives the temperatures (T$_{1/2}$) at which 50% of the enzyme activity was lost in 15 min. The AP-epitopes API6 and API7 showed T$_{1/2}$ values (79° C. and 77° C., respectively) which was similar to the wild-type enzyme (78° C.) whereas, the thermal stability of API1 was decreased slightly (67° C.).

Together the kinetic and thermal stability data showed that insertion of 13 amino acids between amino acids 407–408 and replacement of 3 amino acids (91–93) with either 13 or 15 amino acids had little or no effect on enzymatic activity or general structure of AP. The extra a.a. sequences are accommodated in the loops in AP and do not cause more than local perturbations to the overall folding and structure of AP. Since AP-epitopes are active, dimer formation must not have been disturbed.

Example 5

Modulation of AP-epitope Enzymatic Activity by Anti-gp120 Monoclonal Antibody

The AP-epitopes were examined for modulation of activity by the addition of anti-gp120 (HIV-1) monoclonal antibody (anti-gp120 MAb) (American Bio-Technologies Inc., Cambridge, Mass.).

a. Dialysis of anti-gp120 MAb

The anti-gp120 MAb, supplied in phosphate buffer saline, was dialyzed into TBS (50 mM Tris-HCl, 150 mM NaCl, pH 7.5) using a Centricon 30 microconcentrator (Amicon). The Centricon 30 was preblocked with BSA following the manufacturers instructions. Two milliters (mls) of 1% BSA in TBS was added to the Centricon 30 and incubated for several hours at room temperature. The BSA was then removed and the Centricon rinsed with dH$_2$O. Water was added and the Centricon spun at 5000×g for 15 min. at 4° C. and repeated. Following the second spin, the retentate was removed. The anti-gp120 MAb was diluted 2–3 fold with TBS and spun as above. 200 $\mu$l of TBS was added to the retentate and the Centricon respun, and after repeating 4–5 times, the retentate was removed. The volume of the retentate was measured and the concentration of the anti-gp120 MAb was determined from the intensity of the Coomassie stained bands on an SDS polyacrylamide gel relative to the staining intensity of a known concentration of the MAb electrophoresed on the same gel. No BSA was detected in the MAb preparations.

b. Modulation Assay

Inhibition of enzymatic activity was determined by incubating 5 nM (monomer) of AP-epitope with 0–50 nM of anti-gp120 MAb in 50 mM of Tris-HCl, 1 mM $MgCl_2$, 0.1 mg/ml BSA, pH 8.0 at room temperature for 5–10 min. The amount of enzymatic activity in the API-anti-gp120 MAb complex was measured by adding PNPP to a final concentration of 100–200 μM and monitoring the change in absorbance at 410 nm in a spectrophotometer over time. The fraction of enzyme activity inhibited by the addition of MAb was calculated from the $v_0$ at each anti-gp120 MAb concentration divided by the $v_0$ in the absence of anti-gp120 MAb.

Figure 6:
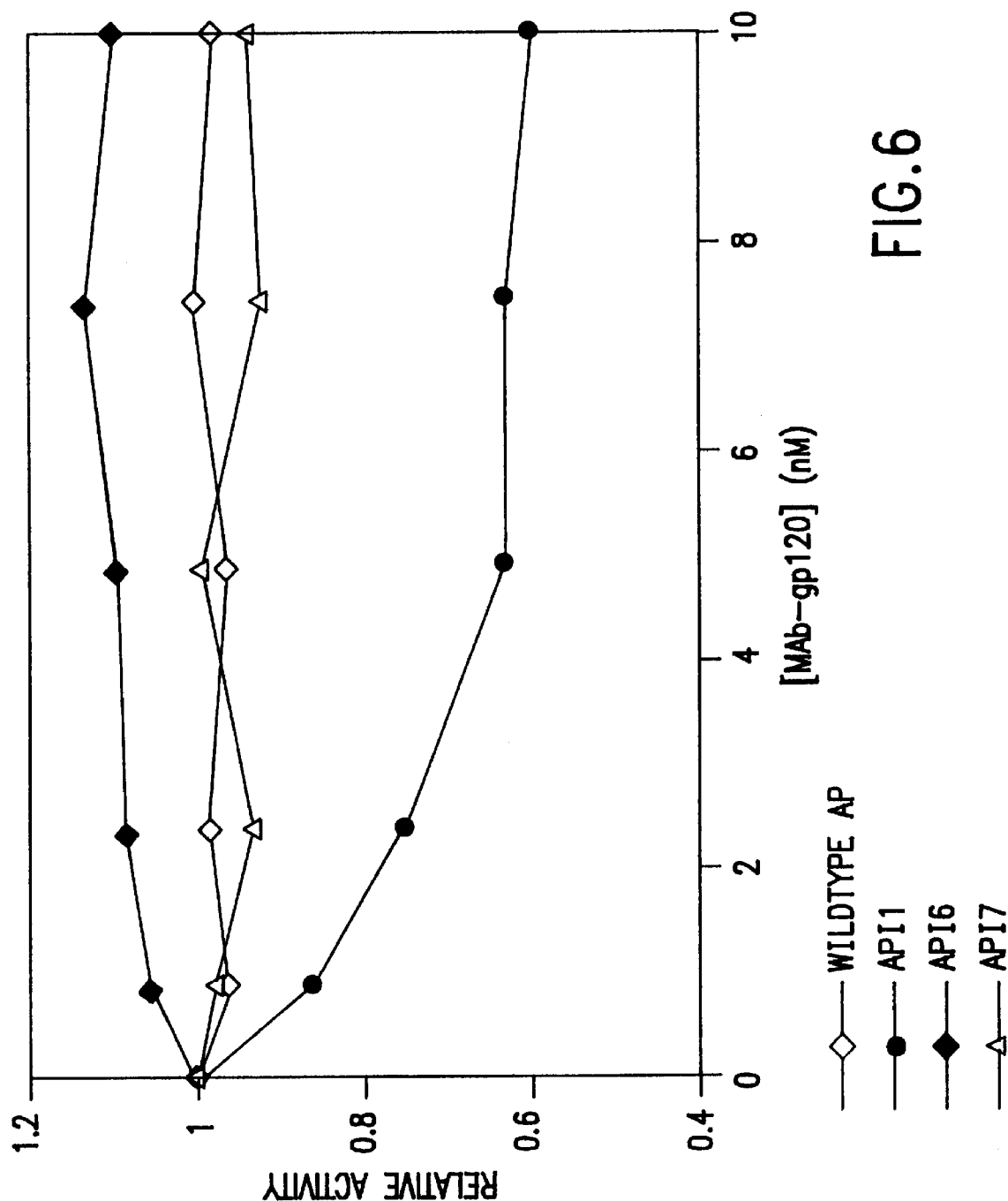
FIG. 6 shows the modulation of AP-epitopes enzymatic activity by different concentrations of anti-gp120 MAb using p-nitrophenyl phosphate (PNPP) as the substrate. AP-epitopes were present at 5 nM and activity is expressed relative to the initial rate of hydrolysis of PNPP in the absence of anti-gp120 MAb.
Figure 7:
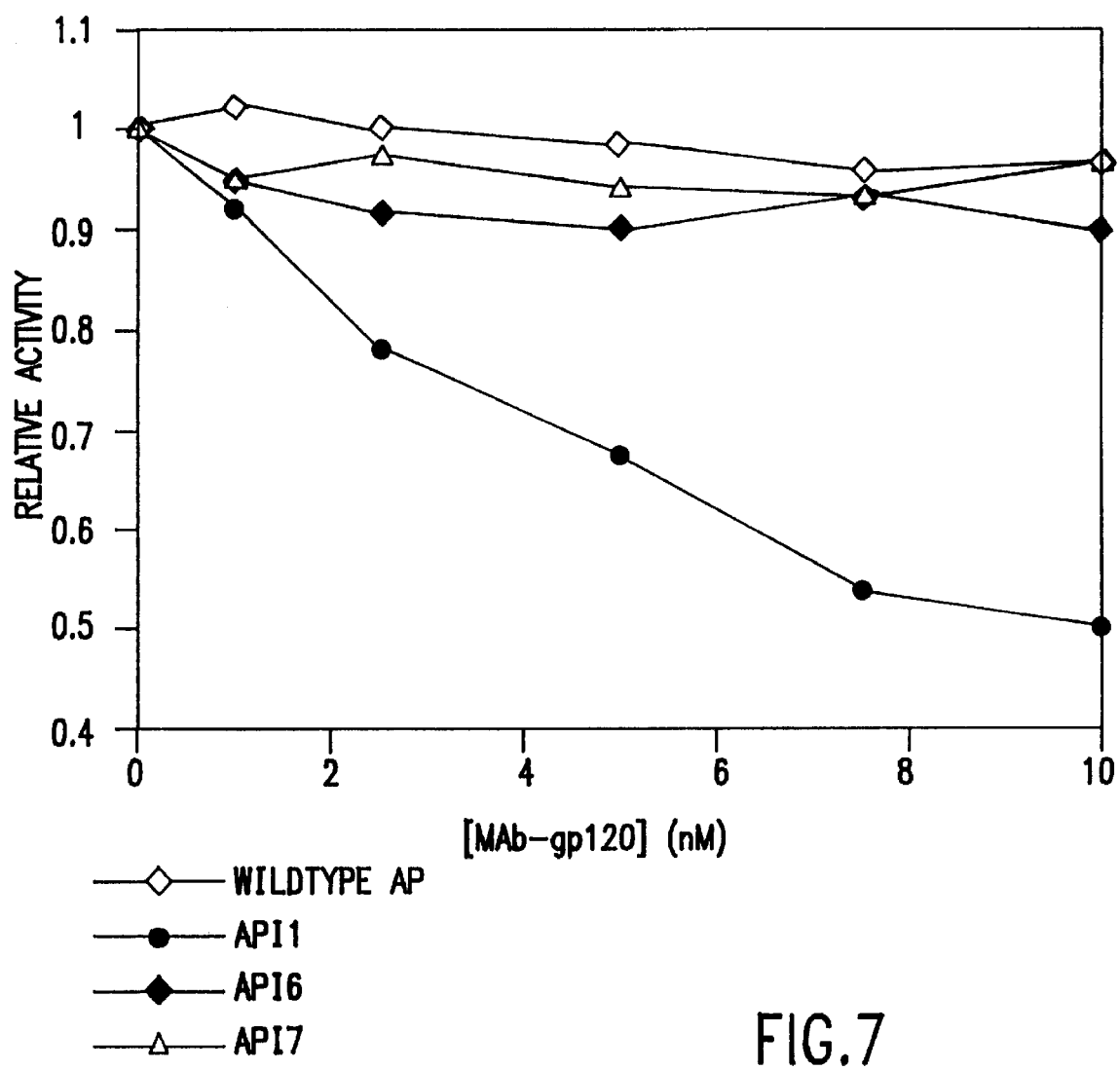
FIG. 7 shows the modulation of AP-epitopes enzymatic activity by different concentrations of anti-gp120 MAb using FDP as a substrate. AP-epitopes were present at 5 nM and activity is expressed relative to the initial rate of hydrolysis of FDP in the absence of anti-gp120 MAb.
Figure 8:
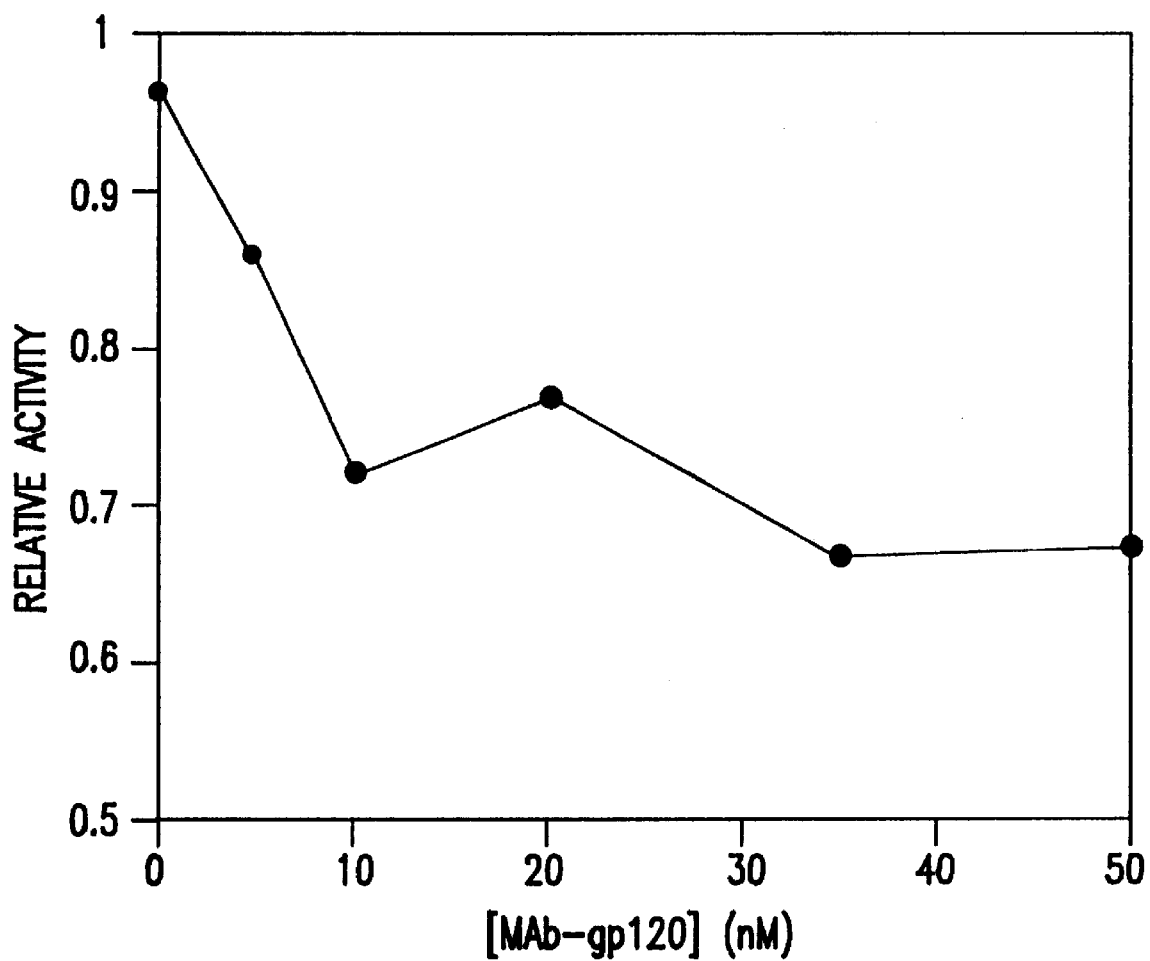
FIG. 8 shows the modulation of API1 enzymatic activity by anti-gp120 MAb using 4-methylumbelliferyl phosphate (MUP) as the substrate. API1 was present at 0.05 nM and the activity is expressed relative to the initial rate of hydrolysis of MUP in the absence of anti-gp120 MAb.
Figure 9:
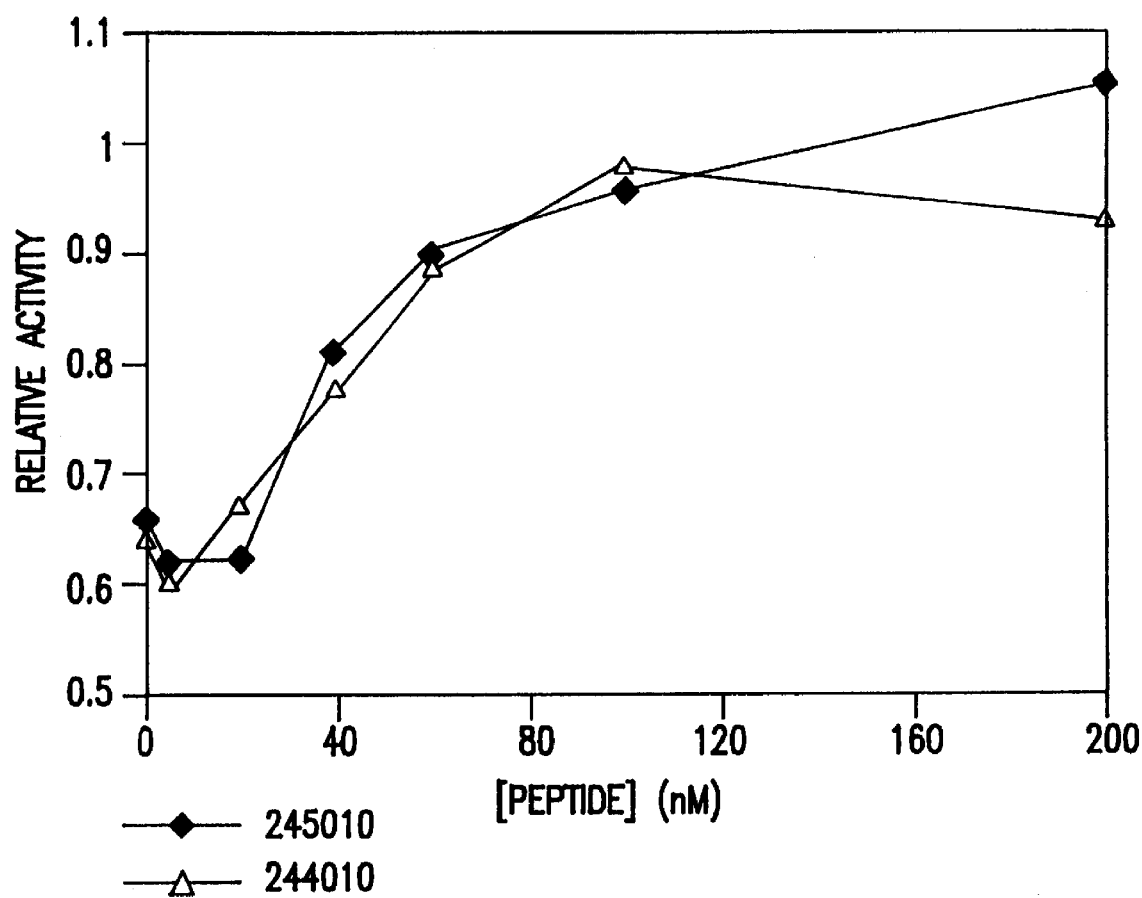
FIG. 9 shows the effect of HIV-1 gp120 peptides on the modulation of API1 enzymatic activity by anti-gp120 MAb, wherein PNPP was the substrate. API1 (5 nM) and peptides were premixed before anti-gp120 MAb (20 nM) was added. Activity is expressed relative to activity in assays of API1 in the presence of given peptide concentration without anti-gp120 MAb present.
Figure 10A:
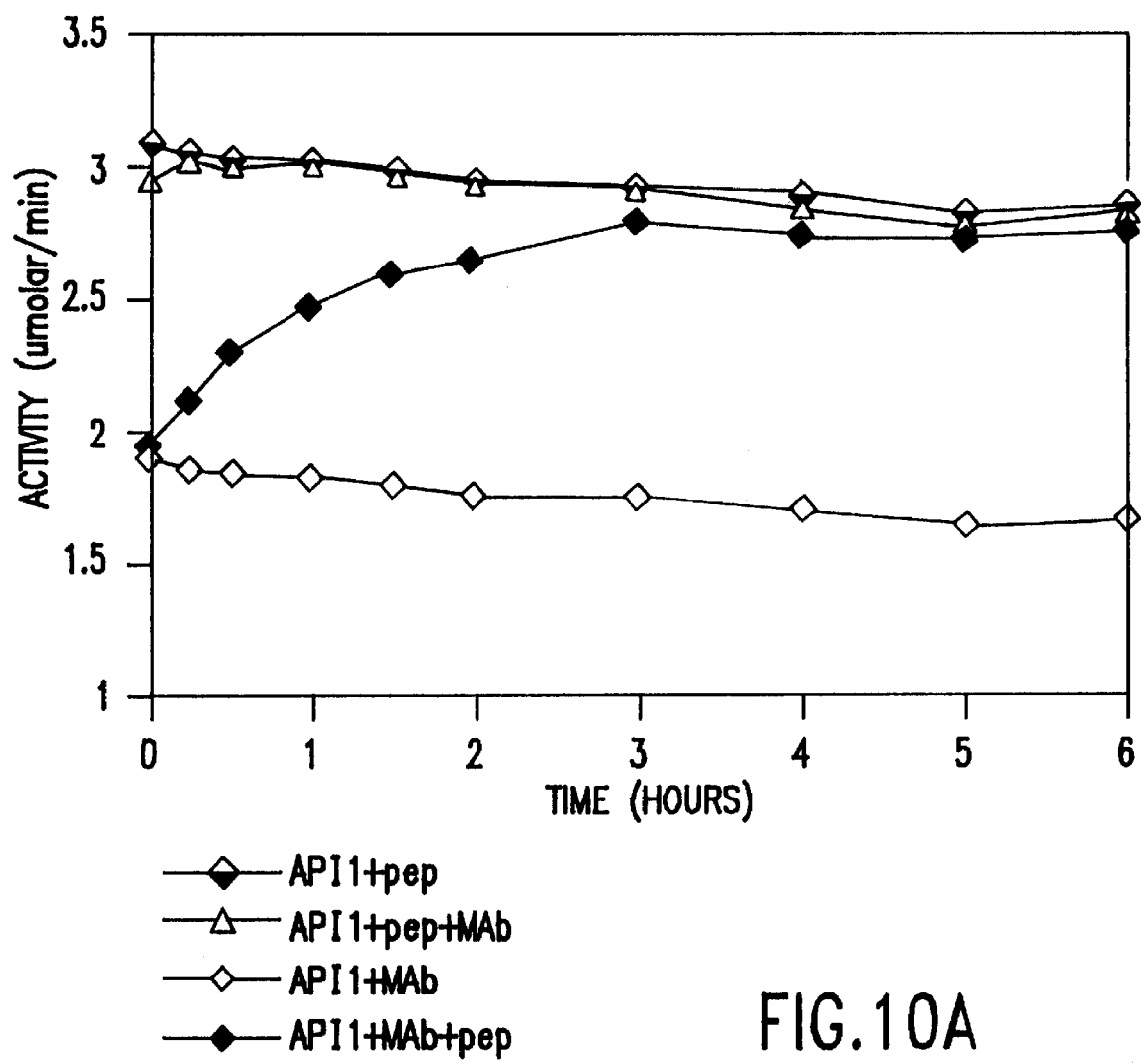
FIG. 10A shows the rate of hydrolysis of substrate PNPP by API1 (5 nM) in the presence and absence of anti-gp120 MAb (20 nM) and peptide (pep) 245010 (4 $\mu$M) over time. In the reaction involving API1 and the peptide (denoted with the legend "API1+pep"), the API1 and peptide were mixed together. In the reaction involving the API1, peptide, and anti-gp120 MAb (with the legend "API1+pep+MAb"), the API1 and peptide were premixed before the anti-gp120 MAb was added. In the reaction involving API1 and the anti-gp120 MAb (with the legend "API1+MAb"), API1 and the anti-gp120 MAb were mixed together. In the reaction involving the API1, anti-gp120 MAb, and peptide (with the legend "API1+MAb+pep"), the API1 and anti-gp120 MAb were premixed before the peptide was added.
Figure 10B:
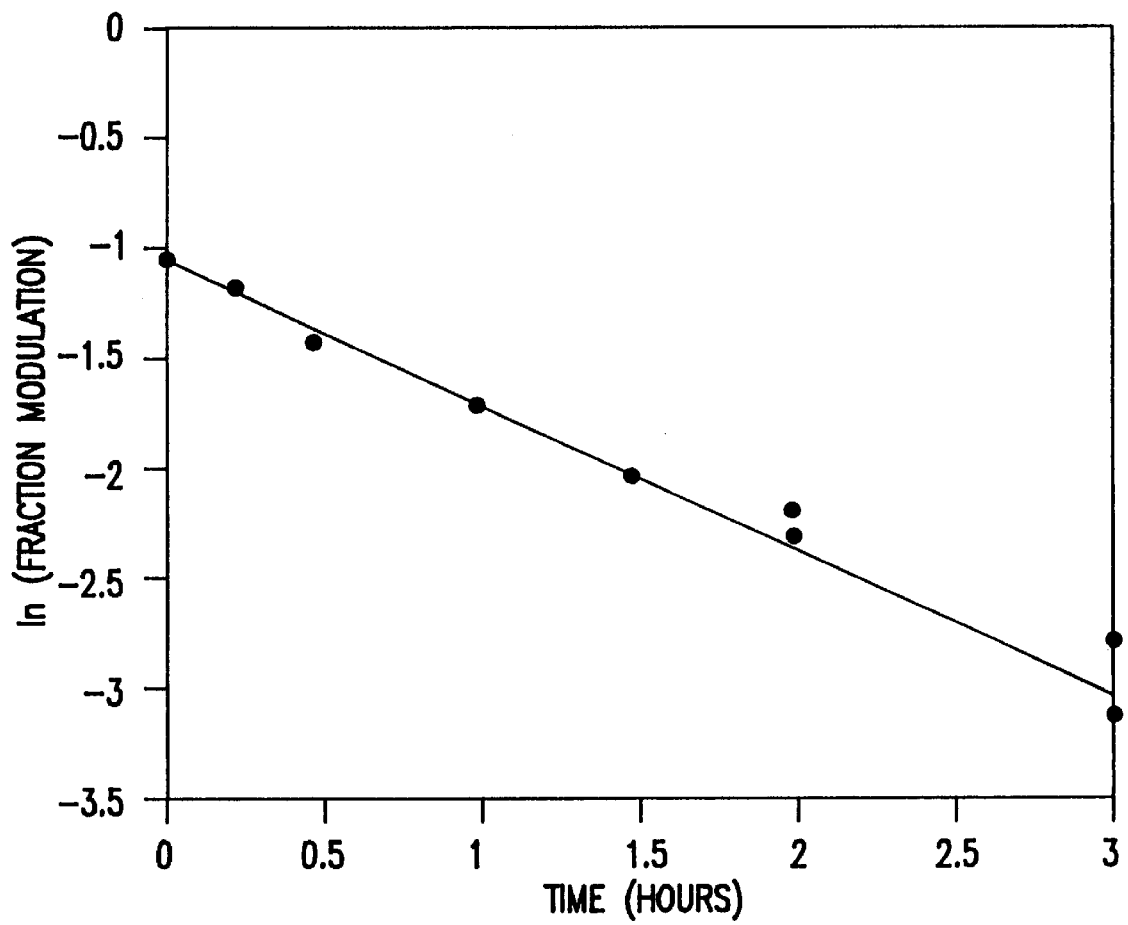
FIG. 10B shows the determination of the dissociation rate constant for the API1-anti-gp120 MAb complex. Data points represent the results of two independent experiments performed as in FIG. 10A.

FIG. 6 shows a typical experiment whereby the AP-epitopes (API1, API6, and API7) and AP were assayed at 5 nM (monomer concentration) in the presence of 0 to 10 nM anti-gp120 MAb using PNPP as a substrate. The activities of wild-type AP, API6, and API7 were not significantly inhibited by the anti-gp120 MAb. In fact, API6 showed a slight enhancement of activity in the presence of anti-gp120 MAb. In contrast, API1 enzymatic activity was inhibited by anti-gp120 MAb. The amount of inhibition increased with increasing concentration of anti-gp120 MAb to a maximum of 40%. Addition of an unrelated antibody (H110, a monoclonal antibody to carcinoembryonic antigen) did not significantly inhibit API1 activity (approximately10% inhibition).

Other substrates for AP were also used in the modulation assays performed to examine the dependence of inhibition on the nature of the substrate. Conversion of fluorescein diphosphate (93 mM FDP, Mg salt) to fluorescein was measured at 490 nm (Epsilon=$7.5\times10^4$ $M^{-1}$ $cm^{-1}$) in a spectrophotometer. Assays using 4-methylumbelliferyl phosphate (12 μM MUP) were performed using a Spex (Beckman) fluorometer. Conversion of MUP to MU (methylumbelliferyl) was determined using an excitation wavelength of 362 nm and measuring the emission intensity at 447 nm.

FIG. 7 shows that, using FDP as substrate, as with PNPP, AP, API6, and API7 were not inhibited by anti-gp120 MAb whereas, API1 was inhibited approximately 50%. Inhibition of API1 with FDP was only slightly higher than with PNPP as the substrate and higher anti-gp120 MAb concentration (up to 50 nM) did not increase inhibition.

The use of the fluorogenic substrate MUP to detect inhibition of API1 enzyme activity by anti-gp120 MAb was done (FIG. 8). In this assay, signal detection was more sensitive and allowed smaller amounts of enzymatic activity to be detected. API1 was inhibited by nM concentrations of anti-gp120 MAb with a maximum inhibition of 32%. For the MUP assays, 50 pM API1 was used which was 100-fold less than in the spectrophotometric assays.

PNPP and FDP in spectrophotometric assays and MUP in a fluorescence assay made it possible to use pM to nM concentrations of API1 to detect nM concentrations of the antibody. The amount of the antibody present, within a range, was proportional to the decrease in enzymatic activity. Thus, antibody present in the reaction mixture, in the range of 0.5 to approximately 10 nM, can be quantitated. The assays are in a format that are simple and homogeneous, i.e., mix and read.

Western blots of API1, API6, and API7 electrophoresed on both native and SDS acrylamide gels and probed with anti-gp120 monoclonal antibody (primary antibody) showed that in both their native and denatured conformations, the epitopes were recognized and bound by the anti-gp120 MAb (FIG. 5). The fact that AP was not bound by the anti-gp120 MAb verified that the presence of the epitope in the AP-epitopes was a functional binding site on AP. The epitope removed from its native context in HIV gp120 protein and presented in a foreign context in AP retained binding affinity for antibody.

The fact that AP was not inhibited suggested any inhibition by the anti-gp120 MAb was due to binding to the epitope in the AP-epitopes. Additionally, API6 and API7 contain the epitope and bind the anti-gp120 MAb by Western blot analysis but their enzymatic activities were not inhibited by anti-gp120 MAb. This suggested that inhibition was dependent on where the epitope was replaced or inserted into AP.

c. Peptide Competition

To determine that modulation of API1 by the anti-gp120 MAb was due to interaction of the anti-gp120 MAb with the gp120 epitope inserted into AP, peptides containing the epitope sequence were tested for the ability to block inhibition. The peptides obtained from American BioTechnologies, Inc., were: #245010 gp120 (a.a. 302–324) (Seq I.D. No. 27); Thr-Arg-Pro-Asn-Asn-Asn-Thr-Arg-Lys-Ser-Ile-Arc-Ile-Gln-Arg-Gly-Pro-Gly-Arg-Ala-Phe-Val-Thr; and #244010 gp120 (a.a. 312–327) (SEQ. I.D. NO. 28); Ile-Arg-lie-Gln-Arc-Gly-Pro-Gly-Arg-Ala-Phe-Val-Thr-Ile-Gly-Lys. The underlined sequence is the peptide inserted into API1. To determine if the peptides could prevent inhibition of API1 by anti-gp120 MAb, API1 (5 nM) was mixed with peptide (0–200 nM), then anti-gp120 MAb (20 nM) was added and the mixture incubated for 10 min. After incubation, PNPP was added and enzyme activity measured. Restoration of API1 enzymatic activity by the addition of peptide to preformed API1- anti-gp120 MAb complexes was determined by incubating API1 (5 nM) with anti-gp120 MAb (20 nM) for 5–10 min., then adding peptide (4 μM) to the complex and incubating 0–6 hr., followed by the addition of PNPP and the activity assayed. The reactions were performed in modulation assay buffer and enzyme activity measured in a spectrophotometer as described above (Example 5b).

Peptides premixed with API1 and then mixed with anti-gp120 MAb blocked inhibition of API1 activity by the anti-gp120 MAb (FIG. 10*a*). Competition between API1 and peptide for binding the anti-gp120 MAb provided the basis for assays that could detect the antigenic protein that the epitope was derived from by competition. The amount of the antigen present, within a range, was proportional to the increase in enzymatic activity. A molar excess of peptide was added to preformed API1- anti-gp120 MAb complexes and slowly restored some of the enzymatic activity of API1 (FIG. 10A). Activity was fully restored in 5–6 hours which demonstrated the stability of the API1-anti-gp120 MAb complex. Premixed API1 with 4 mM peptide before the addition of anti-gp120 MAb prevented modulation of API1 by the anti-gp120 MAb. It also demonstrated that this concentration of peptide was sufficient to prevent rebinding of anti-gp120 MAb to API1 once the complex has dissociated. The dissociation rate constant of the complex was calculated from this data assuming that the amount of enzymatic activity was directly proportional to the fraction of API1 bound by anti-gp120 MAb (i.e. 60% activity was obtained when 100% of API1 was bound by anti-gp120 MAb and 100% activity was obtained when 0% API1 was bound). A plot of In (fraction modulation) versus time gave a line that had a slope that was equal to the negative dissociation rate constant ($k_d$) (FIG. 10B). The $k_d$ for the complex was determined to be $1.7\times10^{-4}$ $sec^{-1}$ (halflife of the complex is 68 min.) (FIG. 10B).

Example 6

Native Gels to Examine API- anti-gp120 Complexes

Complex formation between the AP-epitopes and anti-gp120 MAb was examined using native gel electrophoresis. The API and anti-gp120 MAb were diluted in 50 mM Tris-HCl, 1 mM $MgCl_2$, pH 7.5 and mixed at various concentrations. After incubation at room temperature for 10–15 min., the samples (2 μl) were electrophoresed on PhastGel homogeneous 7.5% or 12.5% gels using PhastGel native buffer strips (Pharmacia LKB Biotechnology, Inc.). Following electrophoresis, the gel was stained for AP activity (Example 3c) until color developed.

Figure 11A:
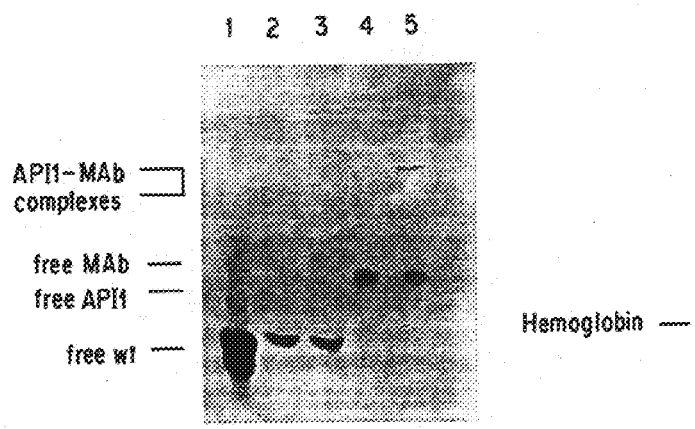
FIG. 11 shows the gel shift assay for complex formation between AP1 and anti-gp120 MAb. a.) 12.5% native gel; lane 1, hemoglobin protein marker; lane 2, AP (1.1 $\mu$M); lane 3, AP (1.1 $\mu$M)+anti-gp120 MAb (0.67 $\mu$M); lane 4, API1 (1.1 $\mu$M); lane 5, API1 (1.1 $\mu$M)+anti-gp120 MAb (0.67 $\mu$M). b.) 7.5% native gel: lane 1, hemoglobin protein marker; lane 2, API1 (0.5 $\mu$M); lane 3, API1 (0.5 $\mu$M)+anti-gp120 MAb (0.1 $\mu$M); lane 4, API1 (0.5 $\mu$M)+anti-gp120 MAb (0.2 $\mu$M); lane 5, API1 (0.5 $\mu$M)+anti-gp120 MAb (0.3 $\mu$M); lane 6, API1 (0.5 $\mu$M)+anti-gp120 MAb (0.5 $\mu$M); lane 7, API1 (0.5 $\mu$M)+anti-gp120 MAb (1.0 $\mu$M); lane 8, AP (0.5 $\mu$M).
Figure 11B:
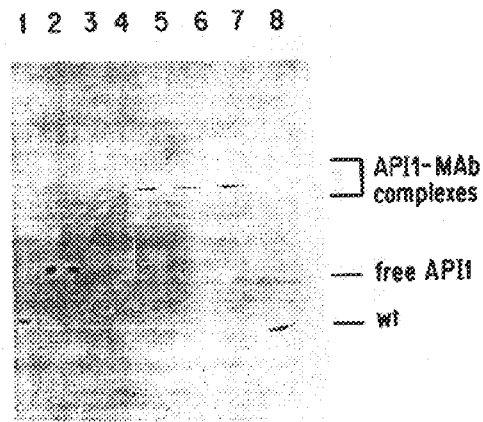

API1 was inhibited to a maximum of 40–50% and API6 and API7 were not inhibited even at a 10-fold molar excess of the anti-gp120 MAb. The ability of the anti-gp120 MAb to bind all the AP-epitope present in the protein preparations was demonstrated using native gels. FIG. 11a shows a native gel stained for enzymatic activity of AP and API1, preincubated with and without anti-gp120 MAb. The migration of AP was not altered by anti-gp120 MAb which indicated that no stable complex was formed. In contrast, incubation of API1 (1.1 μM) with 0.67 μM anti-gp120 MAb resulted in a shift of some of the API1 to a slower migrating species. This gel shift indicated that the API1 was in a complex with the anti-gp120 MAb. FIG. 11b shows a titration of 0.5 μM API1 with anti-gp120 MAb from 0–1 μM. As the anti-gp120 MAb concentration was increased, all the API1 was shifted into complexes (at least 3 different complexes are visible on the gel). Western blots of similar gels probed with anti-mouse IgG conjugate showed that anti-gp120 MAb was present in the complexes. This result showed that all the API1 protein in the preparation could be bound by the anti-gp120 MAb even though its activity was only inhibited 40–50%. Native gels of API6 and API7 in the presence of anti-gp120 MAb showed that all the API6 formed complexes with anti-gp120 MAb but that API7 did not form stable complexes. API7 was detected in Western blots using anti-gp120 MAb but its activity was not inhibited by the anti-gp120 MAb. The native gel suggested that API7 in the presence of anti-gp120 MAb resulted in unstable complexes.

Example 7

Application of AP-epitope in Homogeneous Assays

The binding molecules for AP-epitope based assays can be macromolecules, such as antibodies, protein antigens or any antigen that can be mimicked by a peptide sequence.

Figure 12:
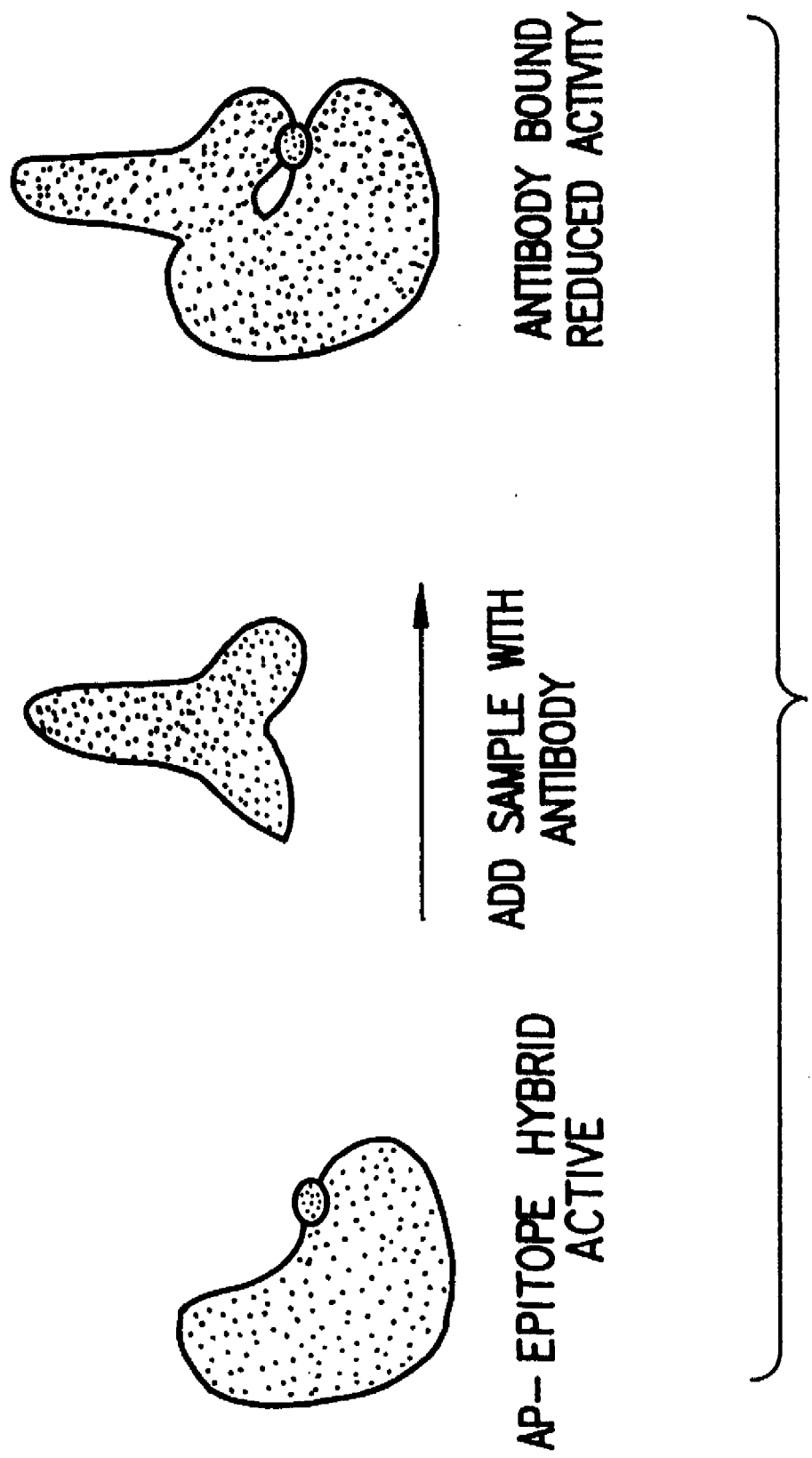
FIG. 12 is a schematic representation of a direct homogeneous assay for the presence of antibody in a sample by an AP-epitope.
Figure 13:
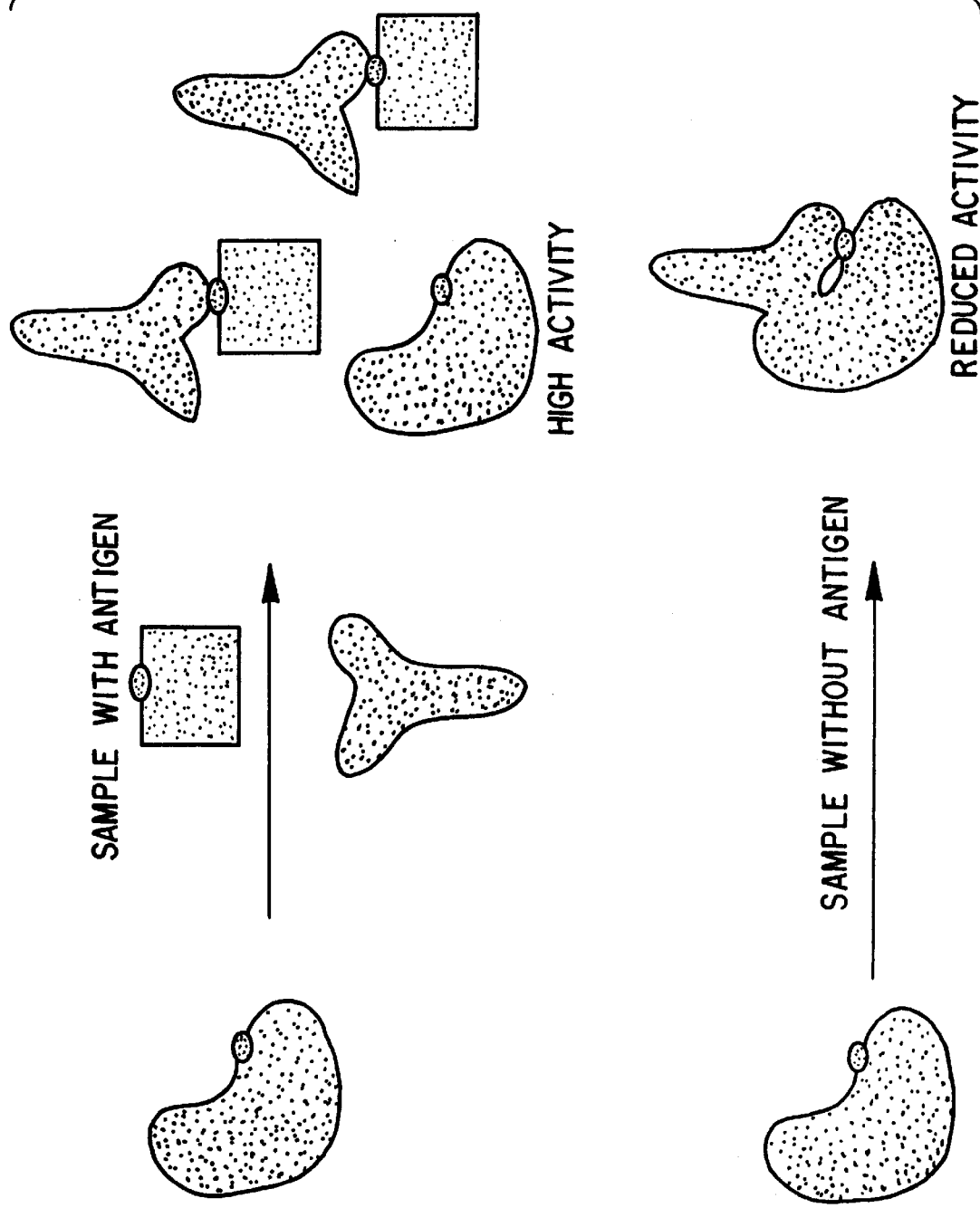
FIG. 13 is a schematic representation of a competitive homogeneous assay for the presence of antigen in a sample by an AP-epitope.
Figure 14:
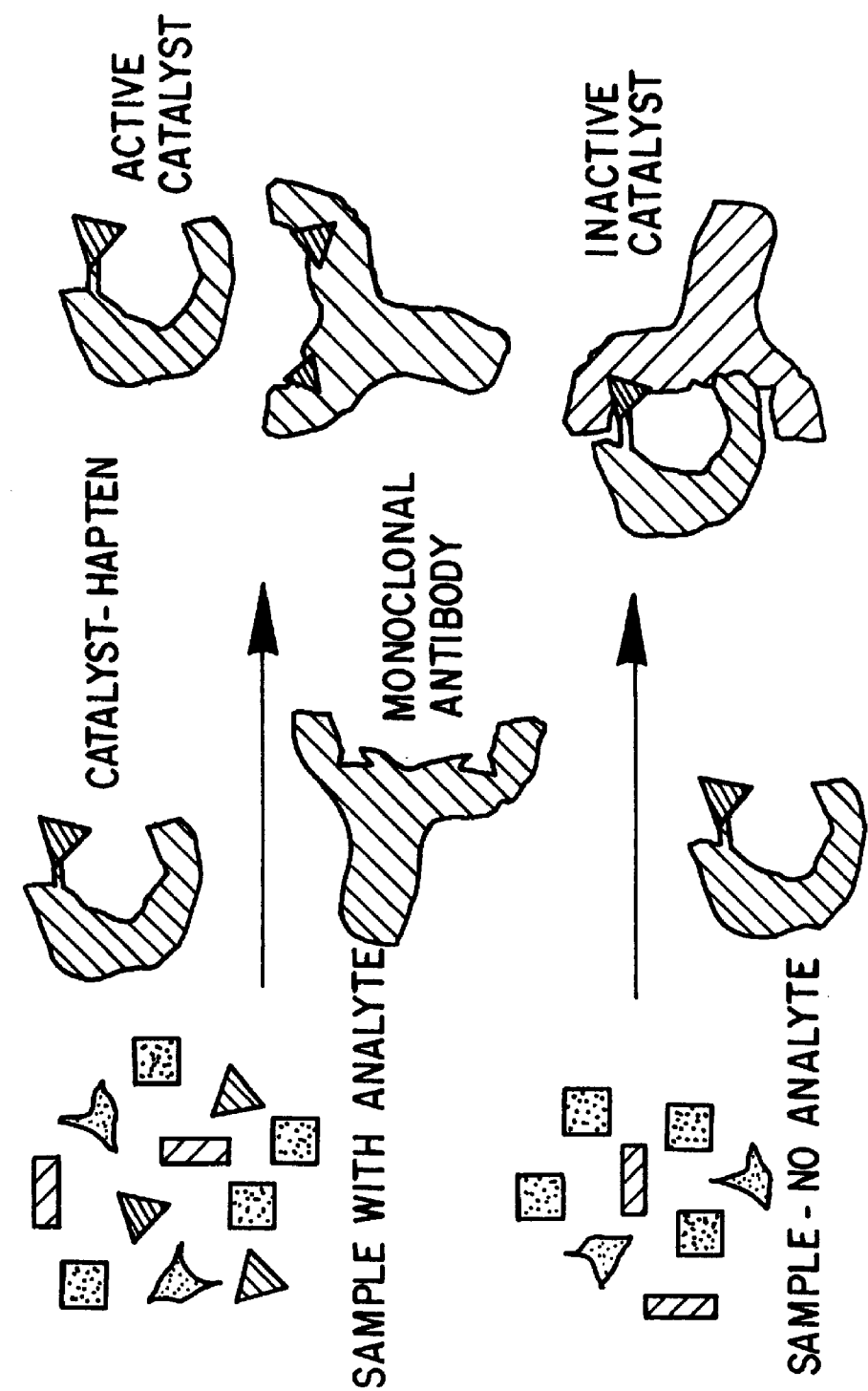
FIG. 14 is a schematic representation of a competitive homogeneous assay for the presence of an analyte in a sample by a hybrid enzyme-ligand conjugate. The hybrid enzyme-ligand conjugate is denoted as "Catalyst-Hapten" in the figure.

The AP-epitopes can be used in a direct assay for the detection of the presence, or quantity, of antibody to the epitope in a reaction mixture. In the assay, the presence of antibody would decrease enzymatic activity (FIG. 12). Alternatively, the antigenic protein containing the epitope sequence could be detected by competition with the AP-epitope for binding antibody present in the reaction mixture. In this assay, the presence of antigen in a reaction mixture would block or decrease antibody binding to the AP-epitope and result in increased enzymatic activity (FIG. 13).

a. Antibody Detection

AP-epitopes that are modulated by antibody binding can be used in both qualitative and quantitative homogeneous assays. For a qualitative assay to detect antibody to the epitope, the activity of AP-epitope in the presence of test sample is compared to the activity in the absence of sample. A decrease in enzymatic activity indicates antibody to the epitope is present in the test sample (FIGS. 12 and 6–8). For a quantitative assay, the amount of antibody in a test sample, the reduction in enzymatic activity by a given amount of test sample is compared to a calibration curve. The calibration curve was generated by adding defined amounts of antibody to AP-epitope and the extent of inhibition was measured as a function of antibody concentration. The amount of antibody in a test sample was equivalent to the concentration of antibody in the calibrators that gave the same level of inhibition.

b. Antigen Detection

The detection of the antigen containing the epitope is a competition-based assay in which the AP-epitope and test sample compete for binding an antibody present in the reaction mixture. For a qualitative assay, the level of inhibition of the AP-epitope upon addition of the antibody is compared, in the absence and presence of, test sample. If antigen is present in the test sample, it will bind antibody and reduce the amount of antibody available to bind to the AP-epitope, thus the level of enzyme activity will be high. If no antigen is present in the sample, all the antibody will be available to bind the AP-epitope and the level of enzyme activity will be low. For a quantitative assay for antigen, the level of antigen in the sample is determined by comparison to a calibration curve. The calibration curve is generated by adding known concentrations of antigen to reaction mixtures and measuring the level of AP-epitope enzymatic activity as a function of the amount of antigen present.

c. Heterogeneous Assay Format

The use of AP-epitopes in homogeneous assays is based on the ability of bound antibody to modulate the enzymatic activity of the AP-epitope. AP-epitopes may also be used in heterogeneous assays in a way that does not require modulation of enzymatic activity. For example, API6 and API7 bind antibody but are not modulated. In the heterogeneous assay format, the AP-epitope is used to enzymatically label antibody. The antibodies in a sample are captured on a solid phase, the AP-epitope is added and allowed to bind to antibody, and then the solid phase is washed to remove unbound AP-epitope. If antibody to epitope is present in the sample, the AP-epitope is captured and AP activity detected after the wash step. If no antibody to the epitope is in the sample the AP-epitope is not captured and no enzymatic activity is detected.

In a similar manner, antigen in a sample can be detected by competition. Antibody on a solid phase will be used to capture either antigen or AP-epitope. The presence of antigen in a sample will reduce the amount of AP-epitope captured by antibody and decrease the enzymatic activity detected. The absence of antigen in a sample will leave all the antibody free to bind the AP-epitope resulting in high enzymatic activity.

Both types of heterogeneous assays can be qualitative or quantitative as described for the homogeneous assays.

Example 8

Preparation of Hybrid Enzymes by a Cysteine Mutation

The vector used for mutagenesis, pUCphoA, is the same one described earlier. Briefly, this plasmid consists of the AP gene (phoA) inserted in the multicloning region of the commercial plasmid pUC18, a high copy plasmid (50–200/cell) which also expresses b-lactamase for screening purposes. The phoA gene contains the native ribosome binding site for expression and the leader sequence which is clipped by proteolysis during export from the cytosol into the periplasm. The entire gene (1454 base pairs) was inserted between the restriction endonuclease sites of BamH I and Hind III of the pUC18 multicloning region. The sequence of the AP gene, which was inserted between the Bam HI and Hind III restriction sites of the pUC18 vector, is shown above the sequence. Also shown is the a.a. sequence, with residue numbers designated on the right, which starts with the first residue of the mature protein, indicated by the caret (^). Mutants prepared are designated by underlining the native residue which has been changed to cysteine in all cases. (FIG. 15; SEQ. I.D. NO. 26 is the nucleotide sequence and SEQ. I.D. NO. 31 is the a.a. sequence).

Two methodologies were used to prepare the cysteine mutants, mutagenesis by fragment replacement and M13 mutagenesis. The mutants pKJ1–pKJ7 (plasmids which coded for hybrid enzymes KJ1–KJ7) were prepared via the former method while mutants pKJ8–pKJ12 (plasmids which coded for hybrid enzymes KJ8–KJ12) were prepared via the latter method. The method of fragment replacement will be detailed for the production of pKJ3, while M13 mutagenesis will be detailed for pKJ9.

All restriction endonucleases and other enzymes were purchased from Bethesda Research Laboratories or New England BioLabs. Competent cells were purchased from Bethesda Research Laboratories for transformations. DNA oligomers were synthesized on a Model 394 or 380B DNA Synthesizer from Applied Biosystems (Ramsey, N.J.) utilizing standard chemistries. Characterization of the mutants was accomplished using Sanger sequencing methods with US Biochemical Sequenase V2.0 sequencing kit and electrophoresis equipment from Bethesda Research Laboratories, Model S2. M13 mutagenesis was carried out via the method of Kunkel (Kunkel, T.A., Proc. Natl. Acad. Sci. USA, 82, 488–492, 1985) using Muta-Gene M13 In Vitro Mutagenesis Kit from Bio-Rad and the protocols described therein.

a. Mutation via Fragment Replacement (i) Double digest of pUCphoA with restriction enzymes Spe I and Mlu I Four $\mu$g of plasmid, pUCphoA, was treated with restriction endonucleases Spe I (10 U) and Mlu I (10 U) in React #3 buffer (BRL) and incubated for 2 hours at 37° C. in a total of 40 $\mu$l. The reaction mixture was concentrated and applied to a 1% low-melting agarose gel and electrophoresed. The band corresponding to the cut vector was excised from the gel and purified using Prep-a-Gene kit (Bio-Rad).

(ii) Preparation of double stranded replacement containing the mutation LYS167CYS DNA oligomers, 5'-CTAGTCGCTG CTGCTAGCGT CCGAGCGCGA CCAGTGAAAA ATGTCCGGGT AA-3' (point mutation underlined) (SEQ. I.D. NO. 32) and its complement including overhanging ends, 5'-CGCGTTACCC GGACATTTTT CACTGGTCGC GCTCGGACCG TAGCAGCAGC GA-3' (SEQ. I.D. NO. 33), were purified via acrylamide gel electrophoresis and phosphorylated as follows: oligomer (400 pmol), ATP (10 mM) and T4 oligonucleotide kinase (10 U) were incubated in 40 $\mu$l ligation buffer (BRL) at 37° C. for 1 hour, then heat inactivated at 65° C., for 2 min. The solutions were concentrated and 100 pmol of each oligomer was removed and combined in 20 $\mu$l of ligation buffer (BRL), heated to 70° C., and allowed to anneal over 2 hours.

(iii) Ligation of fragment replacement into digested vector. transformation and mutant plasmid isolation The digested vector (0.2 pmol), the annealed replacement (10 pmol) and T4 DNA ligase (10U) were combined in 20 $\mu$l of ligation buffer and incubated for 16 hours at 160°0 C. Also incubated was a negative control which contained all of the above except the annealed oligomer. The ligation mixture (5 Lll) was used directly for transformation into HB101 competent cells, via heat shock. The transformed cells were plated at various concentrations onto LB agar culture plates with 150 $\mu$g/ml of ampicillin and 200 $\mu$g of BCIP, and incubated overnight at 37° C. Several clones of blue colonies were picked and inoculated into 5 ml of LB media with 150 $\mu$g/ml of ampicillin and grown for 6 hours at 37° C. The mutant plasmid was isolated via standard plasmid isolation procedure (Maniatis, et. al., Molecular Cloning, Cold Spring Harbor Press, 1989).

(iv) Characterization of Desired Mutation

The plasmid was sequenced in the region of the mutation, ensuring the presence of the desired mutation and that no other mutations were present in the region of the oligomeric replacement. Upon confirmation of the mutation, the desired plasmid was then transformed into MZ13b cells, an *E. coli* strain lacking AP, and grown for protein isolation.

b. M13 Mutagenesis (i) Double digest of pUCphoA with restriction enzymes Bam HI and Hind III Four $\mu$g of plasmid, pUCphoA, was treated with restriction endonucleases Bam HI (10 U) and Hind III (10 U) in React #3 buffer (BRL) and incubated for 2 hours at 37° C. in a total of 40 $\mu$l. The reaction mixture was concentrated and applied to a 1% low-melting agarose gel and electrophoresed. The band corresponding to the cut AP gene (1454 bp) was excised from the gel and purified using a Prep-a-Gene kit (Bio-Rad).

(ii) Double digest of M13mp18 with restriction enzymes Bam HI and Hind III

Four $\mu$g of plasmid, M13mp18, was treated with restriction endonucleases Bam HI (10 U) and Hind III (10 U) in React #3 buffer (BRL) and incubated for 2 hours at 37° C. in a total of 40 $\mu$l. The reaction mixture was concentrated and applied to a 1% low-melting agarose gel and electrophoresed. The band corresponding to the cut vector was excised from the gel and purified using a Prep-a-Gene kit (Bio-Rad).

(iii) Ligation of phoA gene into digested M13mp18 vector and transformation

The digested vector (0.5 $\mu$g), the phoA gene (1 $\mu$g) and T4 DNA ligase (10 U) were combined in 10 $\mu$l of ligation buffer (BRL) and incubated for 16 hours at 160° C. The ligation mixture was diluted with 40 $\mu$l water and 1 $\mu$l of the diluted ligation mixture was used to transform competent DH5aF' cells. The transformed cells were plated with top agar along with 10 $\mu$l IPTG (100 mM), 50 $\mu$l 5-bromo-4-chloro-3-indolyl beta-D-galactopyranoside (X-gal, 2% in DMF) and 50 $\mu$l DH5aF' lawn cells and incubated overnight at 37° C. Negative controls consisting of: (1) Digested vector with no phoA gene; and (2) the phoA gene with no vector were also ligated and transformed. This resulted in many colorless plaques of M13mp18/phoA indicating successful ligation while there were no plaques in the negative controls.

(iv) Isolation and characterization of M13mp18/phoA phage and RF DNA

Two colorless plaques were picked and grown with 10 $\mu$l DH5aF' lawn cells at 37° C. in 5 ml of 2XYT (Maniatis, et. al., Molecular Cloning, Cold Spring Harbor Press, 1989) media for 16 hours. Cells and supernatant (phage) were separated via centrifugation followed by standard RF-plasmid preparation from the cells (Maniatis, et. al., Molecular Cloning, Cold Spring Harbor Press, 1989). Two mls of the phage supernatant were retained. Digest of the RF DNA with Bam HI and Hind III similar to the example described above revealed the presence of phoA gene in the M13 vector. The phage supernatant was titered vs. DH5aF' lawn cells and found to contain $5\times10^{11}$ pfu/ml.

(v) Preparation and isolation of uracil-containing M13mp18/PhoA phage (ssDNA)

One μl of M13mp18/phoA phage supernatant was added to a growing culture of 300 ml of CJ236 cells (Muta-Gene M13 In Vitro Mutagenesis Kit from Bio-Rad) with an $OD_{600}=0.3$ for a multiplicity of induction (moi) of 0.1 and allowed to grow for 6 hours at 37° C. The supernatant was retained, from which the phage and corresponding ssDNA was isolated using standard procedures (Maniatis, et. al., Molecular Cloning, Cold Spring Harbor Press, 1989). Two mls of the phage supernatant was retained and titered against both CJ236 and DH5aF' lawn cells. A $10^5$ difference in titer was determined, characteristic of excellent uracil incorporation. This resulting ssDNA was used for all mutagenic primer reactions.

(vi) Preparation of mutant pKJ9; Synthesis of mutagenic strand

A DNA oligomer, 5'-GTGCTCTTGG CTATCGCATT CGGAGTTCCC G-3', (SEQ. I.D. NO. 34) corresponding to the mutation GLU407CYS (underlined) (GLU407CYS denotes glutamic acid at residue 407 is replaced by cysteine), was phosphorylated as described above and diluted to 100 μl for a final concentration of 4 pmol/μl. One μl of the oligomer and 0.08 pmol of uracil-containing template were annealed and added to the polymerase reaction according to the Muta-Gene manual. The polymerase reaction was used to transform DH5aF' competent cells, as described above, except substituting BCIP for X-gal. A negative control (template but no mutagenic primer) produced 4 blue plaques while the mutagenic reaction resulted in hundreds of blue plaques.

(vii) Isolation and sequencing of mutant phage and RF DNA

Several blue plaques were picked and grown with 20 μl DH5aF' lawn cells in 3 ml of 2XYT media for 6 hours at 37° C., followed by standard isolation of ssDNA from the supernatant and RF DNA from the cells. Sequencing of the ssDNA identified clones containing the desired mutation. The RF DNA corresponding to the correct mutant was digested with Bam HI and Hind III and the mutant phoA gene was isolated as described above.

(viii) Ligation of mutant PhoA gene into pUC18

The plasmid pUC18 was digested with Bam HI and Hind III and purified, similarly to the procedure described above. The mutant phoA gene was ligated into the cut vector using procedures already described. The ligation mixture was used to transform MZ13b cells directly for protein expression.

Example 9

Growth and Extraction of Hybrid Enzyme

Following introduction of the mutant plasmid into the *E. coli* strain MZ13b, the strain was grown overnight in 2 liters of LB media with 200 μg/ml of ampicillin at 37° C. The cells were collected via centrifugation and then resuspended in 20 ml of buffer (0.15M Tris-HCl, 0.9% NaCl, pH 6.6). Since the hybrid enzyme was exported into the periplasm, spheroplasting liberated the periplasmic proteins. The suspended cells were treated with 120 mg of polymyxin B (6 mg/ml) and were incubated at 37° C. for 15 min. The supernatant was separated from cellular debris by centrifugation and filtered through a 0.2 mm filter.

Example 10

Purification of Hybrid Enzymes a) Protection of Surface Sulfhydryl Group or "Capping"

The sulfhydryl groups intended for conjugation were exposed in the crude hybrid enzyme extract and therefore subject to oxidation or other undesired reactions. The introduced cysteine at the surface of the hybrid enzyme was oxidized as a disulfide to many different sulfur containing cellular components. In order to prepare a homogenenous state of these adducts, the hybrid enzyme was reduced and then reacted with another sulfhydryl group. The cell extract was treated with DTT (final concentration of 2 mM) for 20 min. at room temperature. Cysteine was added to a final concentration of 10 mM and oxygen was bubbled through the mixture for 2–6 hours. Similar conditions were used for other sulfhydryl containing compounds such as cysteamine, 2-mercaptoethanol, 3-mercaptopropionic acid, glutathione, or thiosalicylic acid, etc. Alternatively, an activated thiol could be introduced following reduction. The reduced mixture was treated with Ellman's reagent [or 2,2'-dithiopyridine, 5,5'-dithiobis(2-nitrobenzoic acid), or dithiosalicylic acid, etc.] for 1 hour at room temperature.

b) Purification of Hybrid Enzymes

The extract containing the capped hybrid enzyme was diluted to 1 liter with deionized water and applied via peristaltic pump to a column of DEAE-Sepharose equilibrated with 25 mM Tris-HCl, 1 mM MgCl2, pH 8.0. The column was washed with 50 mM NaCl in 25 mM Tris-HCl, 1 mM MgCl2, pH 8.0 until equilibrated. Elution of the active protein was accomplished with a 50–200 mM NaCl gradient in 25 mM Tris-HCl, 1 mM MgCl2, pH 8.0. Active fractions were eluted with 80–120 mM salt. The purified hybrid enzyme was characterized by both $A_{280}$ nm for protein and $A_{410}$ nm for enzyme using standard techniques. The active fractions were combined and concentrated using ultrafiltration.

At this point, the hybrid enzyme was of sufficient purity for chemical derivatization. Further purification to homogeneity for specific activity measurements was accomplished using HPLC. The concentrated solution (1–2 mg/ml protein) was injected onto a POROS R/H reverse phase HPLC column and eluted with a 0–80% acetonitrile gradient in 50 mM Tris-HCl, 1 mM MgCl2, pH 8.0 over 20 min. The hybrid enzyme eluted in 11 min. with approximately 30% acetonitrile. Identical conditions were used to purify chemically conjugated hybrid enzyme.

Twelve hybrid enzymes were prepared in this manner. The hybrid enzymes were measured for specific activity and attenuation (percent loss of activity upon antibody binding following chemical conjugation) and these data are presented in Table 4. Lower case "p" is used to designate plasmid while "KJ" are arbitrary alphabets. The number following "KJ" represents the sequential preparation of the mutants. The abbreviation "pUC" refers to the initial vector, commercial plasmid pUC18, before the insertion of the expressed gene. For example, pKJ3.pUC denotes the plasmid encoding for hybrid enzyme 3, inserted into the commercial plasmid pUC18. The corresponding hybrid enzyme resulting from pKJ3.pUC, for example, is APKJ3. Standard convention is also used in, for example, "Lys167Cys" which refers to the mutation of AP residue Lysine-167 replaced by cysteine in APKJ3.

TABLE 4

Hybrid-enzymes, specific activities and attenuations.

| PLASMID | MUTATION | REL.ACT.* | % PROTEIN† | % ATT** |
|---|---|---|---|---|
| AP | — | 1 | 70 | — |
| pKJ1.pUC | Asp261Cys | .34 | 10 | 60 |
| pKJ2.pUC | Asn263Cys | .36 | <1 | ND |
| pKJ3.pUC | Lys167Cys | .80 | 40 | 62 |
| pKJ4.pUC | Lys177Cys | .74 | 30 | 76 |
| pKJ5.pUC | Lys328Cys | .63 | 50 | 58 |
| pKJ6.pUC | Lys209Cys | .45 | ND | 33 |
| pKJ7.pUC | Gln291Cys | .43 | ND | 21 |
| pKJ8.pUC | Asp294Cys | ND | 10 | ND |
| pKJ9.pUC | Glu407Cys | ND | 20 | 37 |
| pKJ10.pUC | Asp408Cys | ND | 20 | 55 |
| pKJ11.pUC | Asp380Cys | ND | 10 | 45 |
| pKJ12.pUC | Asp117Cys | ND | ND | ND |

*activity relative to AP (60 U/mg in the buffer described).
†percent of crude extract which is AP.
**% attenuation is how much enzymatic activity is decreased upon antibody binding.
ND = Not Determined Example 11

General Method for Conjugating a Ligand to a Hybrid Enzyme

Conditions for conjugation reactions were dictated by the cross-linker of interest. Preferably, one activates a ligand by using a heterobifunctional cross-linker with N-hydroxysuccinimidyl and iodoacetamide groups at either ends. The ligand was treated with the linker first in an alkaline buffer to allow reaction of the N-hydroxysuccinimido group with the amino function(s) on the peptide. Following purification by chromatography or crystalization, the resulting activated ligand was then allowed to react at neutral pH, preferably with a hybrid enzyme with the cysteine (Cys) substitution close to its active site. The resulting hybrid enzyme-ligand conjugate was generally purified by passage through a desalting column to remove excess and unreacted ligand and other undesirable salts and ions. The material can be further purified by passing through an affinity column containing immobilized anti-ligand antibodies. The unconjugated hybrid enzyme passed directly through the column, while the hybrid enzyme-ligand conjugate was retained. The retained hybrid enzyme-ligand conjugate was subsequently eluted off the column with chaotropic solvents or other specific eluents.

The hybrid enzyme-ligand conjugates were assessed in terms of their performance in an assay. Basically, a mixture which consisted of the hybrid enzyme-ligand conjugate, the specific antibody and the specimen containing the analyte was incubated. It is to be understood that the mixing of components can be sequential or simultaneous. An enzyme substrate was then added, and photometric changes associated with the enzyme reaction was measured. The substrate concentration was generally from 1 $\mu$M to 50 mM, although a range of 0.2–10 mM was preferred. The general concentration range of the conjugate was 10 ng/ml to 1 mg/ml while the preferred range was 1–10 $\mu$g/ml. The general range for antibody concentration is 1 ng/ml to 50 $\mu$g/ml with the preferred range as 1 to 50 $\mu$g/ml. A suitable buffer depends on the enzyme of interest and conditions optimal for enzymatic activity. Typically the incubation temperature is from about 10° C. to about 45° C. except where room temperature is used for the incubation prior to the addition of substrate and 37° C. for the enzymatic reaction. Incubation times can range from 1 min. to overnight for the immunochemical binding and up to 30 min. for the enzymatic reaction. The preferred time of incubation is 10 min. for the immunochemical binding and 10 min. for the enzymatic reaction. The substrate used can be for ultraviolet, visible, fluorescence, phosphorescence, luminescence or electrochemical detection.

Figure 16B:
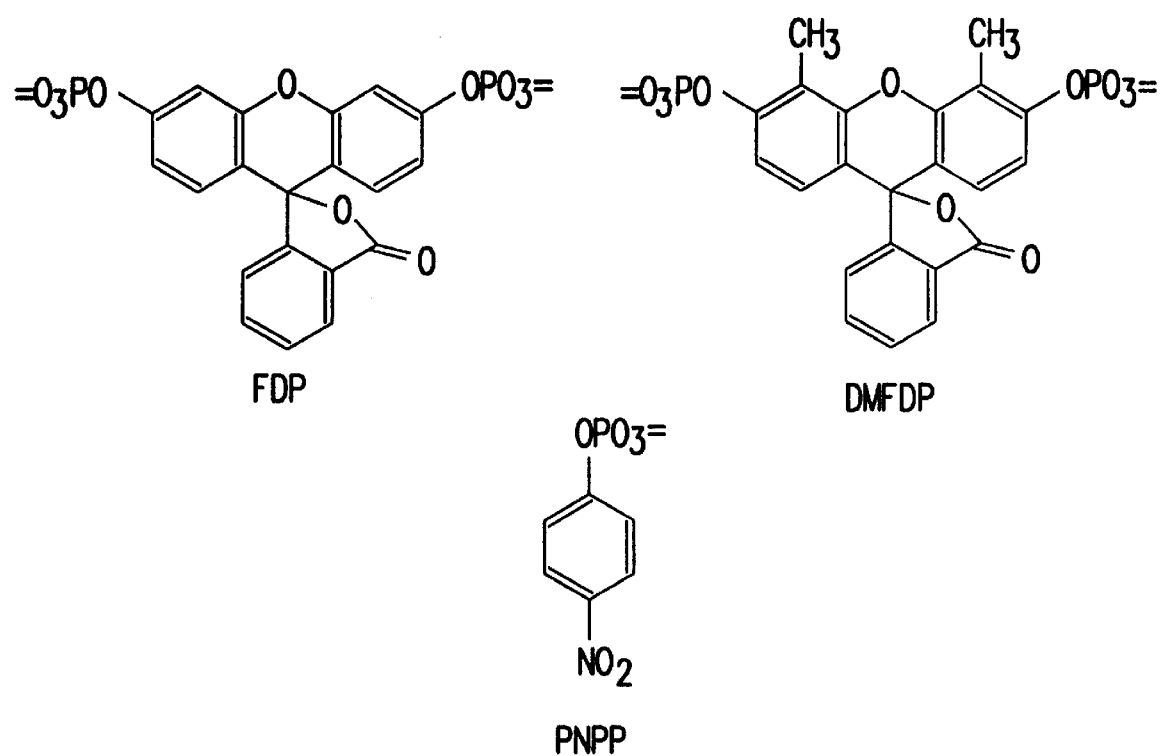
FIG. 16 shows the structure formulas of ligand derivatives. $T_n$ refers to theophylline derivatives differing in the number of methylenes in the linker arm; Thy refers to thyroxine derivatives and ThyA, ThyB, and ThyC represent different numbers of methylenes in the linker arm; D represents Digoxigenin and DA, DB, DC represent different numbers of methylenes in the linker arm; FDP, DMFDP, and PNPP are various substrates of AP.

Conjugation of ligand to the hybrid enzyme was accomplished by exposing an aqueous solution of the deprotected enzyme to a derivative of the ligand containing a functional group which formed a covalent bond with the sulfur of a sulfhydryl group. Most preferable was the iodoacetamide or maleimide derivative of the ligand. Structures of some of these derivatives are shown in FIG. 16. The reactive group attached to the hybrid enzyme at the strategically located sulfhydryl group and formed a stable covalent bond. In the conjugation procedure a large excess of the activated ligand was dissolved in a solvent, preferably dimethylformamide, which maintained the ligand derivative. The activated ligand must be present in molar excess over the hybrid enzyme and the deprotecting agent. This solution was then added to the freshly deprotected hybrid enzyme solution. The time required for complete reaction depended primarily on which hybrid enzyme was used. For APKJ3, the reaction was complete within 15 min. whereas up to 6 hours could be required for APKJ4. The mixture was then passed through a gel filtration column to remove organic solvent and excess ligand derivative. The protein concentration was measured with Coomassie Blue (Pierce) protein reagent.

Conjugation of the purified hybrid enzyme to an iodoacetamide-ligand was performed at room temperature. 10 $\mu$L of 100 mM DTT was added to 1 ml of the purified hybrid enzyme. The DTT was dissolved into 0.1M Tris (pH 7.5). This mixture was allowed to react for 3–4 hours and after the reaction, 100 $\mu$L of a DMF solution of 500 mM ligand-iodoacetamide component was added (e.g. aminomethyl theophylline iodoacetamide or aminopropyltheophylline iodoacetamide). The length of the linker arm can vary depending on the distance of the mutation from the active site. Typically, this reaction took approximately 30 min. at room temperature, and was then passed through a desalting column to remove the excess ligand-iodoacetamide. The buffer used in this column was generally 50 mM Tris and 1 mM $MgCl_2$ (pH 7.5). The high protein fractions were combined and the protein concentration was determined by an $A_{594}$ nm reading using the Coomassie Assay (Pierce). This conjugate was then used at 0.15 $\mu$g/ml (or 0.1 absorbance units on an analyzer such as the Cobas Mira, Roche Diagnostics, Montclair, N.J.). The dilution buffer was 0.1M Tris, 1mM $MgCl_2$, 0.1 mM $ZnCl_2$, and 0.5% BSA (pH 7.5).

Example 12

General Method for Evaluating a Hybrid Enzyme-Ligand Conjugate

Figure 17:
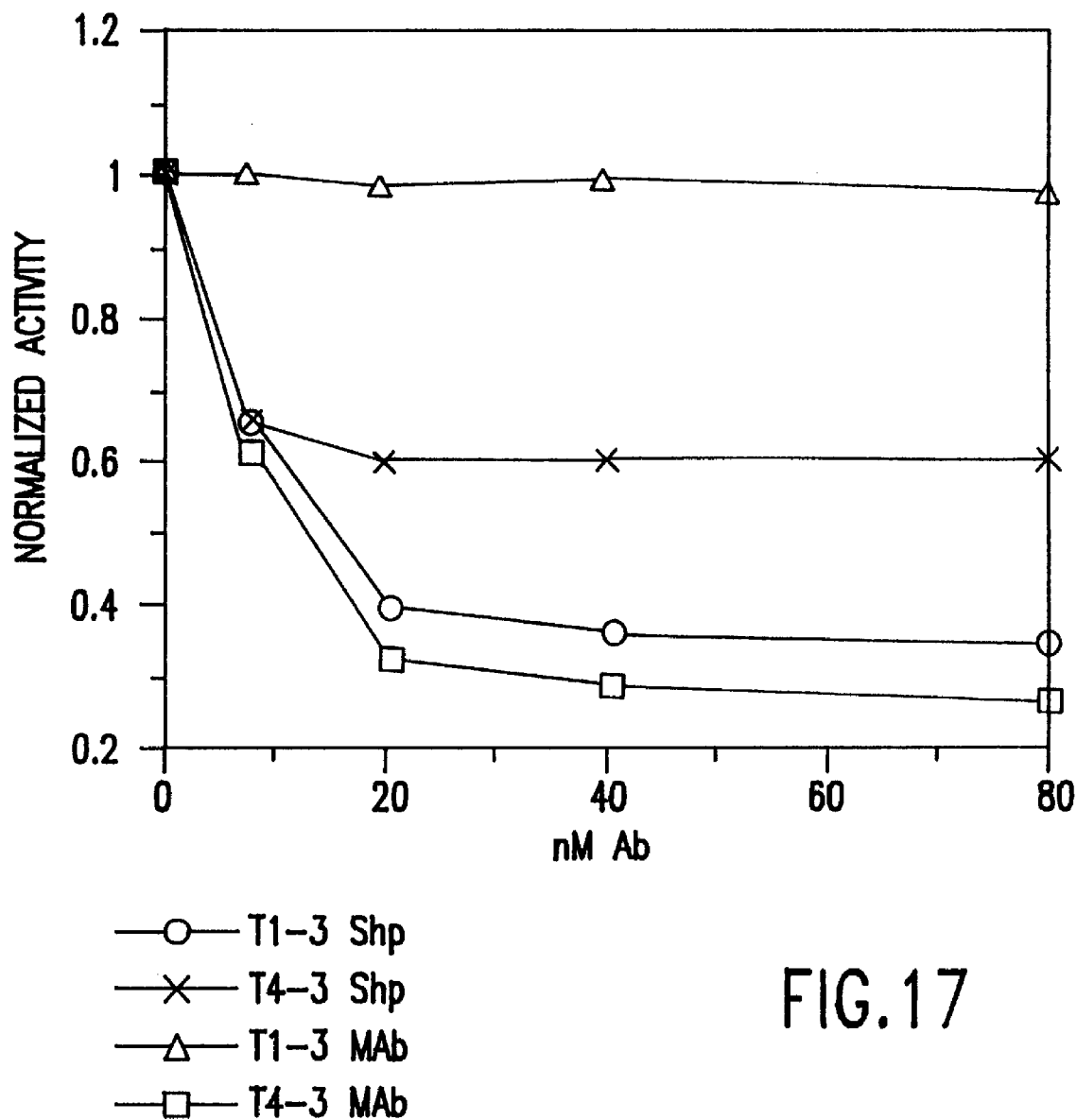
FIG. 17 shows the resultant enzyme activities of theophylline hybrid enzyme-ligand conjugates.
Figure 18A:
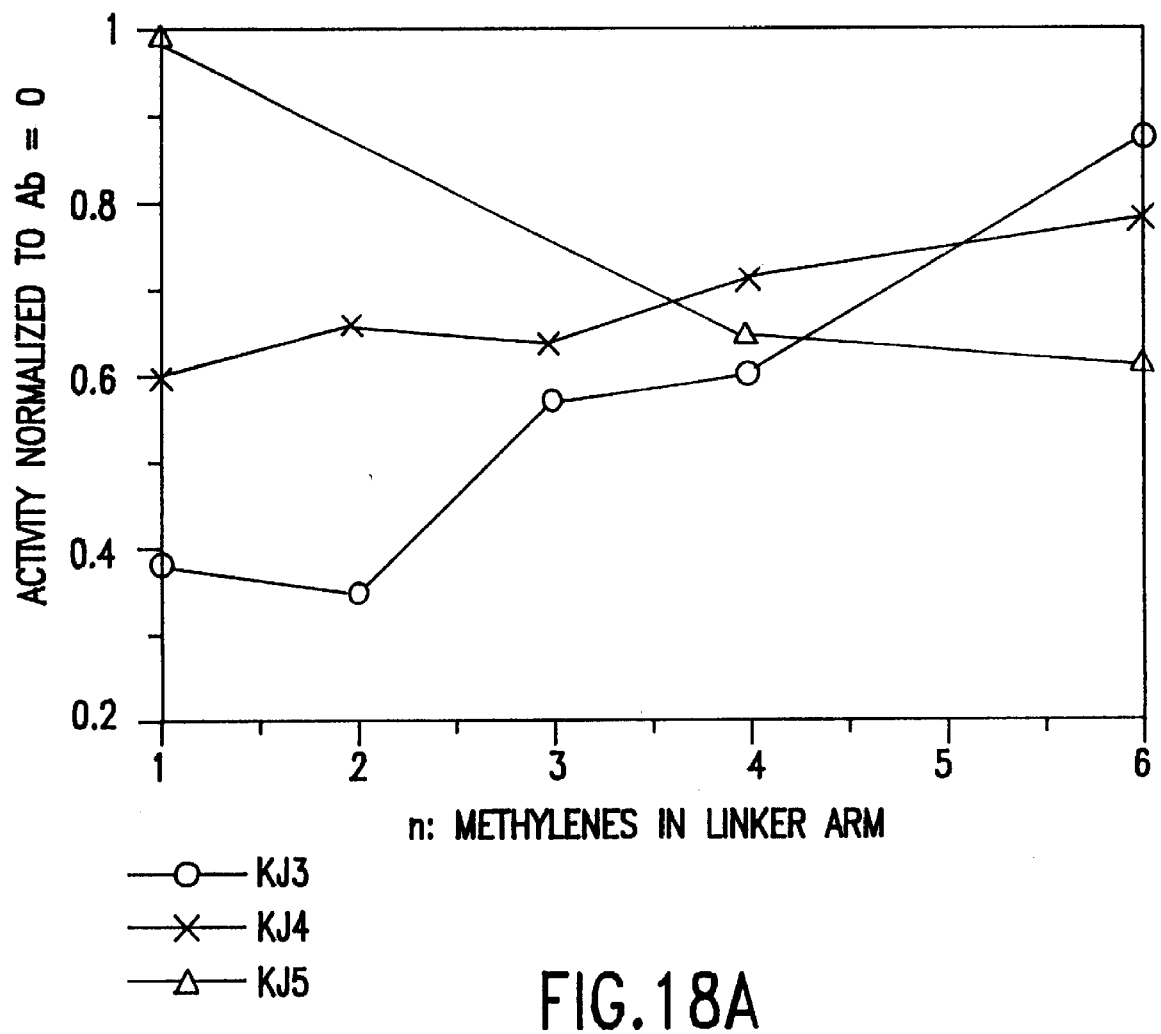
FIG. 18A and B shows the residual enzymatic activity in the presence of saturating amounts of antibody for hybrid enzyme-ligand conjugates in which theophylline derivatives are attached at different positions on the hybrid enzymes through linker groups of various lengths.
Figure 18B:
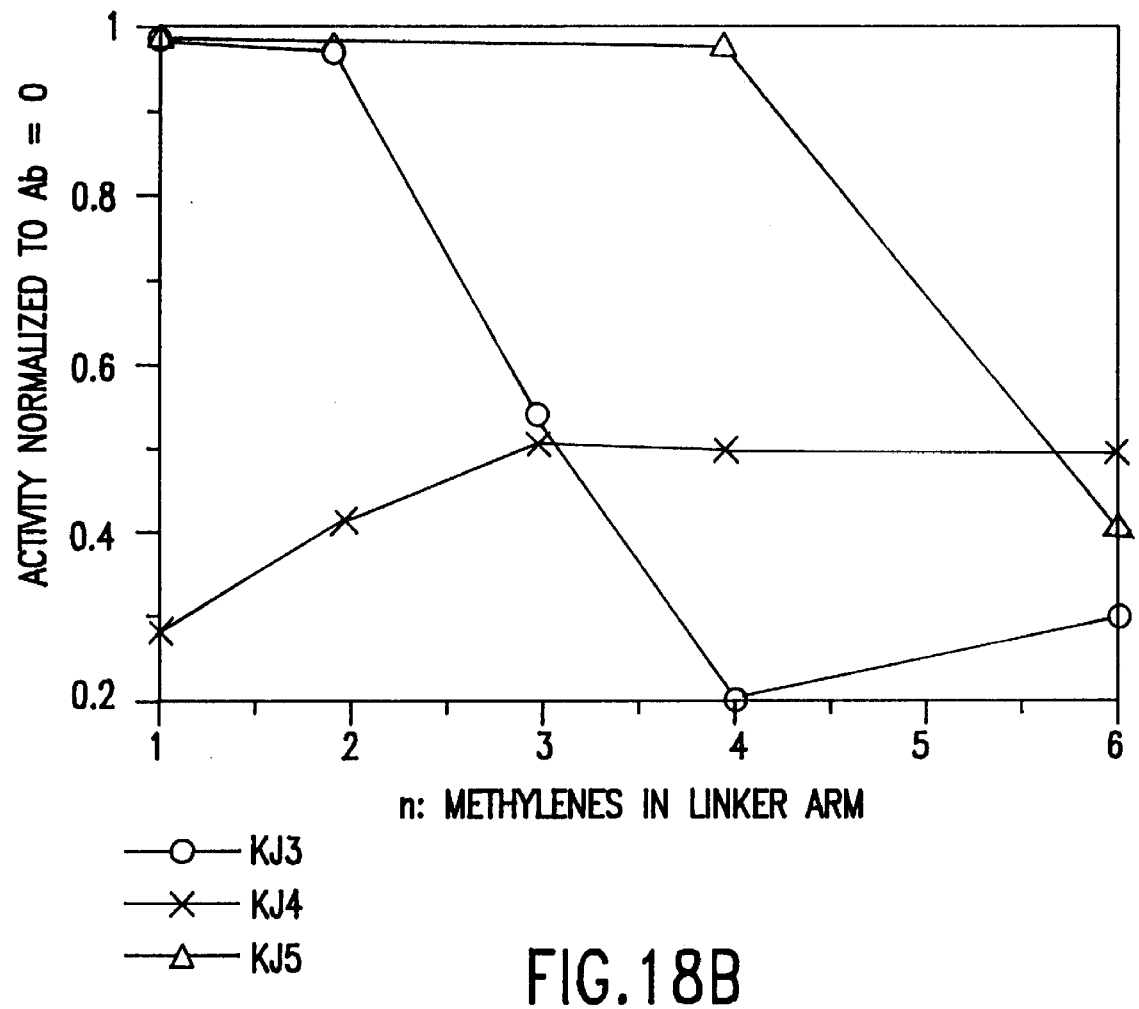
FIG. 18B shows the effect of mouse monoclonal antibodies.
Figure 19:
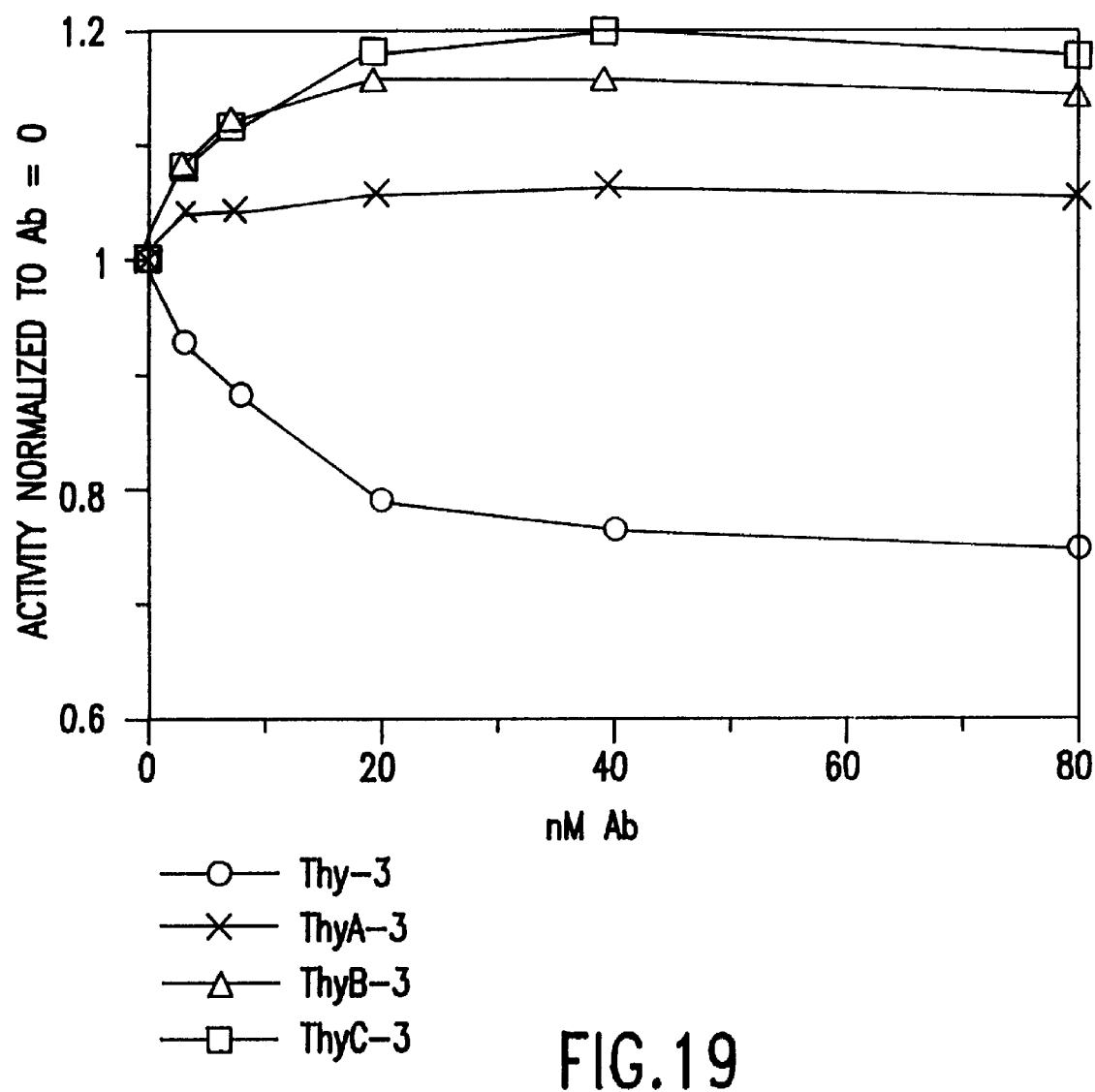
FIG. 19 shows the effect of adding a monoclonal antibody to hybrid enzyme-ligand conjugates with thyroxine derivatives as the ligand with various methylene linker groups. Thy-3, ThyA-3, ThyB-3, and ThyC-3 refer to various thyroxine derivatives conjugated to APKJ3.

After preparation, the hybrid enzyme-ligand conjugates were tested with specific antibodies to determine the degree to which the antibodies could affect enzymatic activity. FIG. 17 shows results for hybrid enzyme APKJ3, conjugated to theophylline derivatives T1 and T4. The hybrid enzyme-ligand conjugates were tested with both sheep polyclonal antibody and mouse monoclonal antibody to theophylline. While the general trend was for antibody to attenuate the activity of the hybrid enzyme-ligand conjugate, significant differences were apparent between the different hybrid enzyme-ligand conjugates and between the different antibodies to the same hybrid enzyme-ligand conjugates. The enzymatic activity decreased with added antibody until the concentration of antibody was approximately equal to that of the hybrid enzyme-ligand conjugate, after which no further decrease in activity occurred. Since both antibody and hybrid enzyme-ligand conjugate were divalent, the observed 1 to 1 stoichiometry was expected. The degree of attenuation of enzymatic activity at saturating antibody was a characteristic dependent on structural features of both the antibody and the hybrid enzyme-ligand conjugate. FIGS. 18A and 18B show the residual enzymatic activity in the presence of a saturating amount of antibody for hybrid enzyme-ligand conjugates in which theophylline derivatives were attached through linker groups of various lengths at three different positions on the hybrid enzyme-ligand conjugate. The hybrid enzyme APKJ5 has the linking group positioned most deeply in the active site cleft. Hybrid enzyme APKJ3 has the linking group at an intermediate position, and hybrid enzyme APKJ4 has the linking group near the opening of the cleft. FIGS. 18A shows results for sheep polyclonal and mouse monoclonal antibodies.

It was apparent from the plot that antibody attenuates hybrid enzyme-ligand conjugate activity only when the linker group placed the theophylline group at a sufficient distance from the active site. Hybrid enzyme-ligand conjugate APKJ5's binding site was deepest in the active site cleft and required the longest linker arms. Hybrid enzyme-ligand conjugate APKJ3 required intermediate length linkers and hybrid enzyme-ligand conjugate APKJ4 showed antibody attenuation with the shortest linkers. Interestingly, sheep polyclonal antibody attenuated the activity of hybrid enzyme-ligand conjugates with shorter linker groups than mouse monoclonal antibody. This appeared to be an effect of the species from which the antibody was obtained, rather than a peculiarity of the monoclonal antibody used, since the same dependence was observed with other ligands and a variety of antibodies.

The linker length results were consistent with the model for the system of the present invention. According to the model, steric interference of the bulk of the antibody prevents substrate from gaining access to the enzyme active site. When the ligand was located too deeply within the active site cleft, antibody could not bind due to its own steric bulk. When the ligand was located too far out from the active site cleft, antibody was bound too far from the hybrid enzyme to greatly restrict access of substrate. An optimal distance was achieved which allowed binding of antibody and resulted in maximal attenuation. Further support for the model was seen by comparing results with different substrates other than PNPP, a small molecule and the usual substrate for AP. The restricting effect of antibody binding to hybrid enzyme-ligand conjugate could be more pronounced with a larger substrate.

Table 5 shows the residual activity of theophylline hybrid enzyme-ligand conjugates (theophylline as the ligand) at saturating antibody concentrations using different substrates: 4-nitro-phenyl phosphate (PNPP); fluorescein diphosphate (FDP); and dimethyl-fluorescein diphosphate (DMFDP). It was apparent that FDP, which is larger than PNPP gave significantly greater attenuation. The largest substrate DMFDP, showed the most attenuation. The numbers listed in Table 5 are percentages of the control (without antibody=1).

TABLE 5

| | PNPP | FDP | DMFDP |
|---|---|---|---|
| Sheep Ab | | | |
| T1-3 | 0.37 | 0.27 | 0.12 |
| T1-4 | 0.56 | 0.55 | 0.40 |
| T4-3 | 0.56 | 0.39 | |
| T4-4 | 0.73 | 0.62 | |
| Mouse Monoclonal Ab | | | |
| T1-3 | 1.00 | 1.00 | 0.94 |
| T1-4 | 0.28 | 0.20 | 0.18 |
| T4-3 | 0.21 | 0.10 | |
| T4-4 | 0.48 | 0.31 | |

AB = Antibody

Modulation does not always mean attenuation. FIG. 19 shows the effect of a monoclonal antibody added to hybrid enzyme APKJ3 (20 pM) with thyroxine derivatives as ligand with various linker groups in the presence of PNPP at pH 8.0. The hybrid enzyme-ligand conjugate with the shortest linker, Thy-3, showed the normal decrease in activity on addition of antibody. Hybrid enzyme-ligand conjugates with longer linkers, ThyA-3, ThyB-3, ThyC-3, showed an increase in activity on addition of antibody. This antibody-enhancement of activity was also seen with fluorescein as the ligand of APKJ3 using a monoclonal antibody to fluorescein. Some hybrid enzyme-ligand conjugates' enzymatic activity in the absence of antibody was less than in the presence of antibody, which showed antibody-attenuation. This indicated that the thyroxine (or fluorescein) ligand itself interfered with the active site of the hybrid enzyme-ligand conjugate, and that the interference was removed by the binding of antibody to the ligand. Thyroxine and fluorescein were the only ligands tested which contained phenolic hydroxyl groups. Hydrogen bonds between phenolin hydroxyl groups and the reactive groups at the catalytic center could be responsible for the decreased activity.

In an immunoassay, antibody-induced attenuation of the enzymatic activity must be affected by the presence of an analyte. FIG. 20 shows the effect of adding $\mu$l quantities of serum-based theophylline calibrators to a theophylline hybrid enzyme-ligand conjugate (T1-3, 20 mM) in the presence of various concentrations of sheep antibody. T1-3 denotes hybrid enzyme APKJ3 conjugated to T1 (aminomethyltheophyline). In the absence of antibody, the enzymatic activity was high regardless of the theophylline concentration. Addition of antibody decreased the activity at zero theophylline until saturating antibody concentration was achieved. The addition of theophylline restored enzymatic activity in a dose-responsive fashion, with maximal activity restored similar to that seen in the absence of antibody.

For use in an assay format, sample volume and concentrations of antibody and hybrid enzyme-ligand conjugate were chosen to give the desired sensitivity. Components were mixed preferably as follows, sample and binding molecule were combined and incubated for 0 to 30 min. and then hybrid enzyme-ligand conjugate was added and the mixture incubated from 0 to 30 min. Substrate was added and the reaction monitored from 5 sec to 30 min. The assay was calibrated with solutions containing known concentrations of the analyte. Sample of unknowns were run by the assay procedure and their analyte concentrations determined by comparing signals with a curve determined from the results of the calibrators.

Example 13

General Preparation of a Ligand Containing a Linker Group

Generally, the iodoacetamide function was convenient for conjugation of the ligand to the hybrid enzyme. Starting with the appropriate amine derivative of the ligand, the corresponding iodoacetamide was easily prepared by exposure to either iodoacetic anhydride or to an active ester (preferably the N-hydroxysuccinimide ester) of iodoacetic acid under basic conditions, preferably in methanol or aqueous methanol. Since the iodoacetamide of the ligand was generally less soluble in aqueous solutions than the amine, the product can frequently be isolated by precipitation from the reaction mixture, though purification by chromatography may be necessary in some cases. To prepare ligands in which the linker group was located farther from the available amine than would be the case using the simple iodoacetamide, an extended form of the iodoacetamide active ester could be used. To prepare one such extended linker, the N-hydroxysuccinimide ester of iodoacetic acid was exposed to glycine to prepare the N-iodoacetamide of glycine. The carboxylate group of the compound was then re-esterified with the same N-hydroxysuccinimide. Homologs of glycine (for example, beta alanine, gamma aminobutyric acid) or dimers or multimers of these could be used to give longer linker arms. In addition, other amino acids could be used in which a side chain was present to confer some desired solubility or activity characteristic to the linker molecule. Because of the simplicity of the reactions used in preparation of these activated ligands, thin layer chromatography (TLC) was adequate to determine the identity and purity of most products.

Example 14A

Preparation of 8-Aminoethyltheophylline iodoacetamide (T2)

a. 8-N-tBOC-Aminoethyltheophylline 3.4 g (20 mmole) of 5,6-diamino-1,3-dimethyl uracil hydrate and 5.0 g (26 mmole) of N-tBOC-beta alanine were mixed together in a flask and placed in an oil bath which was heated for over 30 min. to 155° C. The solid melted at 40° C., and bubbling occurred over 100° C. Reaction progress was followed by thin layer chromatography on silica gel using a chloroform: methanol: acetic acid solvent (50:4:2). After 20 min. at 155° C. the reaction appeared complete. The mixture was cooled, dissolved in 35 mls water with 10 mls 6N NaOH, and heated to reflux for 20 min. TLC showed complete conversion to the theophylline derivative. The solution was titrated with 6N HCl. A heavy precipitate formed with addition of 6 mls HCl and 50 mls water was added. An additional 3 mls HCl was added to bring pH to 5.85. The solid was collected by filtration, dissolved in 50 mls water with 3 mls 6N NaOH and reprecipitated with 3 mls of 6N HCl. The solid was collected by filtration and dried to 3.8 g of a light yellow powder.

b. 8-Aminoethyltheophylline hydrochloride 3.23 g of the above product was dissolved in 120 mls of refluxing ethanol. A small amount of the material was insoluble and was discarded. 3 mls of concentrated HCl was added and the mixture was heated near reflux approximately 60 min. and then allowed to cool to room temperature. The solid was collected by filtration and washed with 20 mls of ethanol and dried to 2.11 g of off-white crystals.

c. 8-Aminoethyltheophylline iodoacetamide 125 mg (0.5 mmole) of the above crystals were mostly dissolved in 1.0 ml of water, 4.0 mls of methanol and 0.12 mls of 6N NaOH, pH 10.18. 130 mg of iodoacetic anhydride was added while stirring rapidly. The pH decreased to 5.6 over 5 min., during which the solution cleared and then a new precipitate formed. NaOH was added to hold the pH between 7.0 and 7.5 during which an additional 64 mg of iodoacetic anhydride was added. 10 mls of water was added and the solid collected by filtration, washed with 10 mls of water and dried to a 123 mg solid.

Example 14B

Preparation of 8-Aminomethyltheophylline iodoacetamide (T1)

a. 8-N-t-BOC-Aminomethyltheophylline 8.5 g of N-t-BOC glycine and 8.5 g 5,6-diamino-1,3-dimethyluracil were ground together in a mortar. The powder was transferred to a flask which was placed in an oil bath and rotated while raising the temperature gradually to 130° C. After 30 min. at 130° C., the resulting thick syrup was cooled to a brittle glass. 20 mls of 6N NaOH was added and the solid dissolved by heating to reflux. The thick precipitate which formed on cooling was dissolved on addition of 80 mls water. The pH was adjusted to 6.4 with 10 mls of concentrated HCl (precipitate formed at pH 9.8). The solid was collected by filtration, washed with 150 mls of water and dried in a vacuum desiccator to 8.37 g of a light yellow powder.

Other 8-N-t-BOC-aminoalkyltheophyllines were prepared by the same procedure. Variations included reaction temperatures up to 155° C. and heating times up to 60 min. In some cases a larger quantity of more dilute NaOH was used. The yield for this reaction was never more than about 60% of theoretical.

b. 8-Aminomethyltheophylline hydrochloride 7.73 g of 8-N-t-BOC-aminomethyltheophylline was heated to reflux in 50 mls ethanol, 6 mls of concentrated HCl and 15 mls of water for 30 min., and occasionally blowing vapor from top of flask. A precipitate formed on addition of 50 mls ethanol and was dissolved on addition of 5 mls of water. The mixture was allowed to cool to room temperature then to 0° C. in an ice bath. 50 mls of ethanol was added to thin the mixture to enable pouring. The solid was collected by filtration and washed with 50 mls of ethanol and dried to 5.50 g of white crystals.

Other 8-aminoalkyltheophylline hydrochlorides were prepared by the same procedure. The product corresponding to T4 did not precipitate from ethanol/HCl, so the mixture was made basic by addition of ammonium hydroxide. The solid which formed was collected by filtration.

c. Iodoacetic acid N-hydroxysuccinimide ester solution 190 mg of iodoacetic acid and 120 mg of N-hydroxysuccinimide were dissolved in 600 $\mu$l of dimethylformamide. 210 mg of dicyclohexylcarbodiimide was dissolved in 400 $\mu$l of dimethylformamide and added to the above. The mixture was agitated by vortex mixing and then incubated at room temperature for 60 min. The mixture was centrifuged to sediment diclohexylurea. The supernate was used without further purification.

d. 8-Aminomethyltheophylline iodoacetamide 117 mg of 8-Aminomethyltheophylline hydrochloride was dissolved in 10 mls of methanol, and the pH was adjusted to 11.25 by addition of approximately 170 $\mu$l of 6N NaOH. While stirring rapidly 700 $\mu$l of iodoacetic acid N-hydroxysuccinimide ester solution was added and the pH rapidly decreased to 8.25. 100 $\mu$l of 6N HCl was added to the solution. A heavy precipitate formed and was collected by filtration, washed with water and methanol, and dried to 107 mg of white solid.

Other 8-Aminoalkyltheophylline iodoacetamides were prepared the same way, though in some cases, iodoacetic anhydride was used. The N-hydroxysuccinimide ester was preferred as it was expected to undergo less solvolysis under the reaction conditions. In some cases the product did not precipitate from the methanol/water wash, but solid was collected on evaporation of the methanol.

All these reactions were conveniently monitored by TLC on silica gel plates using a solvent system consisting of chloroform:methanol:acetic acid 50:4:2 or 50:8:2, depending on the polarity of the reactants and products.

Example 15A

Preparation of Thyroxine-N-iodoacetamide (Thy)

78 mg (0.1 mmole) of L-thyroxine was dissolved in 1.0 ml of methanol on addition of 34 mls (0.2 mmole) of 6N NaOH and sonication in a bath sonicator. 48 mg of iodoacetic acid N-hydroxysuccinimide ester was added and the mixture vortexed. 8.5 mls of 6N NaOH was added and the mixture vortexed. TLC (chloroform:methanol:acetic acid 50:6:2 on silica gel) indicated complete reaction. 50 mls of 6N HCl was added and then 4 mls of water and formed a precipitate. The precipitate was collected by centrifugation and washed with 1 ml of methanol and 4 mls of water. After centrifugation the pellet was dried under vacuum to 82 mg of an off-white solid.

Example 15B

Preparation of Thyroxine-N-(glycyl-N-iodoacetamide) (ThyA)

a. N-Glycylthyroxine 380 mg of L-Thyroxine was dissolved in 2.0 mls of methanol on addition of 174.5 $\mu$l of 6N NaOH and sonication. 140 mg of N-t-BOC-Glycine-N-hydroxysuccinimide ester was added and the mixture vortexed. TLC indicated complete reaction within 10 min. 190 $\mu$l of 6N HCl and 5 mls of water were added and the mixture vortexed. The sticky precipitate was separated from the mixture with 3 extractions of 3 mls of chloroform. The organic fractions were dried with anhydrous sodium sulfate and the solvent stripped off, leaving 470 mg of an off-white solid. This was dissolved in 2 mls of methylene chloride and 2 mls of trifluoroacetic acid. After 10 min., the solvent was stripped off and the residue dissolved in 5 mls of methanol. The solvent was stripped off, leaving 500 mg of a light brown solid.

b. Thyroxine-N-(glycyl-N-iodoacetamide)

95 mg of N-Glycylthyroxine was dissolved in 1.0 ml of methanol with 51 $\mu$l of 6N NaOH. (This was one molar equivalent more NaOH than expected which indicated that the N-glycilthyroxine used was present as the trifluoroacetate salt.) 61 mg of Iodoacetic acid N-hydroxsysuccinimide ester and 8.5 $\mu$l of 6N NaOH was added. TLC showed a complete reaction. 60 mls of 6N HCl was added, followed by 4 mls of water. After centrifugation, the supernate was discarded and the precipitate dispersed with 1 ml of methanol and was washed with 4 mls of water. The mixture was again centrifuged and the pellet dried in a vacuum desiccator, yielding 79 mg of a white solid.

The ligands corresponding to ThyB and ThyC were prepared in the same manner as Thy, with the exception that N-iodoacetyl-beta-alanine N-hydroxysuccinimide ester and N-iodoacetyl-gamma-aminobutyric acid N-hydroxysuccinimide ester were used in place of iodoacetic acid N-hydroxysuccinimide ester. Similar yields were obtained using the same reaction conditions.

Example 16A

Preparation of Iodoacetamido-B-alanineamido-3-aminodigoxigenin (DA)

92 mg (0.25 mmole) of 3 aminodigoxigenin was dissolved in 1.0 ml of methanol. 91 mg of N-iodoacetamido-B-alanine N-hydroxysucinnimide ester and 15 mls of triethylamine were added and after 20 min., thin layer chromatography showed a complete reaction. The mixture was partitioned between 30 mls of 10% sodium carbonate and 3×10 mls of chloroform (5 mls of methanol was added in the first extraction step to prevent formation of a sticky oil). The chloroform layers were combined, dried with anhydrous sodium sulfate, and evaporated to 150 mg film on the flask. This was dissolved in 0.2 mls of methanol and 2 mls of chloroform, and applied to a TLC plate, in chloroform:methanol:acetic acid (100:12:2) solvent. The band containing the desired product, at rf=0.5, was scraped off the plate, eluted with methanol, and the solvent evaporated leaving 100 mg of a waxy solid.

Example 16B

Preparation of Digoxigenin Ligands a. 3-Ketodigoxigenin

Platinum IV oxide (0.5 g) was added to 1.0 g of Digoxigenin and dissolved in 100 mls of water and 150 mls of acetone. The mixture was pressurized to 2 atmospheres of oxygen and shaken for catalyst was filtered off, and the solvent stripped off leaving 1.01 g of white solid. This was dissolved in 100 mls of methylene chloride and extracted with 70 mls of water. The water was back-washed with two volumes of 50 mls of methylene chloride. The organic fractions were collected, dried with anhydrous sodium sulfate and the solvent was stripped off leaving 0.75 g of white solid.

b. 3-Aminodigoxigenin 300 mg of 3-ketodigoxigenin was dissolved in 20 mls of methanol with gentle heating. 2.0 g of ammonium acetate was added and the solution was cooled in an ice bath, and 90 mg of sodium cyanoborohydride was added while being stirred. TLC showed a complete reaction within 5 min. While cooling the mixture in ice, 102 drops of concentrated HCl was added to acidify the mixture according to pH paper. 600 mg of solid was filtered off and the pH of the filtrate was adjusted to 10.5 with 20% potassium hydroxide (KOH). The mixture was extracted with 3 volumes of 30 mls of chloroform. The organic fractions were dried with anhydrous sodium sulfate and the solvent stripped off, yielding 304 mg of a yellow-white solid.

c. 3-Iodoacetamidodigoxigenin (D)

180 mg of 3-Aminodigoxigenin and 70 $\mu$l of triethylamine were dissolved in 8 mls of methanol. 135 mg of iodoacetic anhydride was added with rapid stirring. TLC showed complete conversion of the starting material to a more mobile product. The solvent was stripped off, and the residue dissolved in 30 mls of chloroform which contained some methanol. The chloroform solution was washed with 30 mls of 0.1N HCl and the aqueous layer back-washed with two volumes of 30 mls of chloroform. The organic layers were dried with anhydrous sodium sulfate and the solvent was stripped off leaving 240 mg of oily residue. The oily residue was dissolved in 3 mls of tetrahydrofuran and 30 mls of hexane was added and the precipitate was collected by filtration and dried to 110 mg of off-white powder.

Example 16C

Preparation of 3-(Iodoacetamido-beta-alaninyl)-aminodigoxigenin (DB)

92 mg of 3-Aminodigoxigenin and 15 mls of triethylamine were dissolved in 1.0 mls of methanol. 91 mg of iodoacetamido-beta-alanine N-hydroxysuccinimide ester were added. TLC showed complete reaction within 20 min. The mixture was partitioned between 30 mls of 10% sodium carbonate and three volumes of 10 mls of chloroform plus 5 mls of methanol. The organic layer was dried with anhydrous sodium sulfate and the solvent was stripped off, leaving 150 mg of residue. The residue was dissolved in 200 μl of methanol and 2 mls of chloroform, and applied to a silica gel preparatory TLC plate. The plate was developed in chloroform:methanol:acetic acid (100:12:2). The band corresponding to the desired product was scraped off, eluted with methanol, and the solvent was stripped off leaving 100 mg of waxy solid.

a. 4' 5'-dimethyl fluorescein 5.92 g of phthalic anhydride and 9.92 g of 2-methylresorcinol were ground together. 5.3 mls of concentrated sulfuric acid was added and the mixture was heated to 135° C. for 30 min. The resulting yellow-red solid was dissolved by crushing in water and a total of 21 g of 50% NaOH was added. The solution was diluted to 900 mls with water and then acidified with 20 mls of acetic acid. The thick orange precipitate was boiled for 20 min. The mixture was filtered after it cooled to room temperature and resulted in 11.9 g of dried solid.

b. 4' 5'-dimethyl fluorescein diphosphate (DMFDP)

36 mg of 4' 5'-dimethyl fluorescein (DMF) was dissolved in 100 mls of pyridine. The solution was added to 50 μl of phosphorous oxychloride in 100 μl of pyridine and agitated for 5 min. The solution was added to 10 mls of rapidly vortexing water. 3 mls of 2M magnesium chloride was added to 7 ml of the solution. 12 drops of 6N NaOH was added to adjust the pH to 8.0 and the mixture was centrifuged to sediment the precipitate. The supernate had a nominal concentration of 7 mM 4' 5'-dimethyl fluorescein diphosphate. The product was characterized by exposure of a dilution (280 μM) and monitoring the absorbance at 500 nm following the addition of AP.

Table 6 lists the hybrid enzyme-ligand conjugates prepared. Ligands were conjugated to hybrid enzymes as described. The number in parentheses is the Normalized Residual Activity in the presence of excess monoclonal antibody expressed as a percentage of the control (without antibody=100). Numbers less than 100 indicate antibody induced attenuation of hybrid enzyme-ligand conjugate activity. Numbers greater than 100 indicate activation.

TABLE 6

| Theophylline: | | | | | |
|---|---|---|---|---|---|
| Ligand: | T1 | T2 | T3 | T4 | T6 |
| Hybrid | | | | | |
| APKJ3: | (98) | (96) | (54) | (21) | (31) |
| APKJ4: | (26) | (42) | (51) | (50) | (50) |
| APKJ5: | (100) | | | (98) | (42) |
| APKJ103: | (100) | | | (40) | |
| APKJ104: | (78) | | | (77) | |
| Thyroxine: | | | | | |
| Ligand: | Thy | ThyA | ThyB | ThyC | |
| Hybrid: | | | | | |
| APKJ3: | (75) | (106) | (115) | (120) | |
| APKJ4: | (97) | (86) | (87) | (87) | |
| APKJ5: | (100) | (100) | (141) | (134) | |

TABLE 6-continued

| Digoxigenin: | | | | |
|---|---|---|---|---|
| Ligand: | D | DA | DB | DC |
| Hybrid: | | | | |
| APKJ3: | (94) | (39) | (52) | (47) |
| APKJ4: | (82) | (94) | (90) | (91) |
| APKJ5: | (99) | (97) | (98) | (95) |
| APKJ103: | (107) | (102) | (96) | (97) |
| APKJ104: | (92) | (102) | (105) | (105) |

In table 6, hybrid APKJ3 conjugated to T1 is herein referred to as T1-3; T2 conjugated to APKJ4 is herein referred to as T2-4, this classification is similarly applied to the other conjugates. T1 refers to aminomethyltheophylline as ligand; T2 refers to aminoethyltheophylline as ligand; T3 refers to aminopropyltheophylline as ligand; T4 refers to aminobutyltheophylline as ligand; and T6 refers to aminohexyltheophylline as ligand. Thy refers to iodo-acetic-amide of thyroxine as ligand; ThyA refers to thyroxine with a glycine in the linker; ThyB refers to thyroxine with β-alanine in the linker; ThyC refers to thyroxine with a gamma amino-butyric acid in the linker. D refers to iodo-acetic-amide of digoxigenin as ligand; DA refers to digoxigenin with a glycine in the linker; DB refers to digoxigenin with a β-alanine in the linker; DC refers to digoxigenin with a gamma aminobutyric acid in the linker.

Example 17

Protection and Purification of Enzyme Hybrids with a Cystein Mutation 250 mls of APKJ3 was incubated for 1 hour with 10 mM of L-Cysteine. Air was then bubbled through the mixture until a sample gave a negative test for sulfhydryl with Ellman's reagent. The mixture was then loaded on a DEAE column and eluted with a 0 to 500 mM gradient of NaCl. 120 mls of eluent was collected which contained 1.886 mg/ml of protein with a specific AP activity of 8.43 U/mg.

Example 18

Deprotection and Conjugation of Hybrid Enzymes with Theophylline Ligands 7.0 mls of each cysteine protected APKJ3 and APKJ4 were bubbled briefly with nitrogen, then mixed with 35 mls of 200 mM DTT and incubated for 60 min. at room temperature. 18 mg of the ligand derivative T1, T2, T3, T4 or T6 was dissolved in 400 mls of DMF in 12×75 mm test tubes. Brief heating was necessary to dissolve some of the derivatives. 1.0 ml of the deprotected hybrid enzyme solution was added to 200 mls of the DMF solutions. After 90 min. the mixtures were passed through 5 mls Pierce Kwik columns (Pierce, Rockford, Ill.) with 50 mM Tris, pH 8.0, containing 1 g/L of sodium azide. 2.0 mls of the protein solution was collected and mixed with 20 μl of a solution containing 100 mM magnesium chloride and 10 mM zinc chloride. Hybrid enzyme-ligand conjugates were prepared with derivatives T1 through T6. The protein concentrations were determined using Pierce Coomassie Blue protein reagent calibrated with standard BSA solutions.

Example 19

Evaluation of Hybrid Enzyme-Ligand Conjugates

Figure 20:
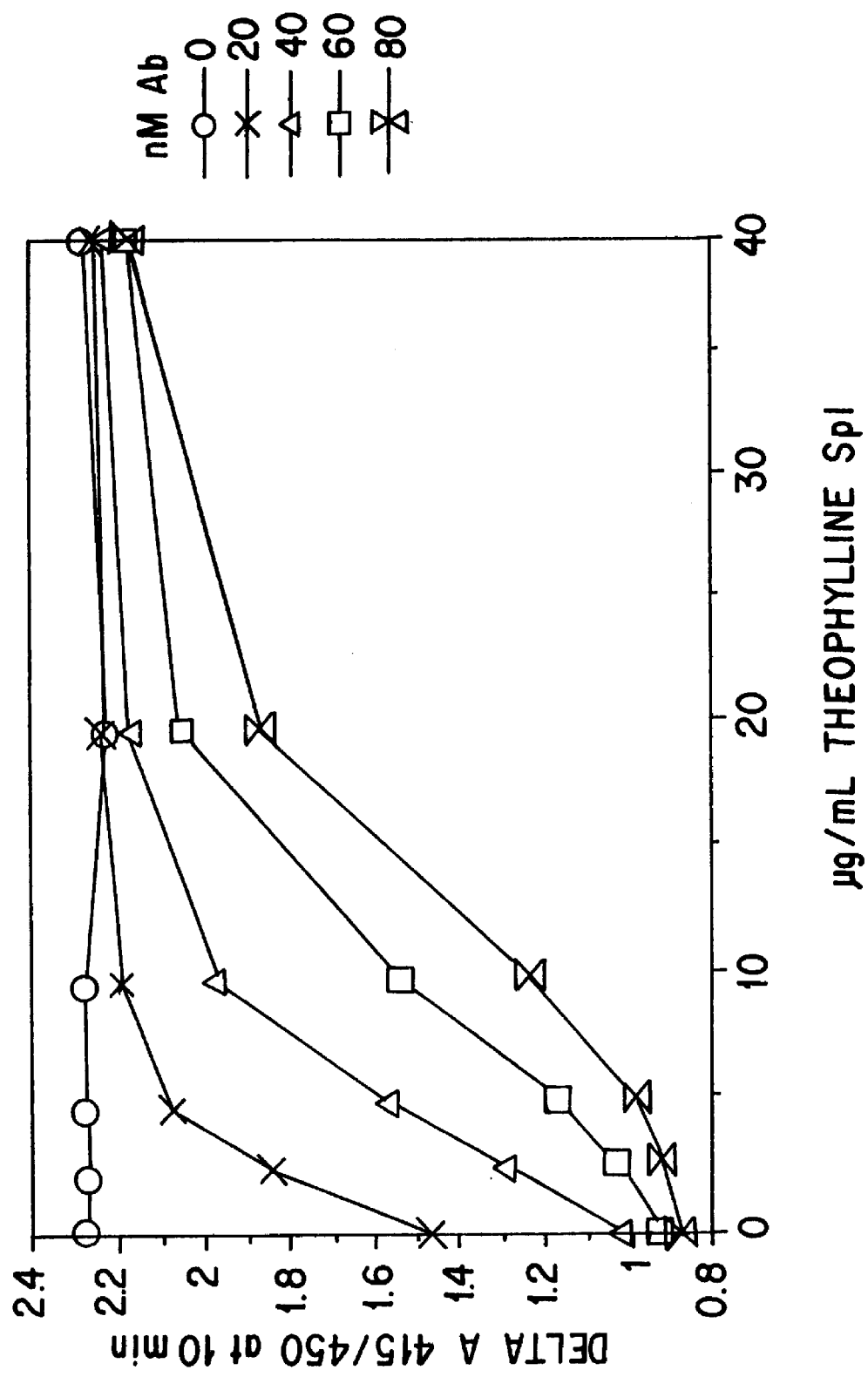
FIG. 20 shows the effect of adding microliter ($\mu$l) quantities of serum-based theophylline calibrators to a theophylline hybrid enzyme-ligand conjugate (T1-3) in the presence of various concentrations of sheep antibodies.

Samples of hybrid enzyme-ligand conjugates T1-3 and T4-3 (Table 5) were diluted to 43 ug/ml in 5 mg/ml of BSA, 50 mM Tris, pH 8.0. Assuming a molecular weight of 86 kD for the enzyme, the concentration is 0.5 mM. Solutions of sheep polyclonal and mouse monoclonal antibodies to theophylline were prepared at 1.0 mM. A VP (Abbott Laboratories, Abbott Park, Ill.) multicuvette was loaded from down to 0 µl of 5 mg/ml of BSA and from 0 to 20 µl of 1.0 mM of antibody, keeping the total volume in each position at 20 µl. The antibody consisted of either sheep polyclonal or mouse monoclonal specific to theophylline, the concentrations of which had been determined by titration into a solution of a fluorescent theophylline derivative of known concentration. 10 µl of 0.5 mM hybrid enzyme-ligand conjugate T1-3 or T4-3 was added to each position of the multicuvette. The multicuvette was placed on the VP instrument (Abbott Labs) and run at 37° C. using a substrate consisting of 5 mg/ml of PNPP, 50 mM Tris, 1.0 mM $MgCl_2$, 0.1 mM of $ZnCl_2$, at pH 8.0, and a filter combination of 415/450 nm. Absorbance values were collected as differences from the absorbance at time=0 (addition of substrate to cuvette). Results at 10 min. are presented in FIG. 20.

Example 20

Assay Method

The present invention is adaptable to many random access and clinical chemistry analyzers with spectrophotometric capabilities. Examples include the Cobas Mira (Hoffmann-LaRoche, Nutley, N.J.), the Hitachi (Hitachi Scientific Instruments, Mountain View, Calif.), the Monarch (Instrumentation Laboratory, Lexington, Mass.), or the EPx/Spectrum® (Abbott Laboratories). Small sample volumes can be used on these analyzers and timing can vary from 4–20 min. depending on the analyzer. Three mixtures can be used: substrate, conjugate, and antisera (or antibody). In the assay, the analyte competes with enzyme-ligand conjugate for the binding molecule. With no analyte present in the reaction mixture, the signal, such as absorbance, is low. The reason is that the binding molecule interacts with the hybrid enzyme-ligand conjugate and generates less signal from the substrate-hybrid enzyme ligand conjugate interaction. When analyte is present, the binding molecule and the analyte interact and thus the active site on the hybrid enzyme-ligand conjugate is left available. This causes more substrate to come into the active site and interact thereby giving more signal, such as higher absorbance, and represents more specific activity of the hybrid enzyme-ligand conjugate. As the concentration of analyte increases, the signal also increases. This generates a curve from which the concentration of the analyte in the test sample can be determined. The amount of attenuation is controlled by the amount of substrate, the amount and type of binding molecule, the linker arm used in the hybrid enzyme-ligand conjugate, the expressed hybrid enzyme used, and the amount of analyte present. One successful application of this technology is the theophylline hybrid enzyme-ligand conjugate on the Cobas Mira. Other small analytes, such as digoxin and phenytoin, can also be adapted to this technology. Large molecules such as TSH an hCG can also be used in this assay format.

One assay of the present invention was developed on the Cobas Mira in a three reagent configuration using T1–3 and Theophylline Polyclonal Sheep Antisera #664-43 (Abbott Laboratories). The Cobas Mira Instrument can utilize either two reagent or three reagent configurations when performing assays. The instrument operates with two probes, the reagent probe and the sample probe. The reagent probe picks up Reagent #1 and the sample probe picks up the test sample. Both Reagent #1 and sample are dispensed into a cuvette. The reagent then picks up Reagent #2 and dispenses in the cuvette. The reagent probe will pick up Reagent #3 (in a three reagent assay) and dispense it in the cuvette. The configuration on the Cobas Mira assay was as follows:

Reagent #1: 250 µl of PNPP at 5 mg/ml in 0.1M Tris buffer with 1 mM $MgCl_2$, 0.1 mM $ZnCl_2$, and 0.5% BSA (pH 7.5).

Sample: 2 µl of sample (using TDx® Theophylline Calibrators and Controls) washed with 98 µl of distilled $H_2O$.

Reagent #2: 35 µl of Polyclonal Sheep Antisera at $1\times10^{-6}$M washed with 2 µl of distilled $H_2O$.

Reagent #3: 10 µl of T1-3 (dissolved in 0.1M Tris buffer with 0.1 mM $ZnCl_2$ and 1 mM $MgCl_2$ to an A450 nm of 0.1) washed with 2 µl of distilled $H_2O$.

The assay was run on the Cobas Miras instrument as follows:

Reagent #1 was picked up with the reagent probe and then the test sample and water wash were picked up with the sample probe. Reagent #1 was dispensed into the cuvette followed by the test sample and wash. The mixture was then mixed with the reagent probe. The reagent probe then picked up Reagent #2 and dispensed it into the cuvette and mixed. About 20 seconds later, Reagent #3 was picked up by the reagent probe, dispensed into the cuvette, and mixed. The whole mixture was then incubated for a total of 4–10 min. A calibration curve was established on the Cobas Mira instument and then samples were read off this curve.

A two reagent system was also tested on the Cobas Mira instrument as follows:

Reagent #1: 280 µl of a PNPP and Theophylline polyclonal sheep antisera mixture in the same buffer as above.

Sample: 2 µl of sample washed with 10 mls of water.

Reagent #2: 10 µl of T1-3 washed with 2 mls of distilled water.

The two reagent system was performed as above, with the exception of omitting Reagent #3.

For endogenous AP samples, 80 mM L-Phenylalanine and 3 mM Levamisole were added into the 5 mg/ml of PNPP substrate.

Figure 21:
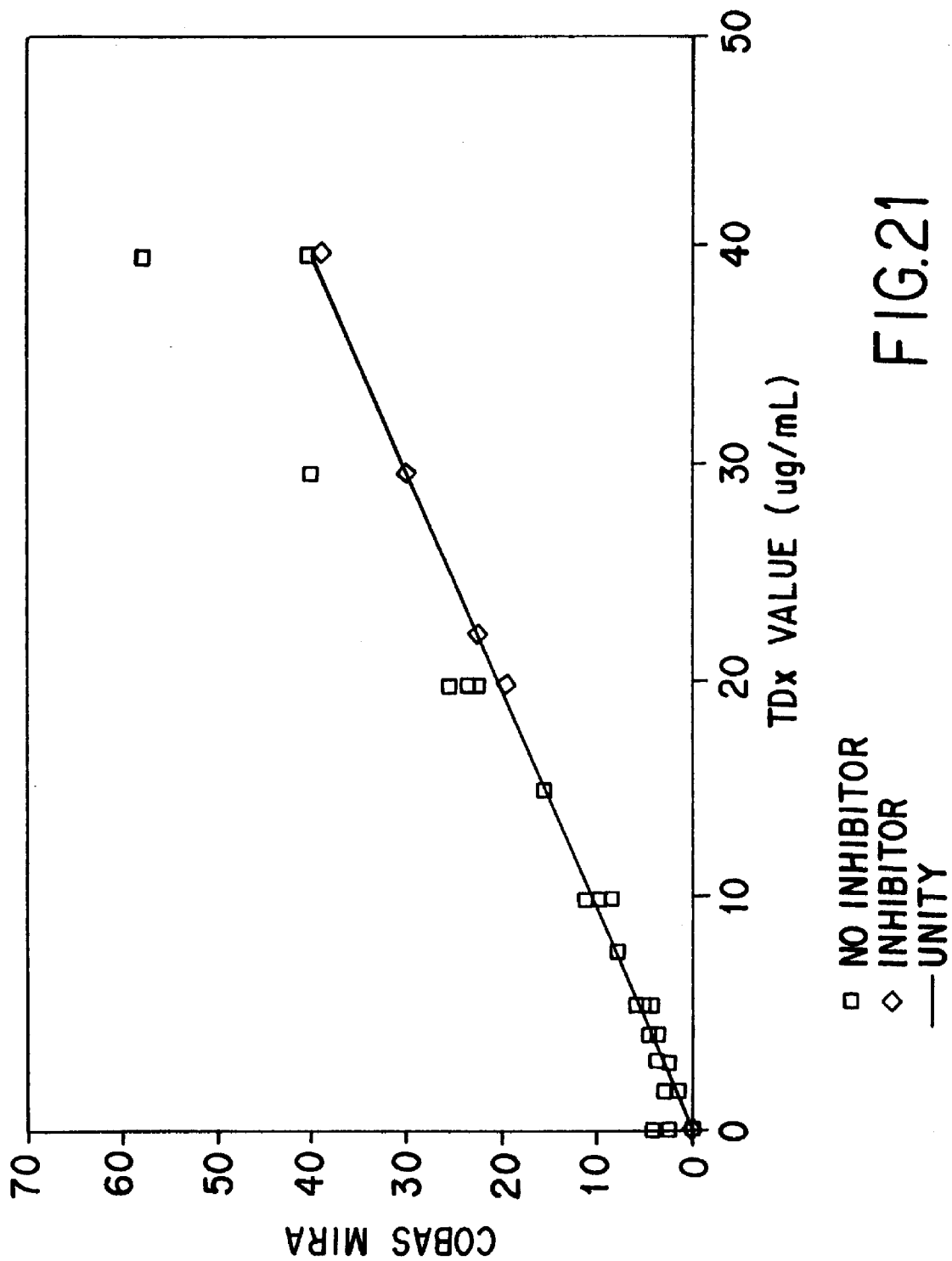
FIG. 21 shows a correlation diagram of endogenous AP samples spiked into a theophylline sample.

Two correlations performed on the Cobas Mira are given below:

FIG. 21 shows a spiked sample correlation of endogenous AP samples spiked into a theophylline sample. The correlation represents the above Cobas Mira assay versus the TDx Theophylline II assay (Abbott Laboratories). Linear regression of the data with inhibitors shown in FIG. 21 yielded a correlation coefficient of 0.997, a slope of 0.971, and a y-intercept of 0.373. This assay accuracy reports theophylline levels, as demonstrated by a slope value and correlation coefficient very close to 1.0. Linear regression of the data without the inhibitors yielded a correlation coefficient of 0.970, a slope of 1.199, and a y-intercept of −0.693. The increased slope for these data indicate that the endogenous AP will produce a positive inteference unless inhibitors are present.

Sensitivity was also tested in the Cobas Mira assay using 20 replicate samples of human serum absent theophylline and determining the mean minus 2 standard deviations using both absorbances and a curvefit program. The sensitivity was 0.79 mg/ml which was comparable to the TDx Theophylline stated value of 0.82 mg/ml.

Recovery was also performed on the Cobas Mira instrument. A set of calibrators were made in both a plasma and a TDx buffer matrix. The samples were run side by side and were within ±10% of each other. When an endogenous patient sample was diluted to a 1:2 or a 1:4, the sample was also recovered at ±10%.

Example 21

Preparation of Human Chorionic Gonapotropin (hCG) Hybrid Enzyme-Ligand Conjugate A GF5 desalting column (Pierce) was equilibrated with degassed buffer containing 0.1M Tris, 1 mM DTT, pH 8.0. The column was washed right before use with degassed buffer containing 0.1M Tris, pH 8.0 until the eluate was tested negative by Ellman's reaction (Ellman, G. L. (1958) Arch. Biochem. Biophys. 74, 443). A BioGel P-2 column (0.9×7.5 cm) was equilibrated with 0.1M Tris, pH 7.0. A solution of 2 mg (20 nmoles) of purified APJK4 and 1 mM DTT in 0.69 ml of 50 mM Tris, 100 mM NaCl, pH 8.0 was incubated at room temperature for 30 min. The reaction mixture was chromatographed over the GF5 column. The fractions at the void volume were pooled. A solution of 1 mg (0.24 umoles) of CTP peptide (SEQ. I.D. NO. 29) (Asp-Pro-Arg-Phe-Gln-Asp-Ser-Ser-Ser-Ser-Lys-Ala-Pro-Pro-Pro-Ser-Leu-Pro-Ser-Pro-Ser-Arg-Leu-Pro-Gly-Pro-Ser-Asp-Thr-Pro-Ile-Leu-Pro-Gln-Lys-Lys-Lys-Lys-Lys), (Bidart, J. M. et al (1985) J. Immunology. 134, 457) in 300 $\mu$l of 0.1M sodium phosphate, pH 7.0 was treated with 30 $\mu$l of 28 mM sulfosuccinimidyl(4-iodoacetyl)aminobenzoate (Pierce) in the same buffer. The mixture was allowed to react at 30° C. for 30 min. The mixture was then passed through the P-2 column. Fractions at the void volume were pooled. The two pools from each column were combined. The pH of resulting solution was adjusted with 1N NaOH to pH 8.0. The mixture was rotated end-over-end overnight at 2°–8° C., and then 3 hours at room temperature. The whole reaction mixture was exhaustively dialyzed against 0.1M Tris, 1 mM $MgCl_2$, 0.1 mM $ZnCl_2$, pH 8.0. The dialyzed material was stored at 2°–8° C.

Example 22

Assays for Human Chorionic Gonadotropin (hCG)

Figure 22:
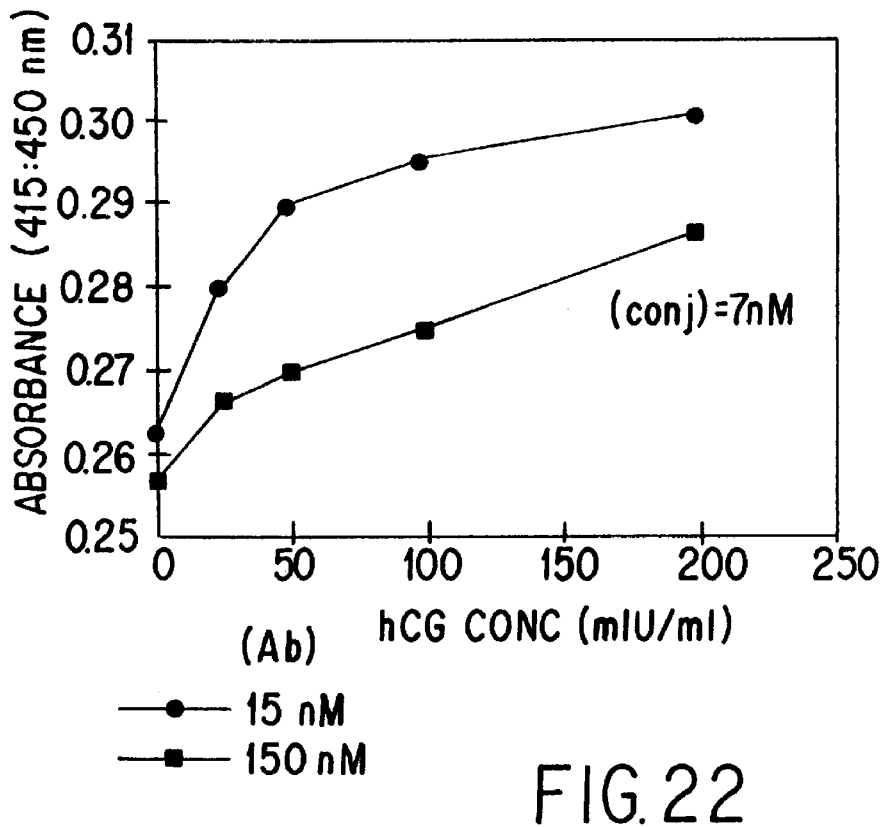
FIG. 22 shows a calibration curve for human chorionic gonadotropin (hCG) using hybrid enzyme-ligand conjugate, CTP-APKJ4, antibody and hCG standards.

The antibody used in the assay was affinity-purified from goat anti-β-human chorionic gonadotropin through a column containing immobilized CTP peptide. The antibody reagent and the conjugate were diluted to working concentrations of 0.17 $\mu$g/$\mu$l and 5.4 $\mu$g/$\mu$l respectively with 1% bovine serum albumin in 0.1M Tris, 1 mM $MgCl_2$, 0.1 mM $ZnCl_2$ at pH 8.0. Calibration standards containing 0, 25, 50, 100 and 200 mIU/ml of hCG in calf serum were from Abbott's β-HCG 15/15 Test Kit™ (Abbott Laboratories). Twenty five mls (25 ml) of each of the standards were mixed with 50 $\mu$l of the antibody and 50 $\mu$l of the conjugate. The mixtures were allowed to sit at room temperature for about 10 min. This was followed by the addition of 250 $\mu$l of 0.2 mM PNPP in 1M Tris, pH 8.5. Bichromatic OD readings (415:450 nm) were made after 8 min. via Abbott VP™ analyzer (Abbott Laboratories). In a separate assay, the experiment was essentially identical except that an antibody concentration of 17 $\mu$g/ml was used. The observed OD values for both runs were plotted against the known concentrations of the standards (see FIG. 22).

Example 23

Preparation of the Ferritin Conjugate of AP Hybrid Enzyme-Ligand Conjugate

A GF5 desalting column (Pierce) was equilibrated with degassed buffer containing 0.1M Tris, 1 mM DTT, pH 8.0. The column was washed before use with degassed buffer containing 0.1M Tris, pH 8.0 until the eluate was tested negative by Ellman's reaction (Ellman, G. L. (1958) Arch. Biochem. Biophys. 74, 443). A BioGel P-2 column (0.9×7.5 cm) was equilibrated with 0.1M Tris, pH 7.0. A solution of 1 mg (10 nmoles) of purified APJK4 and 1 mM DTT in 0.51 ml of 50 mM Tris, 100 mM NaCl, pH 8.0 was incubated at room temperature for 30 min. The reaction mixture was chromatographed over the GF5 column. The fractions at the void volume were pooled. A solution of 1 mg (0.24 umoles) of the nona-peptide (SEQ. I.D. NO. 30) (Lys-Pro-Asp-Glu-Asp-Asp-Trp-Glu-Ser, a.a. 83–91 of human spleen apoferritin), (Addison, J. M. et al (1984) Febs Letters 175, 333) in 300 $\mu$l of 0.1M sodium phosphate pH 7.0, was treated with 50 $\mu$l of 40 mM sulfosuccinimidyl(4-iodoacetyl) aminobenzoate (Pierce) in the same buffer. The pH of the mixture was adjusted to 7.0 with 1N NaOH. The solution was allowed to sit at 30° C. for 30 min. The mixture was then passed through the P-2 column. Fractions at the void volume were pooled. The two pools from each column were combined. The resulting solution was allowed to sit at room temperature for 30 min. before it was rotated end-over-end overnight at 2°–8° C. The whole reaction mixture was exhaustively dialyzed against 0.1M Tris, 1 mM $MgCl_2$, 0.1 mM $ZnCl_2$, pH 8.0. About two mls of the dialyzed material was recovered and stored at 2°–80° C.

Example 24

Figure 23:
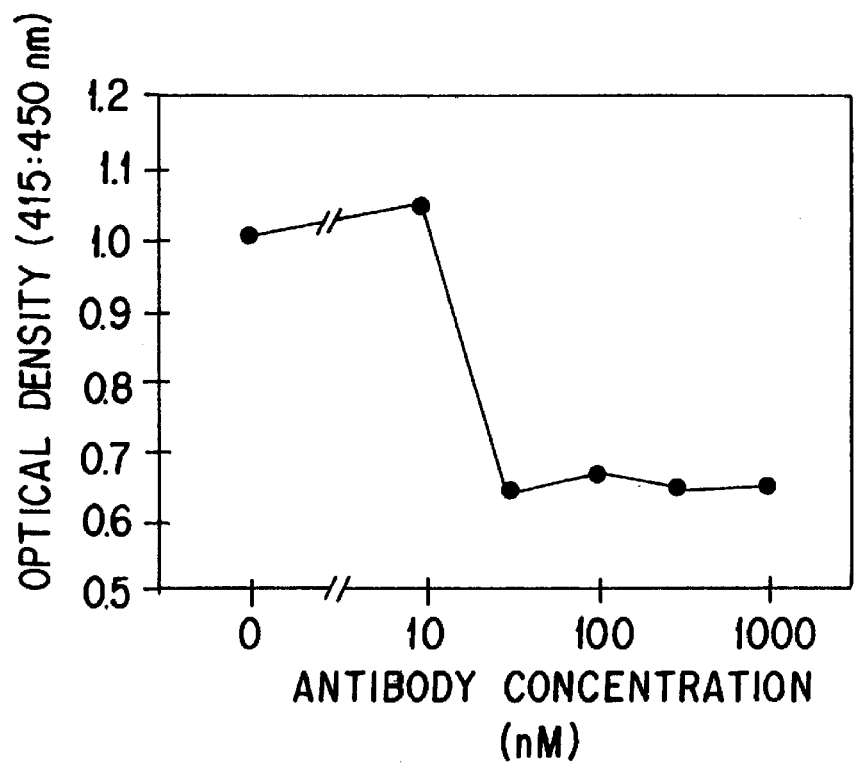
FIG. 23 shows the enzymatic activity attenuation of ferritin hybrid enzyme-ligand conjugate.

Antibody-Induced Modulation of Activity of the Ferritin Conjugate of AP Hybrid Enzyme-Ligand Conjugate The monoclonal anti-ferritin antibody reagent (10 mg/ml) was diluted to 1:10, 1:30, 1:100, 1:300, and 1:1000 with 1% bovine serum albumin in 0.1M Tris, 1 mM $MgCl_2$, 0.1 mM $ZnCl_2$ at pH 8.0. The hybrid enzyme-ligand conjugate (0.5 mg/ml) was diluted to 1:200 with the same diluent. Fifty $\mu$l of each of the diluted antibody solution were mixed with equal volumes of the hybrid enzyme-ligand conjugate. The mixtures were incubated at room temperature for about 10 min. This was followed by the addition of 250 $\mu$l of 0.2 mM PNPP in 1M Tris, pH 8.5. Bichromatic OD measurements (415:450 nm) were made after 10 min. via Abbott VP™ analyzer. The observed OD values were plotted against the known concentrations of the antibody (see FIG. 23).

The foregoing description of the presently preferred embodiments of the present invention has been offered for purposes of illustration and description. It is not intended to limit the scope of the invention, which is defined by the appended claims and their equivalents. Various modifications and variations of the preferred embodiments are possible in light of the above teachings and will be apparent to persons skilled in the art. Such modifications and variations do not depart from the spirit or scope of the invention and it is therefore intended that the scope of the invention be defined by the appended claims, including all equivalents.

What is claimed is:

1. A hybrid enzyme-ligand conjugate, wherein amino acid Asparagine at position 263 of a starting alkaline phosphatase, numbered in accordance with SEQ ID NO:2, is replaced by Cysteine, and the hybrid enzyme-ligand conjugate exhibits an enzymatic activity of the starting alkaline phosphatase.

2. A hybrid enzyme-ligand conjugate, wherein amino acid Lysine at position 177 of a starting alkaline phosphatase, numbered in accordance with SEQ ID NO:2, is replaced by Cysteine, and the hybrid enzyme-ligand conjugate exhibits an enzymatic activity of the starting alkaline phosphatase.

3. A hybrid enzyme-ligand conjugate, wherein amino acid Lysine at position 209 of a starting alkaline phosphatase, numbered in accordance with SEQ ID NO:2, is replaced by Cysteine, and the hybrid enzyme-ligand conjugate exhibits an enzymatic activity of the starting alkaline phosphatase.

4. A hybrid enzyme-ligand conjugate, wherein amino acid Lysine at position 328 of a starting alkaline phosphatase, numbered in accordance with SEQ ID NO:2, is replaced by Cysteine, and the hybrid enzyme-ligand conjugate exhibits an enzymatic activity of the starting alkaline phosphatase.

5. A hybrid enzyme-ligand conjugate, wherein amino acid Glutamine at position 291 of a starting alkaline phosphatase, numbered in accordance with SEQ ID NO:2, is replaced by Cysteine, and the hybrid enzyme-ligand conjugate exhibits an enzymatic activity of the starting alkaline phosphatase.

6. A hybrid enzyme-ligand conjugate, wherein amino acid Aspartic Acid at position 294 of a starting alkaline phosphatase, numbered in accordance with SEQ ID NO:2, is replaced by Cysteine, and the hybrid enzyme-ligand conjugate exhibits an enzymatic activity of the starting alkaline phosphatase.

7. A hybrid enzyme-ligand conjugate, wherein amino acid Glutamic Acid at position 407 of a starting alkaline phosphatase, numbered in accordance with SEQ ID NO:2, is replaced by Cysteine, and the hybrid enzyme-ligand conjugate exhibits an enzymatic activity of the starting alkaline phosphatase.

8. A hybrid enzyme-ligand conjugate, wherein amino acid Aspartic Acid at position 408 of a starting alkaline phosphatase, numbered in accordance with SEQ ID NO:2, is replaced by Cysteine, and the hybrid enzyme-ligand conjugate exhibits an enzymatic activity of the starting alkaline phosphatase.

9. A hybrid enzyme-ligand conjugate, wherein amino acid Aspartic Acid at position 380 of a starting alkaline phosphatase, numbered in accordance with SEQ ID NO:2, is replaced by Cysteine, and the hybrid enzyme-ligand conjugate exhibits an enzymatic activity of the starting alkaline phosphatase.

10. A hybrid enzyme-ligand conjugate, wherein amino acid Asparagine at position 117 of a starting alkaline phosphatase, numbered in accordance with SEQ ID NO:2, is replaced by Cysteine, and the hybrid enzyme-ligand conjugate exhibits an enzymatic activity of the starting alkaline phosphatase.

11. A recombinant DNA molecule encoding an alkaline phosphate wherein the recombinant DNA molecule comprises a synthetic DNA fragment encoding the Cysteine as recited in claim 1.

12. A recombinant DNA molecule encoding an alkaline phosphate wherein the recombinant DNA molecule comprises a synthetic DNA fragment encoding the Cysteine as recited in claim 2.

13. A recombinant DNA molecule encoding an alkaline phosphate wherein the recombinant DNA molecule comprises a synthetic DNA fragment encoding the Cysteine as recited in claim 3.

14. A recombinant DNA molecule encoding an alkaline phosphate wherein the recombinant DNA molecule comprises a synthetic DNA fragment encoding the Cysteine as recited in claim 4.

15. A recombinant DNA molecule encoding an alkaline phosphate wherein the recombinant DNA molecule comprises a synthetic DNA fragment encoding the Cysteine as recited in claim 5.

16. A recombinant DNA molecule encoding an alkaline phosphate wherein the recombinant DNA molecule comprises a synthetic DNA fragment encoding the Cysteine as recited in claim 6.

17. A recombinant DNA molecule encoding an alkaline phosphate wherein the recombinant DNA molecule comprises a synthetic DNA fragment encoding the Cysteine as recited in claim 7.

18. A recombinant DNA molecule encoding an alkaline phosphate wherein the recombinant DNA molecule comprises a synthetic DNA fragment encoding the Cysteine as recited in claim 8.

19. A recombinant DNA molecule encoding an alkaline phosphate wherein the recombinant DNA molecule comprises a synthetic DNA fragment encoding the Cysteine as recited in claim 9.

20. A recombinant DNA molecule encoding an alkaline phosphate wherein the recombinant DNA molecule comprises a synthetic DNA fragment encoding the Cysteine as recited in claim 10.

* * * * *